(12) United States Patent
Davis et al.

(10) Patent No.: US 7,323,464 B2
(45) Date of Patent: Jan. 29, 2008

(54) PYRIDINE AND PYRIMIDINE DERIVATIVES

(75) Inventors: Jeremy Martin Davis, Wokingham (GB); Barry John Langham, Reading (GB); Manisha Naik, Reading (GB); Daniel Christopher Brookings, Reading (GB); Rachel Jane Cubbon, Slough (GB); Richard Jeremy Franklin, Slough (GB)

(73) Assignee: Celltech R&D Limited, Berkshire (GB)

( * ) Notice: Subject to any disclaimer, the term of this patent is extended or adjusted under 35 U.S.C. 154(b) by 446 days.

(21) Appl. No.: 10/495,885

(22) PCT Filed: Nov. 20, 2002

(86) PCT No.: PCT/GB02/05196

§ 371 (c)(1),
(2), (4) Date: Aug. 3, 2004

(87) PCT Pub. No.: WO03/045941

PCT Pub. Date: Jun. 5, 2003

(65) Prior Publication Data

US 2005/0080258 A1    Apr. 14, 2005

(30) Foreign Application Priority Data

Nov. 21, 2001   (GB) ................... 0127929.8

(51) Int. Cl.
*C07D 403/04* (2006.01)
*A61K 31/506* (2006.01)

(52) U.S. Cl. .............. 514/235.8; 514/252.14; 514/275; 544/122; 544/295; 544/323

(58) Field of Classification Search ........ 544/122, 544/295, 323; 514/235.8, 252.14, 275
See application file for complete search history.

(56) References Cited

U.S. PATENT DOCUMENTS 6,162,927 A * 12/2000 Winn et al. ............. 548/526

FOREIGN PATENT DOCUMENTS

| WO | WO 99/58523 A1 | 11/1999 |
|---|---|---|
| WO | WO 00/59510 | * 10/2000 |
| WO | WO 01/64676 A3 | 9/2001 |

OTHER PUBLICATIONS

Ulrich, Crystallization—4. Crystal Characteristics, Kirk-Othmer Encyclopedia of Chemical Technology, Aug. 2002.*
Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Adams, J.L., et al., "p38 MAP kinase: molecular target for the inhibition of pro-inflammatory cytokines," Progress in Medicinal Chemistry, Elsevier Science, King, F.D., et al. (Eds.), 2001, 38, 1-60.
Allen, M., et al., "Deficiency of the stress kinase p38α results in embryonic lethality: characterization of the kinase dependence of stress responses of enzyme-deficient embryonic stem cells," *J. Exp. Med.*, 2000, 191, 859-869.
Badger, A.M., et al., "Pharmacological profile of SB 203580, a selective inhibitor of cytokine suppressive binding protein/p38 kinase, in animal models of arthritis, bone resorption, endotoxin shock and immune function," *J. Pharm. & Exp. Ther.*, 1996, 279, 1453-1461.
Basha, A., et al., "Structure-activity relationships of pyrimidopyrimidine series of 5-lipoxygenase inhibitors," *Med. Chem. Res.*, 1996, 6, 61-67.
Cohen, P., "The search for physiological substrates of MAP and SAP kinases in mammalian cells," *Trends Cell Biol.*, 1997, 7, 353-361.
Dinarello, C.A., "An update on human interleukin-1 : from molecular biology to clinical relevance," *J. of Clinical Immunology*, 1985, 5(5), 287-297.
Doza, Y.N., et al., "Activation of the MAP kinase homologue RK requires the phosphorylation of Thr-180 and Tyr-182 and both residues are phosphorylated in chemically stressed KB cells," *FEBS Lett.*, 1995, 364, 223-228.
Driver, M.S., et al., "A second-generation catalyst for aryl halide amination: mixed secondary amines from aryl halides and primary amines catalyzed by (DPPF)PdCl$_2$," *J. Am. Chem. Soc.*, 1996, 118, 7217-7218.
Enslen, H., et al., "Selective activation of p38 mitogen-activated protein (MAP) kinase isoforms by the MAP kinase kinases MKK3 and MKK6," *J. of Biol. Chem.*, 1998, 273(3), 1741-1748.

(Continued)

Primary Examiner—Deepak Rao
(74) Attorney, Agent, or Firm—McDonnell Boehnen Hulbert & Berghoff LLP

(57) ABSTRACT

Compounds of formula (1) are described in which $R^a$ and $R^b$ is each independently a hydrogen atom or a group $R^c$, or $R^a$ and $R^b$ together form an oxo (=O) or thio (=S) group; X is a N atom or an optionally substituted CH group: Y is a —O— or —S— atom or —SO— or —SO$_2$— group or an optionally substituted —CH$_2$— or —NH— group with the proviso that when $R^a$ and $R^b$ together form an oxo (=O) or thio (=S) group Y is an optionally substituted —CH$_2$— or —NH-group; $L^1$ is a covalent bond or a linker atom or group; p is zero or the integer 1; $Alk^1$ is an optionally substituted $C_{1-10}$aliphatic or $C_{1-10}$heteroaliphatic chain; n is zero the integer 1, 2 or 3 with the proviso that when n is zero Y is an optionally substituted —CH$_2$— group; Ar is an optionally substituted $C_{6-12}$aromatic or $C_{1-9}$heteroaromatic group; m is zero or the integer 1, 2 or 3; q is zero or the integer 1 or 2; $R^1$, $R^c$ and $R^d$ are hydrogen atoms or the substituents described in the patent specification; and the salts, solvates, hydrates and N-oxides thereof. The compounds are potent and selective inhibitors of p38 kinase and are useful in the treatment of immune or inflammatory disorders.

14 Claims, No Drawings

OTHER PUBLICATIONS

Griswold, D.E., et al., "Pharmacology of cytokine suppressive anti-inflammatory drug binding protein (CSBP), a novel stress-induced kinase," *Pharmacol. Comm.*, 1996, 7, 323-329.

Grunberg, K., et al., "Effect of rhinovirus 16 (RV16) cold on airway responsiveness to indirect stimuli in asthmatics," *Am. J. Crit. Care Med.*, 1997, 155, p. A743 (abstract).

Hale, K.K., et al., "Differential expression and activation of p38 mitogen-activated protein kinase $\alpha$, $\beta$, $\gamma$, and $\delta$ in inflammatory cell lineages," *Am. J. of Immun.*, 1999, 162, 4246-4252.

Hunter, T., "Protein kinase classification," *Methods in Enzymology, Academic Press*, 1991, 200, 3-37.

Kotlyarov, A., et al., "MAPKAP kinase 2 is essential for LPS-induced TNF-$\alpha$ biosynthesis," *Nature Cell Biol.*, 1999, 1, 94-97.

Lee, J.C., et al., "Bicyclic imidazoles as a novel class of cytokine biosynthesis inhibitors," *Annals N.Y. Acad. Sci.*, 1993, 696, 149-170.

Lee, J.C., et al., "Inhibition of monocyte IL-1 production by the anti-inflammatory compound, SK&F 86002," *Int. J. Immunopharm.*, 1988, 10(7), 835-843.

Lee, J.C., et al., "A protein kinase involved in the regulation of inflammatory cytokine biosynthesis," *Nature*, 1994, 372, 739-746.

Louie, J., et al., "Palladium-catalyzed amination of aryl triflates and importance of triflate addition rate," *J. Org. Chem.*, 1997, 62, 1268-1273.

McDonnell, P.C., et al., "Localization of the human stress responsive MAP kinase-like CSAIDs binding protein (CSBP) gene to chromosome 6p21.3/21.2," *Genomics*, 1995, 28, 301-302.

Subauste, M.C., et al., "Infection of a human respiratory epithelial cell line with rhinovirus, Induction of cytokine release and modulation of susceptibility to infection by cytokine exposure," *J. Clin. Invest.*, 1995, 96, 549-557.

Takekawa, M., et al., "A family of stress-inducible GADD45-like proteins mediate activation of the stress-responsive MTK1/MEKK4 MAPKKK," *Cell*, 1998, 95, 521-530.

Turner, R.B., et al., "Association between interleukin-8 concentration in nasal secretions and severity of symptoms of experimental rhinovirus colds," *Clin. Infec. Dis.*, 1998, 26, 840-846.

Wolfe, J.P., et al. "An improved catalyst system for aromatic carbon—nitrogen bond formation: the possible involvement of bis(phosphine) palladium complexes as key intermediates," *J. Am. Chem. Soc.*, 1996, 118, 7215-7216.

Wolfe, J.P., et al., "Nickel-catalyzed amination of aryl chlorides," *J. Am. Chem. Soc.*, 1997, 119, 6054-6058.

Wolfe, J.P., et al., "Room temperature catalytic amination of aryl iodides," *J. Org. Chem.*, 1997, 62, 6066-6068.

Wolfe, J.P., et al., "Improved functional group complatibility in the palladium-catalyzed amination of aryl bromides," *Tetrah. Lett.*, 1997, 38(36), 6359-6362.

Zhu, Z., et al., "Rhinovirus stimulation of interleukin-6 in vivo and in vitro, evicence for nuclear factor kB-dependent transcriptional activation," *J. of Clin. Invest.*, 1996, 97(2), 421-430.

\* cited by examiner

PYRIDINE AND PYRIMIDINE DERIVATIVES

This application is a 371 of PCT/GB02/05196 file Nov. 20, 2002.

This invention relates to a series of pyridine and pyrimidine derivatives, to compositions containing them, to processes for their preparation and to their use in medicine.

Immune and inflammatory responses involve a variety of cell types with control and co-ordination of the various interactions occurring via both cell-cell contacts (e.g integrin interactions with their receptors) and by way of intercellular signalling molecules. A large number of different signalling molecules are involved including cytokines, lymphocytes, chemokines and growth factors.

Cells respond to such intercellular signalling molecules by means of intracellular signalling mechanisms that include protein kinases, phosphatases and phospholipases. There are five classes of protein kinase of which the major ones are the tyrosine kinases and the serine/threonine kinases [Hunter, T., Methods in Enzymology (Protein Kinase Classification) p. 3, Hunter, T. and Sefton, B. M.; eds. Vol. 200, Academic Press; San Diego, 1991].

One sub-class of serine/threonine kinases is the mitogen activating protein (MAP) kinases of which there are at least three families which differ in the sequence and size of the activation loop [Adams, J. L. et al, Progress in Medicinal Chemistry p. 1-60, King, F. D. and Oxford, A. W.; eds. vol 38, Elsevier Science, 2001]: the extracellular regulated kinases (ERKs), the c-Jun $NH_2$ terminal kinases or stress activated kinases (JNKs or SAP kinases) and the p38 kinases which have a threonine-glycine-tyrosine (TGY) activation motif. Both the JNKs and p38 MAP kinases are primarily activated by stress stimuli including, but not limited to, proinflammatory cytokines e.g. tumour nucrosis factor (TNF) and interleukin-1 (IL-1), ultraviolet light, endotoxin and chemical or osmotic shock.

Four isoforms of p38 have been described (p38α/β/γ/δ). The human p38α enzyme was initially identified as a target of cytokine-suppressive anti-inflammatory drugs (CSAIDs) and the two isoenzymes found were initially termed CSAID binding protein-1 (CSBP-1) and CSBP-2 [Lee, J. C. et al, Nature (London) 1994, 372, 739-46]. CSBP-2 is now widely referred to as p38α and differs from CSBP-1 in an internal sequence of 25 amino acids as a result of differential splicing of two exons that are conserved in both mouse and human [McDonnell, P. C. et al, Genomics 1995, 29, 301-2]. CSBP-1 and p38α are expressed ubiquitously and there is no difference between the two isoforms with respect to tissue distribution, activation profile, substrate preference or CSAID binding. A second isoform is p38β which has 70% identity with p38α. A second form of p38β termed p38β2 is also known and of the two this is believed to be the major form. p38α and p38β2 are expressed in many different tissues. However in monocytes and macrophages p38α is the predominant kinase activity [Lee, J. C., ibid; Jing, Y. et al, J. Biol. Chem. 1996, 271, 10531-34; Hale, K. K. et al, J. Immun. 1999, 162, 4246-52]. p38γ and p38δ (also termed SAP kinase-3 and SAP kinase-4 respectively) have ~63% and ~61% homology to p38α respectively. p38γ is predominantly expressed in skeletal muscle whilst p38δ is found in testes, pancreas, prostate, small intestine and in certain endocrine tissues.

All p38 homologues and splice variants contain a 12 amino acid activation loop that includes a Thr-Gly-Tyr motif. Dual phosphorylation of both Thr-180 and Tyr-182 in the TGY motif by a dual specificity upstream kinase is essential for the activation of p38 and results in a >1000-fold increase in specific activity of these enzymes [Doza, Y. N. et al FEBS Lett., 1995, 364, 7095-8012]. This dual phosphorylation is effected by MKK6 and under certain conditions the related enzyme MKK3 (see FIG. 1) [Enslen, H. et al J. Biol. Chem., 1998, 273, 1741-48]. MKK3 and MKK6 belong to a family of enzymes termed MAPKK (mitogen activating protein kinase kinase) which are in turn activated by MAPKKK (mitogen activating kinase kinase kinase) otherwise known as MAP3K.

Several MAP3Ks have been identified that are activated by a wide variety of stimuli including environmental stress, inflammatory cytokines and other factors. MEKK4/MTK1 (MAP or ERK kinase kinase/MAP three kinase-1), ASK1 (apoptosis stimulated kinase) and TAK1 (TGF-β-activated kinase) are some of the enzymes identified as upstream activators of for MAPKKs. MEKK4/MTK1 is thought to be activated by several GADD-45-like genes that are induced in response to environmental stimuli and which eventually lead to p38 activation [Takekawa, M. and Saito, H. Cell, 1998, 95, 521-30]. TAK1 has been shown to activate MKK6 in response to transforming growth factor-β (TGF-β). TNF-stimulated activation of p38 is believed to be mediated by the recruitment of TRAF2 [TNF receptor associated factor] and the Fas adaptor protein, Daxx, which results in the activation of ASK1 and subsequently p38.

Several substrates of p38 have been identified including other kinases [e.g. MAPK activated protein kinase 2/3/5 (MAPKAP 2/3/5), p38 regulated/activated protein kinase (PRAK), MAP kinase-interacting kinase 1/2 (MNK1/2), mitogen- and stress-activated protein kinase 1 (MSK1/RLPK) and ribosomal S6 kinase-B (RSK-B)], transcription factors [e.g. activating transcription factor 2/6 (ATF2/6), monocyte-enhancer factor-2A/C (MEF2A/C), C/EBP homologous protein (CHOP), Elk1 and Sap-1a1] and others substrates [e.g. cPLA2, p47phox].

MAPKAP K2 is activated by p38 in response to environmental stress. Mice engineered to lack MAPKAP K2 do not produce TNF in response to lipopolysaccharide (LPS). Production of several other cytokines such as IL-1, IL-6, IFN-g and IL-10 is also partially inhibited [Kotlyarov, A. et al Nature Cell Biol. 1999, 1, 94-7]. Further, MAPKAP K2 from embryonic stem cells from p38α null mice was not activated in response to stress and these cells did not produce IL-6 in response to IL-1 [Allen, M. et al, J. Exp. Med. 2000, 191, 859-69]. These results indicate that MAPKAP K2 is not only essential for TNF and IL-1 production but also for signalling induced by cytokines. In addition MAPKAP K2/3 phosphorylate and thus regulate heat shock proteins HSP 25 and HSP 27 which are involved in cytoskeletal reorganization.

Several small molecule inhibitors of p38 have been reported which inhibit IL-1 and TNF synthesis in human monocytes at concentrations in the low μM range [Lee, J. C. et al, Int. J. Immunopharm. 1988, 10, 835] and exhibit activity in animal models which are refractory to cyclooxygenase inhibitors [Lee, J. C. et al, Annals N. Y. Acad. Sci. 1993, 696, 149]. In addition these small molecule inhibitors are known to also decrease the synthesis of a wide variety of pro-inflammatory proteins including IL-6, IL-8, granulocyte/macrophage colony-stimulating factor (GM-CSF) and cyclooxygenase-2 (COX-2). TNF-induced phosphorylation and activation of cytosolic PLA2, TNF-induced expression of VCAM-1 on endothelial cells and IL-1 stimulated synthesis of collagenase and stromelysin are also inhibited by such small molecule inhibitors of p38 [Cohen, P. Trends Cell Biol. 1997, 7, 353-61].

A variety of cells including monocytes and macrophages produce TNF and IL-1. Excessive or unregulated TNF production is implicated in a number of disease states including Crohn's disease, ulcerative colitis, pyresis, rheumatoid arthritis, rheumatoid spondylitis, osteoarthritis, gouty arthritis and other arthritic conditions, toxic shock syndrome, endotoxic shock, sepsis, septic shock, gram negative sepsis, bone resporption diseases, reperfusion injury, graft vs. host reaction, allograft rejection, adult respiratory distress syndrome, chronic pulmonary inflammatory disease, silicosis, pulmonary sarcoisosis, cerebral malaria, scar tissue formation, keloid formation, fever and myalias due to infection, such as influenza, cachexia secondary to acquired immune deficiency syndrome (AIDS), cachexia secondary to infection or malignancy, AIDS or AIDS related complex.

Excessive or unregulated IL-1 production has been implicated in rheumatoid arthritis, osteoarthritis, traumatic arthritis, rubella arthritis, acute synovitis, psoriatic arthritis, cachexia, Reiter's syndrome, endotoxemia, toxic shock syndrome, tuberculosis, atherosclerosis, muscle degeneration, and other acute or chronic inflammatory diseases such as the inflammatory reaction induced by endotoxin or inflammatory bowel disease. In addition IL-1 has been linked to diabetes and pancreatic β cells [Dinarello, C. A. J. Clinical Immunology, 1985, 5, 287-97].

IL-8 is a chemotactic factor produced by various cell types including endothelial cells, mononuclear cells, fibroblasts and keratinocytes. IL-1, TNF and LPS all induce the production of IL-8 by endothelial cells. In vitro IL-8 has been shown to have a number of functions including being a chemoattractant for neutrophils, T-lymphocytes and basophils. IL-8 has also been shown to increase the surface expression of Mac-1 (CD11b/CD18) on neutrophils without de novo protein synthesis which may contribute to increased adhesion of neutrophils to vascular endothelial cells. Many diseases are characterised by massive neutrophil infiltration. Histamine release from basophils (in both atopic and normal individuals) is induced by IL-8 as is lysozomal enzyme release and respiratory burst from neutrophils.

The central role of IL-1 and TNF together with other leukocyte derived cytokines as important and critical inflammatory mediators is well documented. The inhibition of these cytokines has been shown or would be expected to be of benefit in controlling, alleviating or reducing many of these disease states.

The central position that p38 occupies within the cascade of signalling molecules mediating extracellular to intracellular signalling and its influence over not only IL-1, TNF and IL-8 production but also the synthesis and/or action of other pro-inflammatory proteins (e.g. IL-6, GM-CSF, COX-2, collagenase and stromelysin) make it an attractive target for inhibition by small molecule inhibitors with the expectation that such inhibition would be a highly effective mechanism for regulating the excessive and destructive activation of the immune system. Such an expectation is supported by the potent and diverse anti-inflammatory activities described for p38 kinase inhibitors [Adams, ibid; Badger, et al, J. Pharm. Exp. Ther. 1996, 279, 1453-61; Griswold, et al, Pharmacol. Comm., 1996, 7, 323-29].

We have now found a group of compounds which are potent and selective inhibitors of p38 kinase (p38α, β, δ and γ) and the isoforms and splice variants thereof, especially p38α, p38β and p38β2. The compounds are thus of use in medicine, for example in the prophylaxis and treatment of immune or inflammatory disorders as described herein.

SUMMARY OF THE INVENTION

Thus according to one aspect of the invention we provide a compound of formula (1):

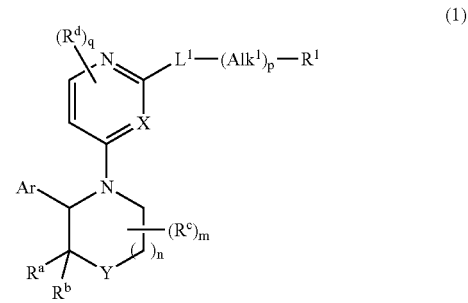

wherein:

$R^a$ and $R^b$ is each independently a hydrogen atom or a group $R^c$, or $R^a$ and $R^b$ together form an oxo (=O) or thio (=S) group;

X is a N atom or an optionally substituted CH group;

Y is a —O— or —S— atom or —SO— or —SO$_2$— group or an optionally substituted —CH$_2$— or —NH— group with the proviso that when $R^a$ and $R^b$ together form an oxo (=O) or thio (=S) group Y is an optionally substituted —CH$_2$— or —NH— group;

$L^1$ is a covalent bond or a linker atom or group;

p is zero or the integer 1;

$Alk^1$ is an optionally substituted $C_{1-10}$aliphatic or $C_{1-10}$heteroaliphatic chain;

$R^1$ is a hydrogen or halogen atom or a —CN, —NO$_2$ or optionally substituted $C_{3-10}$cycloaliphatic, $C_{7-10}$polycycloaliphatic, $C_{2-10}$heterocycloaliphatic, $C_{6-10}$heteropolycycloaliphatic, $C_{6-12}$aromatic or $C_{1-9}$heteroaromatic group, with the proviso that when $L^1$ is a covalent bond and p is zero $R^1$ is other than a hydrogen or halogen atom or a —CN or —NO$_2$ group;

n is zero the integer 1, 2 or 3 with the proviso that when n is zero Y is an optionally substituted —CH$_2$— group;

Ar is an optionally substituted $C_{6-12}$aromatic or $C_{1-9}$heteroaromatic group;

m is zero or the integer 1, 2 or 3;

$R^c$, which may be present on any carbon or, where available, nitrogen atom in the Y-containing ring, is an oxo (=O) or thio (=S) atom or an atom or group —(Alk$^2$)$_r$(R$^5$)$_s$ in which Alk$^2$ is an optionally substituted $C_{1-10}$aliphatic or $C_{1-10}$heteroaliphatic chain, r is zero or the integer 1, s is the integer 1, 2 or 3 and $R^5$ is a hydrogen or halogen atom or a, hydroxyl (—OH), thiol (—SH), cyano (—CN), —CO$_2$R$^2$ (where $R^2$ is a hydrogen atom or an optionally substituted $C_{1-6}$alkyl, $C_{6-12}$aromatic or $C_{1-9}$heteroaromatic group), —OCO$_2$R$^2$, —CONR$^2$R$^3$ (where $R^3$ is a hydrogen atom or an optionally substituted $C_{1-6}$alkyl group or together with the N atom to which they are attached $R^2$ and $R^3$ alkyl groups are joined to form a heterocyclic ring which may be optionally interrupted by a further —O— or —S— atom or —N(R$^2$)— group), —OCONR$^2$R$^3$, —CSNR$^2$R$^3$, nitro (—NO$_2$), amino (—NH$_2$), —NHR$^2$, —N(R$^2$)(R$^3$), —COR$^2$, —OCOR$^2$, —N(R$^3$)COR$^2$, —N(R$^3$)CSR$^2$, —SO$_2$N(R$^2$)(R$^3$), —N(R$^2$)SO$_2$R$^3$, —N(R$^4$)CON(R$^2$)(R$^3$) (where $R^4$ is a hydrogen atom or an optionally substituted $C_{1-6}$alkyl group), —N(R⁴)CSN(R²)(R³), —N(R⁴)SO₂N(R²)(R³), C₃₋₁₀cycloaliphatic, C₂₋₁₀heterocycloaliphatic, C₆₋₁₂aromatic or C₁₋₉heteroaromatic group;

q is zero or the integer 1, 2 or 3;

$R^d$ is a hydrogen or halogen atom or a C₁₋₈alkyl, haloC₁₋₆alkyl, hydroxyl (—OH), C₁₋₆alkoxy, haloC₁₋₆alkoxy, thiol (—SH), C₁₋₆alkylthio, cyano (—CN), —CO₂R⁶ (where R⁶ is a hydrogen atom or an optionally substituted C₁₋₆alkyl group), —OCO₂R⁶, —CONR⁶R⁷ (where R⁷ is a hydrogen atom or an optionally substituted C₁₋₆alkyl group or together with the N atom to which they are attached R⁶ and R⁷ alkyl groups are joined to form a heterocyclic ring which may be optionally interrupted by a further —O— or —S— atom or —N(R⁶)— group), —OCONR⁶R⁷, —CSNR⁶R⁷, nitro (—NO₂), amino(—NH₂), —NHR⁶, —N(R⁶)(R⁷), —COR⁶, —OCOR⁶, —N(R⁷)COR⁶, —N(R⁷)CSR⁶, —SO₂N(R⁶)(R⁷), —N(R⁶)SO₂R⁷, —N(R⁸)CON(R⁶)(R⁷) (where R⁸ is a hydrogen atom or an optionally substituted C₁₋₆alkyl group), —N(R⁸)CSN(R⁶)(R⁷) or —N(R⁸)SO₂N(R⁶)(R⁷) group; and the salts, solvates, hydrates and N-oxides thereof;

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise. In addition, compounds of formula (1) may exist as tautomers, for example keto (CH₂C═O)-enol (CH═CHOH) tautomers. Formula (1) and the formulae hereinafter are intended to represent all individual taulomers and mixtures thereof, unless stated otherwise.

The following general terms as used herein have the stated meaning unless specifically described otherwise.

As used herein the term "C₁₋₆alkyl" whether present as a group or part of a group includes straight or branched C₁₋₆alkyl groups, for example C₁₋₄alkyl groups such as methyl, ethyl, n-propyl, i-propyl, n-butyl, s-butyl, i-butyl or t-butyl groups. Similarly, the terms "alkenyl" or "alkynyl" are intended to mean straight or branched C₂₋₆alkenyl or C₂₋₆alkynyl groups such as C₂₋₄alkenyl or C₂₋₄alkynyl groups. Optional substituents which may be present on these groups include those optional substituents mentioned hereinafter in relation to Alk¹ when Alk¹ is an optionally substituted aliphatic chain.

The term halogen is intended to include fluorine, chlorine, bromine or iodine atoms.

The term "haloalkyl" is intended to include those alkyl groups just mentioned sustituted by one, two or three of the halogen atoms just described. Particular examples of such groups include —CF₃, —CCl₃, —CHF₂, —CHCl₂, —CH₂F and —CH₂Cl groups.

The term "C₁₋₆alkoxy" as used herein is intended to include straight or branched C₁₋₆alkoxy e.g. C₁₋₄alkoxy such as methoxy, ethoxy, n-propoxy, i-propoxy, n-butoxy, s-butoxy, i-butoxy and t-butoxy. "Haloalkoxy" as used herein includes any of these alkoxy groups substituted by one, two or three halogen atoms as described above. Particular examples include —OCF₃, —OCCl₃, —OCHF₂, —OCHCl₂, —OCH₂F and —OCH₂Cl groups.

As used herein the term "C₁₋₆alkylthio" is intended to include straight or branched C₁₋₆alkylthio, e.g. C₁₋₄alkylthio such as methylthio or ethylthio.

As used herein the term "alkylamino or dialkylamino" is intended to include the groups —NHR⁹ and —N(R⁹)₂ [where R⁹ is an optionally substituted straight or branched C₁₋₆alkyl group]. Where two R⁹ groups are present these may be the same or different. In addition where two R⁹ groups are present these may be joined together with the N atom to which they are attached to form an optionally substituted heterocycloalkyl group which may contain a further heteroatom or heteroatom containing group such as an —O— or —S— atom or —N(R⁹)— group. Particular examples of such optionally substituted heterocycloalkyl groups include optionally substituted piperidinyl, pyrazolidinyl, morpholinyl, thiomorpholinyl, pyrrolidinyl, imidazolidinyl and piperazinyl groups. The optional substituents which may be present on such heterocycloalkyl groups include C₁₋₆alkyl groups or those optional substituents as described hereinafter in relation to aliphatic chains.

When Alk¹ is present in compounds of formula (1) as an optionally substituted aliphatic chain it may be an optionally substituted C₁₋₁₀aliphatic chain. Particular examples include optionally substituted straight or branched chain C₁₋₆alkylene, C₂₋₆alkenylene, or C₂₋₆alkynylene chains.

Particular examples of aliphatic chains represented by Alk¹ include optionally substitute a —CH₂—, —CH(CH₃)—, —CH₂CH₂—, —CH(CH₃)CH₂—, —(CH₂)₂CH₂—, —(CH₂)₃CH₂—, —CH(CH₃)(CH₂)₂CH₂—, —CH₂CH(CH₃)CH₂—, —C(CH₃)₂CH₂—, —CH₂C(CH₃)₂CH₂—, —(CH₂)₂CH(CH₃)CH₂—, —CH(CH₃)CH₂CH₂—, —CH(CH₃)CH₂CH(CH₃)CH₂—, —CH₂CH(CH₃)CH₂CH₂—, —(CH₂)₂C(CH₃)₂—, —(CH₂)₄CH₂—, —(CH₂)₅CH₂—, —CHCH—, —CHCHCH₂—, —CH₂CHCH—, —CHCHCH₂CH₂—, —CH₂CHCHCH₂—, —(CH₂)₂CHCH—, —CC—, —CCCH₂—, —CH₂CC—, —CCCH₂CH₂—, —CH₂CCCH₂— or —(CH₂)₂CCH— chains.

Heteroaliphatic chains represented by Alk¹ in the compounds of formula (1) include the aliphatic chains just described but with each additionally containing one, two, three or four heteroatoms or heteroatom-containing groups. Particular heteroatoms or groups include atoms or groups L² where L² is a linker atom or group. Each L² atom or group may interrupt the aliphatic group, or may be positioned at its terminal carbon atom to connect the group to an adjoining atom or group. Particular examples include optionally substituted -L²CH₂—, —CH₂L²-, -L²CH(CH₃)—, —CH(CH₃)L²-, —CH₂L²CH₂—, -L²CH₂CH₂—, -L²CH₂CH(CH₃)—, —CH(CH₃)CH₂L²-, —CH₂L²CH₂—, —CH₂L²CH₂CH₂—, —CH₂L²CH₂CH₂L²-, —(CH₂)₂L²CH₂—, —(CH₂)₃L²CH₂—, -L²(CH₂)₂CH₂—, -L²CH₂CHCH—, —CHCHCH₂L²- and —(CH₂)₂L²CH₂CH₂— chains.

When L² is present in heteroaliphatic chains as a linker atom or group it may be any divalent linking atom or group. Particular examples include —O— or —S— atoms or —C(O)—, —C(O)O—, —OC(O)—, —C(S)—, —S(O)—, —S(O)₂—, —N(R¹⁰)— [where R¹⁰ is a hydrogen atom or a straight or branched C₁₋₆alkyl group], —N(R¹⁰)O—, —N(R¹⁰)N—, —CON(R¹⁰)—, —OC(O)N(R¹⁰)—, —CSN(R¹⁰)—, —N(R¹⁰)CO—, —N(R¹⁰)C(O)O—, —N(R¹⁰)CS—, —S(O)₂N(R¹⁰)—, —N(R¹⁰)S(O)₂—, —N(R¹⁰)CON(R¹⁰)—, —N(R¹⁰)CSN(R¹)— or —N(R¹⁰)SO₂N(R¹⁰)— groups. Where L² contains two R¹⁰ groups these may be the same or different.

The optional substituents which may be present on aliphatic or heteroaliphatic chains represented by Alk¹ include one, two, three or more substituents where each substituent may be the same or different and is selected from halogen atoms, e.g. fluorine, chlorine, bromine or iodine atoms, or —OH, ═CO₂H, —CO₂R¹¹ [where R¹¹ is an optionally substituted straight or branched C₁₋₆alkyl group], e.g. —CO₂CH₃ or —CO₂C(CH₃)₃, —CONHR¹¹, e.g. —CON- HCH$_3$, —CON(R$^{11}$)$_2$, e.g. —CON(CH$_3$)$_2$, —COR$^{11}$, e.g. —COCH$_3$, C$_{1-6}$alkoxy, e.g. methoxy or ethoxy, haloC$_{1-6}$alkoxy, e.g. trifluoromethoxy or difluoromethoxy, thiol (—SH), —S(O)R$^{11}$, e.g. —S(O)CH$_3$, —S(O)$_2$R$^{11}$, e.g. —S(O)$_2$CH$_3$, C$_{1-6}$alkylthio e.g. methylthio or ethylthio, amino, —NHR$^{11}$, e.g. —NHCH$_3$ or —N(R$^{11}$)$_2$, e.g. —N(CH$_3$)$_2$ groups. Where two R$^{11}$ groups are present in any of the above substituents these may be the same or different.

In addition when two R$^{11}$ alkyl groups are present in any of the optional substituents just described these groups may be joined, together with the N atom to which they are attached, to form a heterocyclic ring as hereinbefore defined when two R$^9$ groups are so joined.

When L$^1$ is present in compounds of formula (1) as a linker atom or group it may be any such atom or group as hereinbefore described in relation to L$^2$ linker atoms and groups.

Optionally substituted cycloaliphatic groups represented by the group R$^1$ in compounds of the invention include optionally substituted C$_{3-10}$cycloaliphatic groups. Particular examples include optionally substituted C$_{3-10}$cycloalkyl, e.g. C$_{3-7}$cycloalkyl or C$_{3-10}$cycloalkenyl, e.g C$_{3-7}$cycloalkenyl groups.

Optionally substituted heterocycloaliphatic group represented by the group R$^1$ include optionally substituted C$_{2-10}$heterocycloaliphatic group. Particular examples include optionally substituted C$_{2-10}$heterocycloalkyl, e.g. C$_{2-7}$heterocycloalkyl or C$_{2-10}$heterocycloalkenyl, e.g. C$_{2-7}$heterocycloalkenyl groups, each of said groups containing one, two, three or four heteroatoms or heteroatom containing groups L$^3$ in place of or in addition to the ring carbon atoms where L$^3$ is an atom or group as previously defined for L$^2$.

Optionally substituted polycycloaliphatic groups represented by the group R$^1$ include optionally substituted C$_{7-10}$bi-or tricycloalkyl or C$_{7-10}$bi- or tricycloalkenyl groups. Optionally substituted heteropolycycloaliphatic groups represented by the group R$^1$ include optionally substituted C$_{6-10}$bi- or tricycloalkyl or C$_{6-10}$bi- or tri-cycloalkenyl groups containing one, two, three, four or more L$^3$ atoms or groups in place of or in addition to the ring carbon atoms.

Particular examples of cycloaliphatic, polycycloaliphatic, heterocycloaliphatic and heteropolycycloaliphatic groups represented by the group R$^1$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, oxiranyl, oxetanyl, aziridinyl, azetidinyl, dihydrofuranyl, tetrahydrofuranyl, tetrahydropyranyl, dihydrothiophenyl, tetrahydrothiophenyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, 5,6-dihydro-2(1H)-pyrazinone, tetrahydropyrimidinyl, thiazolinyl, thiazolidinyl, pyranyl, e.g. 2- or 4-pyranyl, piperidinyl, homopiperidinyl, heptamethyleneiminyl, piperidinone, 1,4-dioxanyl, morpholinyl, morpholinone, 1,4-dithianyl, thiomorpholinyl, piperazinyl, homopiperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, 1,3,5-oxadiazinyl, dihydroisothiazolyl, dihydroisothiazole 1,1-dioxide , e.g. 2,3-dihydroisothiazole 1,1-dioxide, dihydropyrazinyl and tetrahydropyrazinyl groups.

The optional substituents which may be present on the cycloaliphatic, polycycloaliphatic, heterocycloaliphatic or heteropolycycloaliphatic groups represented by the group R$^1$ include one, two, three or more substituents selected from halogen atoms, or C$_{1-6}$alkyl, e.g. methyl or ethyl, haloC$_{1-6}$alkyl, e.g. halomethyl or haloethyl such as difluoromethyl or trifluoromethyl, optionally substituted by hydroxyl, e.g. —C(OH)(CF$_3$)$_2$, C$_{1-6}$alkoxy, e.g. methoxy or ethoxy, haloC$_{1-6}$alkoxy, eg. halomethoxy or haloethoxy such as difluoromethoxy or trifluoromethoxy, thiol, C$_{1-6}$alkylthiol, e.g. methylthiol or ethylthiol, carbonyl (═O), thiocarbonyl (═S), imino (═NR$^{12}$) [where R$^{12}$ is an —OH group or a C$_{1-6}$alkyl group], or —(Alk$^3$)$_v$R$^{13}$ groups in which Alk$^3$ is a straight or branched C$_{1-3}$alkylene chain, v is zero or the integer 1 and R$^{13}$ is a C$_{3-8}$cycloalkyl, —OH, —SH, —N(R$^{14}$)(R$^{15}$) [in which R$^{14}$ and R$^{15}$ is each independently selected from a hydrogen atom or an optionally substituted C$_{1-6}$alkyl or C$_{3-8}$cycloalkyl group, or together with the N atom to which they are attached R$^{14}$ and R$^{15}$ alkyl groups are joined to form a heterocyclic ring which may be optionally interrupted by a further —O— or —S— atom or —N(R$^{14}$)— group as hereinbefore defined when two R$^9$ groups are joined to form a heterocyclic ring], —OR$^{14}$, —SR$^{14}$, —CN, —NO$_2$, —CO$_2$R$^{14}$, —SOR$^{14}$, —SO$_2$R$^{14}$, —SO$_3$R$^{14}$, —OCO$_2$R$^{14}$, —C(O)R$^{14}$, —OC(O)R$^{14}$, —C(S)R$^{14}$, —C(O)N(R$^{14}$)(R$^{15}$), —OC(O)N(R$^{14}$)(R$^{15}$), —N(R$^{14}$)C(O)R$^{15}$, —C(S)N(R$^{14}$)(R$^{15}$), —N(R$^{14}$)C(S)R$^{15}$, —SO$_2$N(R$^{14}$)(R$^{15}$), —N(R$^{14}$)SO$_2$R$^{15}$, —N(R$^{16}$)C(O)N(R$^{14}$)(R$^{15}$) [where R$^{16}$ is a hydrogen atom or a C$_{1-6}$alkyl group], —N(R$^{16}$)C(S)N(R$^{14}$)(R$^{15}$), —N(R$^{16}$)SO$_2$N(R$^{14}$)(R$^{15}$) or an optionally substituted C$_{6-12}$aromatic or C$_{1-9}$heteroaromatic group.

Particular examples of Alk$^3$ chains include —CH$_2$—, —CH$_2$CH$_2$—, —CH$_2$CH$_2$CH$_2$—, —CH$_2$CH(CH$_3$)—, and —CH(CH$_3$)CH$_2$— chains.

When R$^{13}$, R$^{14}$ and/or R$^{15}$ is present as a C$_{3-8}$cycloalkyl groups it may be for example a cyclopropyl, cyclobutyl, cyclopentyl or cyclohexyl group. Optional substituents which may be present on such groups include for example one, two or three substituents which may be the same or different selected from halogen atoms, for example fluorine, chlorine, bromine or iodine atoms, or hydroxy or C$_{1-6}$alkoxy, e.g. methoxy, ethoxy or i-propoxy groups.

When R$^2$ and R$^3$, R$^6$ and R$^7$ or R$^{14}$ and R$^{15}$ are each alkyl groups joined together with the N atom to which they are attached to form a heterocyclic ring they may be any such ring as hereinbefore described when two R$^9$ alkyl groups are so joined.

When R$^5$ is an optionally substituted C$_{6-12}$aromatic or C$_{1-9}$heteroaromatic group it may be any such group as described hereinafter in relation to R$^1$.

Additionally, when the group R$^1$ is a heterocycloaliphatic or heteropolycycloaliphatic group containing one or more nitrogen atoms each nitrogen atom may be optionally substituted by a group -L$^4$(Alk$^4$)$_h$R$^{17}$ in which L$^4$ is a covalent bond or a —C(O)—, —C(O)O—, —C(S)—, —S(O)$_2$—, —CON(R$^{10}$)— or —SO$_2$N(R$^{10}$)— group; Alk$^4$ is an optionally substituted aliphatic or heteroaliphatic chain; h is zero or the integer 1; and R$^{17}$ is a hydrogen atom or an optionally substituted cycloaliphatic, heterocycloaliphatic, polycycloaliphatic, heteropolycycloaliphatic, aromatic or heteroaromatic group as herein described in relation to R$^1$.

When Alk$^4$ is present as an aliphatic or heteroaliphatic chain it may be for example any aliphatic or heteroaliphatic chain as hereinbefore described for Alk$^1$.

Optionally substituted aromatic groups represented by the groups R$^1$ include for example monocyclic or bicyclic fused ring C$_{6-12}$aromatic groups, such as phenyl, 1- or 2-napthyl, 1- or 2-tetrahydronapthyl, indanyl or indenyl groups.

Heteroaromatic groups represented by the groups $R^1$ include for example $C_{1-9}$heteroaromatic groups containing for example one, two, three or four heteroatoms selected from oxygen, sulphur or nitrogen atoms. In general, the heteroaromatic groups may be for example monocyclic or bicyclic fused-ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N-$C_{1-6}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,5-oxadiazolyl, 1,3,4-oxadiazolyl, 1,3,4-thiadiazolyl, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, benzothienyl, [2,3-dihydro]benzothienyl, benzotriazolyl, indolyl, indolinyl, indazolinyl, benzimidazolyl, imidazo[1,2-a]pyridyl, benzothiazolyl, benzoxazolyl, benzisoxazolyl, benzopyranyl, [3,4-dihydro]benzopyranyl, quinazolinyl, quinoxalinyl, naphthyridinyl, imidazo[1,5-a]pyridinyl, imidazo[1,5-a]pyrazinyl, imidazo[1,5-c]pyrimidinyl, pyrido[3,4-b]pyridyl, pyrido[3,2-b]pyridyl, pyrido[4,3-b]pyridyl, quinolinyl, isoquinolinyl, phthalazinyl, tetrazolyl, 5,6,7,8-tetrahydroquinolinyl, 5,6,7,8-tetrahydroisoquinolinyl, imidyl, e.g. succinimidyl, phthalimidyl or naphthalimidyl such as 1,8-naphthalimidyl, pyrazolo[4,3-d]pyrimidinyl, furo[3,2-d]pyrimidinyl, thieno[3,2-d]pyrimidinyl, pyrrolo[3,2-d]pyrimidinyl, pyrazolo[3,2-b]pyridinyl, furo[3,2-b]pyridinyl, thieno[3,2-b]pyridinyl, pyrrolo[3,2-b]pyridinyl, thiazolo[3,2-a]pyridinyl, pyrido[1,2-a]pyrimidinyl, tetrahydroimidazo[1,2-a]pyrimidinyl and dihydroimidazo[1,2-a]pyrimidinyl groups.

Optional substituents which may be present on aromatic or heteroaromatic groups represented by the group $R^1$ include one, two, three or more substituents, each selected from an atom or group $R^{18}$ in which $R^{18}$ is $R^{18a}$ or -$L^5(Alk^5)_f(R^{18a})_g$, where $R^{18a}$ is a halogen atom, or an amino (—$NH_2$), substituted amino, nitro, cyano, hydroxyl (—OH), substituted hydroxyl, formyl, carboxyl (—$CO_2H$), esterified carboxyl, thiol (—SH), substituted thiol, —$COR^{19}$ [where $R^{19}$ is an -$L^5(Alk^5)_f(R^{18a})_g$, aryl or heteroaryl group], —$CSR^{19}$, —$SO_3H$, —$SOR^{19}$, —$SO_2R^{19}$, —$SO_3R^{19}$, —$SO_2NH_2$, —$SO_2NHR^{19}$, —$SO_2N(R^{19})_2$, —$CONH_2$, —$CSNH_2$, —$CONHR^{19}$, —$CSNHR^{19}$, —$CON(R^{19})_2$, —$CSN(R^{19})_2$, —$N(R^{20})SO_2R^{19}$ [where $R^{20}$ is a hydrogen atom or a straight or branched $C_{1-6}$alkyl group], —$N(SO_2R^{19})_2$, —$N(R^{20})SO_2NH_2$, —$N(R^{20})SO_2NHR^{19}$, —$N(R^{20})SO_2N(R^{19})_2$, —$N(R^{20})COR^{19}$, —$N(R^{20})CONH_2$, —$N(R^{20})CONHR^{19}$, —$N(R^{20})CON(R^{19})_2$, —$N(R^{20})CSNH_2$, —$N(R^{20})CSNHR^{19}$, —$N(R^2)CSN(R^{19})_2$, —$N(R^{20})CSR^{19}$, —$N(R^{20})C(O)OR^{19}$, —$SO_2NHet^1$ [where —$NHet^1$ is an optionally substituted $C_{5-7}$cyclicamino group optionally containing one or more other —O— or —S— atoms or —$N(R^{20})$—, —C(O)— or —C(S)— groups], —$CONHet^1$, —$CSNHet^1$, —$N(R^{20})SO_2NHet^1$, —$N(R^{20})CONHet^1$, —$N(R^{20})CSNHet^1$, —$SO_2N(R^{20})Het$ [where -Het is an optionally substituted monocyclic $C_{5-7}$carbocyclic group optionally containing one or more other —O— or —S— atoms or —$N(R^{20})$—, —C(O)—, —S(O)— or —S(O)$_2$— groups], -Het, —$CON(R^{20})Het$, —$CSN(R^{20})Het$, —$N(R^{20})CON(R^{20})Het$, —$N(R^{20})CSN(R^{20})Het$, —$N(R^{20})SO_2N(R^{20})Het$, aryl or heteroaryl groups; $L^5$ is a covalent bond or a linker atom or group as hereinbefore defined for $L^2$; f is zero or the integer 1; $Alk^5$ is an optionally substituted straight or branched $C_{1-6}$alkylene, $C_{2-6}$alkenylene or $C_{2-6}$alkynylene chain, optionally interrupted by one, two or three —O— or —S— atoms or —S(O)$_n$— [where n is an integer 1 or 2] or —$N(R^{20})$— e.g. —$N(CH_3)$— groups; and g is zero or the integer 1, 2, or 3. It will be appreciated that when two $R^{19}$ or $R^{20}$ groups are present in one of the above substituents the $R^{19}$ and/or $R^{20}$ groups may be the same or different.

When in the group -$L^5Alk^5(R^{18a})_g$ g is an integer 1, 2 or 3, it is to be understood is that the substituent or substituents $R^{18a}$ may be present on any suitable carbon atom in -$Alk^5$. Where more than one $R^{18a}$ substituent is present these may be the same or different and may be present on the same or different atom in -$Alk^5$. Clearly, when g is zero and no substituent $R^{18a}$ is present the alkylene, alkenylene or alkynylene chain represented by $Alk^5$ becomes an alkyl, alkenyl or alkynyl group.

When $R^{18a}$ is a substituted amino group it may be for example a group —$NHR^9$ [where $R^9$ is as defined above] or a group —$N(R)_2$ wherein each $R^9$ group is the same or different.

When $R^{18a}$ is a halogen atom it may be for example a fluorine, chlorine, bromine, or iodine atom.

When $R^{18a}$ is a substituted hydroxyl or substituted thiol group it may be for example a group —$OR^{19}$ or a $R^{19}$ group respectively.

Esterified carboxyl groups represented by the group $R^{18a}$ include groups of formula —$CO_2Alk^6$ wherein $Alk^6$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^6$ group include $R^{10a}$ atoms and groups as described above.

When $Alk^5$ is present in or as a substituent it may be for example a —$CH_2$—, —$CH(CH_3)$—, —$C(CH_3)_2$—, —$CH_2CH_2$—, —$CH_2CH_2CH_2$—, —$CH(CH_3)CH_2$—, —$CH_2CH_2CH_2CH_2$—, —$CH_2CH(CH_3)CH_2$—, —$CH(CH_3)CH_2CH_2$—, —$C(CH_3)_2CH_2$—, —CH=CH—, —CH=$CCH_2$—, —$CH_2$C=CH—, —CH=$CHCH_2CH_2$—, —$CH_2$CH=$CHCH_2$—, —$CH_2CH_2$CH=$CH_2$—, —CC—, —$CCCH_2$—, —$CH_2$CC—, —$CCCH_2CH_2$—, —$CH_2$CCCH$_2$— or —$CH_2CH_2$CC— chain, optionally interrupted by one, two, or three —O— or —S—, atoms or —S(O)—, —S(O)$_2$— or —$N(R^{20})$—, e.g. —$N(CH_3)$— groups. The aliphatic chains represented by $Alk^5$ may be optionally substituted by one, two or three halogen atoms in addition to any $R^{18a}$ groups that may be present.

Aryl or heteroaryl groups represented by the groups $R^{18a}$ or $R^{19}$ include mono- or bicyclic optionally substituted $C_{6-12}$aromatic or $C_{1-9}$heteroaromatic groups as described hereinbefore for the group $R^1$. The aromatic and heteroaromatic groups may be attached to the group $R^1$ in compounds of formula (1) by any carbon or hetero e.g. nitrogen atom as appropriate.

It will be appreciated that when —NHet$^1$ or -Het forms part of a substituent R$^{18}$ the heteroatoms or heteroatom containing groups that may be present within the ring —NHet$^1$ or -Het take the place of carbon atoms within the parent carbocyclic ring.

Thus when —NHet$^1$ or -Het forms part of a substituent R$^{18a}$ each may be for example an optionally substituted pyrrolidinyl, imidazolidinyl, pyrazolidinyl, piperazinyl, morpholinyl, thiomorpholinyl, piperidinyl or thiazolidinyl group. Additionally -Het may represent for example, an optionally substituted cyclopentyl or cyclohexyl group. Optional substituents which may be present on —NHet$^1$ or -Het include those substituents described above when R$^1$ is a heterocycloaliphatic group.

Particularly useful atoms or groups represented by R$^{18}$ include fluorine, chlorine, bromine or iodine atoms, or C$_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, or thienyl, C$_{1-6}$hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxy-propylthio, C$_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{3-7}$cycloalkyl, e.g. cyclobutyl, cyclopentyl, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino, ethylamino, —CH(CH$_3$)NH$_2$ or —C(CH$_3$)$_2$NH$_2$, haloC$_{1-6}$alkylamino, e.g. fluoroC$_{1-6}$alkylamino,e.g. —CH(CF$_3$)NH$_2$ or —(CF$_3$)$_2$NH$_2$, amino (—NH$_2$), aminoC$_{1-6}$alkyl, e.g. aminomethyl or aminoethyl, C$_{1-6}$dialkylamino, e.g. dimethylamino or diethylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy, diisopropylaminoethoxy, or dimethylaminopropoxy, imido, such as phthalimido or naphthalimido, e.g. 1,8-naphthalimido, nitro, cyano, hydroxyl (—OH), formyl [HC(O)—], carboxyl (—CO$_2$H), —CO$_2$Alk$^6$ [where Alk$^6$ is as defined above], C$_{1-6}$ alkanoyl e.g. acetyl, optionally substituted benzoyl, thiol (—SH), thioC$_{1-6}$alkyl, e.g. thiomethyl or thioethyl, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, aminoC$_{1-6}$alkylaminocarbonyl, e.g. aminoethylamino-carbonyl, C$_{1-6}$dialkylaminoC$_{1-6}$alkylaminocarbonyl, e.g. diethylaminoethylaminocarbonyl, aminocarbonylamino, C$_{1-6}$alkylaminocarbonyl-amino, e.g. methylaminocarbonylamino or ethylaminocarbonylamino, C$_{1-6}$dialkylaminocarbonylamino, e.g. dimethylaminocarbonylamino or diethylaminocarbonylamino, C$_{1-6}$alkylaminocabonylC$_{1-6}$alkylamino, e.g. methylaminocarbonylmethylamino, aminothiocarbonylamino, C$_{1-6}$alkylaminothiocarbonylamino, e.g. methylaminothiocarbonylamino or ethylaminothiocarbonylamino, C$_{1-6}$dialkylaminothiocarbonylamino, e.g. dimethylaminothiocarbonylamino or diethylaminothiocarbonylamino, C$_{1-6}$alkylaminothiocarbonylC$_{1-6}$alkylamino, e.g. ethylaminothiocarbonylmethylamino, —CONHC(=NH)NH$_2$, C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, optionally substituted phenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, optionally substituted morpholinesulphonylamino or morpholinesulphonylC$_{1-6}$alkylamino, optionally substituted phenylaminosulphonylamino, C$_{1-6}$alkanoylamino, e.g. acetylamino, aminoC$_{1-6}$alkanoylamino e.g. aminoacetylamino, C$_{1-6}$dialkylaminoC$_{1-6}$alkanoylamino, e.g. dimethylaminoacetylamino, C$_{1-6}$alkanoylaminoC$_{1-6}$alkyl, e.g. acetylaminomethyl, C$_{1-6}$alkanoylaminoC$_{1-6}$alkylamino, e.g. acetamidoethylamino, C$_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylaminoC$_{1-6}$alkyl e.g. benzyloxycarbonylaminoethyl, benzothio, pyridylmethylthio or thiazolylmethylthio groups.

A further particularly useful group of substituents represented by R$^{18}$ when present on aromatic or heteroaromatic groups includes substituents of formula -L$^5$Alk$^6$R$^{18a}$ where L$^5$ is preferably a covalent bond or an —O— or —S— atom or —N(R$^{10}$)—, —C(O)—, —C(O)O—, —O—C(O)—, —N(R$^{10}$)CO—, —CON(R$^2$)— or —N(R$^{10}$)S(O)$_2$— group, Alk$^6$ is an optionally substituted C$_{1-6}$alkyl group optionally interrupted by one or two —O— or —S— atoms or —N(R$^{20}$)—, —C(O)—, —C(S)—, —CON(R$^{20}$)— or —N(R$^{20}$)CO— groups and R$^{18a}$ is an optionally substituted Het group as herein defined or an optionally substituted C$_{1-9}$heteroaromatic group as hereinbefore described in relation to R$^1$.

Where desired, two R$^{18}$ substituents may be linked together to form a cyclic group such as a cyclic ether, e.g. a C$_{1-6}$alkylenedioxy group such as methylenedioxy or ethylenedioxy.

It will be appreciated that where two or more R$^{18}$ substituents are present, these need not necessarily be the same atoms and/or groups. In general, the substituent(s) may be present at any available ring position on the aromatic or heteroaromatic group represented by the group R$^1$.

When Ar is present in compounds of formulae (1) as an optionally substituted aromatic or heteroaromatic group it may be any such group as hereinbefore described for R$^1$. Optional substituents which may be present include those R$^{18}$ atoms and groups as described in relation to R$^1$ aromatic and heteroaromatic groups.

When in compounds of formula (1) Y is an optionally substituted —CH$_2$— or —NH— group the substituents which may be present on the N or C atom in place of hydrogen atoms include those R$^c$ atoms and groups as herein defined.

When Alk$^2$ is present in a substituent R$^c$ as an optionally substituted C$_{1-10}$aliphatic or C$_{1-10}$heteroaliphatic chain it may be any such chain as hereinbefore defined for Alk$^1$.

When R$^5$ is present in a substituent R$^c$ as an optionally substituted C$_{3-10}$cycloaliphatic, C$_{2-10}$heterocycloaliphatic, C$_{6-12}$aromatic or C$_{1-9}$heteroaromatic group it may be any such group as hereinbefore defined for R$^1$.

When R$^2$ is present in a substituent R$^c$ as an optionally substituted C$_{6-12}$aromatic or C$_{1-9}$heteroaromatic group it may be any such group as hereinbefore defined for R$^1$.

When in compounds of formula (1) X is an optionally substituted —CH— group the substituents which may be present on the C atom in place of the hydrogen atom include those $R^d$ atoms and groups as herein defined.

One useful group of compounds according to the invention is that where $R^a$ and $R^b$ is each independently a hydrogen atom or together form an oxo (=O) or thio (=S) group most preferably an oxo group.

An especially useful group of compounds according to the invention has the formula (2):

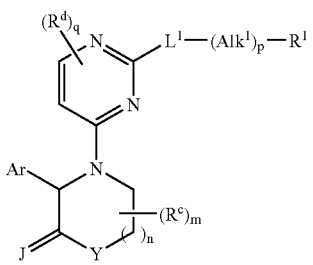

(2)

in which

J is an oxygen or sulphur atom;

Y is an optionally substituted —CH$_2$— or —NH— group;

$R^1$, Alk$^1$, p, $L^1$, Ar, $R^c$, m, $R^d$, q and n are as generally and specifically defined previously;

and the salts, solvates, hydrates and N-oxides thereof.

In compounds of formula (2) Y is an optionally substituted —CH$_2$— or —NH— group. In one preferred group of compounds of formula (2) Y is an optionally substituted —NH— group where preferred optional substituents are straight or branched C$_{1-4}$alkyl groups, especially —CH$_3$, CH$_2$CH$_3$, —CH$_2$CH$_2$CH$_3$ or —CH(CH$_3$)$_2$ groups. Most preferably Y is a —NH— group.

In one preferred class of compounds of formula (1) and (2) n is the integer 1.

In a preferred class of compounds of formula (2) J is an oxygen atom. In compounds of this type, Y is preferably a —NH— or —N(CH$_3$)— group.

In compounds of formula (2) and in general in compounds of the invention $L^1$ is preferably a covalent bond or an —O— or —S— atom or an —N(R$^{10}$)—, especially —NH— or —N(CH$_3$)—, —C(O)—, —C(S)—, —S(O)— or —S(O)$_2$— group and is especially a covalent bond or an —O— or —S— atom or —NH— group. In particular $L^1$ is a —NH— group in compounds of the invention.

In one preferred class of compounds of the invention p is zero.

In another preferred class of compounds of the invention p is the integer 1 and Alk$^1$ is preferably an optionally substituted C$_{1-6}$alkylene chain, especially a —CH$_2$—, —CH(CH$_3$)—, —C(CH$_3$)$_2$—, —CH$_2$CH$_2$—, —CH$_2$CH$_2$CH$_2$—, —CH(CH$_3$)CH$_2$— or —CH$_2$CH(CH$_3$)— chain, most especially a —CH$_2$—, —CH(CH$_3$)— or —C(CH$_3$)$_2$— chain.

In compounds of formula (2) and in general in compounds of the invention $R^1$ is preferably a hydrogen atom or an optionally substituted C$_{3-10}$cycloaliphatic, C$_{2-10}$heterocycloaliphatic, C$_{6-12}$aromatic or C$_{1-9}$heteroaromatic group.

Particularly preferred $R^1$ optionally substituted cycloaliphatic groups include optionally substituted C$_{3-7}$cycloalkyl groups, especially cyclopropyl, cyclobutyl, cyclopentyl or cyclohexyl groups. Particularly preferred optional substituents which may be present on such groups include halogen atoms, especially fluorine, chlorine or bromine atoms, or C$_{1-6}$alkyl groups, especially C$_{1-4}$alkyl groups, most especially a methyl group, or a haloC$_{1-6}$alkyl group, especially a fluoroC$_{1-6}$alkyl group, most especially a —CF$_3$ group, or a C$_{1-6}$alkoxy, especially methoxy, ethoxy, propxy or i-propoxy group, or a haloC$_{1-6}$alkoxy, especially a fluoroC$_{1-6}$alkoxy, most especially a OCF$_3$ group, or a cyano (—CN), nitro (—NO$_2$), substituted amino, especially —NHCH$_3$ or —N(CH$_3$)$_2$, — or COR$^{11}$, especially —COCH$_3$, group.

Particularly preferred $R^1$ optionally substituted heterocycloaliphatic groups include optionally substituted C$_{2-7}$heterocycloalkyl groups containing one or two —O— or —S— atoms or —N(R$^{10}$)— groups, especially tetrahydrofuranyl, tetrahydropyranyl, imidazolidinyl, piperidinyl, morpholinyl, thiomorpholinyl, or piperazinyl groups. Optional substituents which may be present on such groups include those optional substituents as just described in relation to preferred $R^1$ cycloaliphatic groups.

Particularly preferred $R^1$ aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl or triazinyl group.

Particularly preferred optional substituents which may be present on $R^1$ aromatic or heteroaromatic groups include atoms or groups —R$^{18a}$ or -L$^5$Alk$^5$(R$^{18a}$)$_g$ as hereinbefore defined. Particularly useful optional substituents include halogen atoms, especially fluorine, chlorine or bromine atoms, or C$_{1-6}$alkyl groups, especially C$_{1-4}$alkyl groups, most especially a methyl group, or haloC$_{1-6}$alkyl groups, especially a fluoroC$_{1-6}$alkyl group, most especially a —CF$_3$ group, or C$_{1-6}$alkoxy, especially methoxy, ethoxy, propxy or i-propoxy groups, or haloC$_{1-6}$alkoxy, especially fluoroC$_{1-6}$alkoxy, most especially —OCF$_3$ groups, or cyano (—CN), esterified carboxyl, especially —CO$_2$CH$_3$ or —CO$_2$C(CH$_3$)$_3$, nitro (—NO$_2$), amino (—NH$_2$), substituted amino, especially —NHCH$_3$ or —N(CH$_3$)$_2$, —COR$^{19}$, especially —COCH$_3$, or —N(R$^{20}$)COR$^{19}$, especially —NHCOCH$_3$ groups.

In one particularly preferred class of compounds of formula (1) and (2) $L^1$ is a covalent bond. In this group of compounds p is preferably zero and $R^1$ is preferably an optionally substituted C$_{2-7}$heterocycloalkyl group as just defined, especially a N atom containing C$_{2-7}$heterocycloalkyl group, most preferably a piperidinyl, morpholinyl, thiomorpholinyl or piperidinyl group, especially linked via a ring N atom to the remainder of the compound of formula (1) or (2). Optional substituents which may be present on such groups include those substituents as just described for preferred $R^1$ cycloaliphatic groups.

In another particularly preferred class of compounds of formula (1) and (2) $L^1$ is a preferred atom or group as just described, especially an —O— or —S— atom or —N(R$^{10}$)—, especially —NH— group. In one preferred group of compounds of this class p is the integer 1 and Alk$^1$ is preferably an optionally substituted C$_{1-6}$alkylene chain as just described. In this group of compounds $R^1$ is preferably a hydrogen atom. In another preferred group of compounds of this class p is the integer 1 and Alk$^1$ is preferably an optionally substituted C$_{1-3}$alkylene chain, where the preferred optional substituents are those just described for Alk$^1$. Most preferably Alk$^1$ is a —CH$_2$—, —CH(CH$_3$)—, —C(CH$_3$)$_2$—, —CH$_2$CH$_2$—, —CH$_2$CH$_2$CH$_2$—, —CH (CH$_3$)CH$_2$— or —CH$_2$CH(CH$_3$)— chain. In this class of compounds R$^1$ is preferably an optionally substituted C$_{3-10}$cycloaliphatic, C$_{2-10}$heterocycloaliphatic, C$_{6-12}$aromatic or C$_{1-9}$heteroaromatic group as herein generally and particularly described. In this class of compounds R$^1$ is most preferably an optionally substituted C$_{6-12}$aromatic, especially optionally substituted phenyl group as just described.

In another particularly preferred class of compounds of formula (1) and (2) L$^1$ is a prefer ed atom or group as just described, especially an —O— or —S— atom or —N(R$^{10}$)—, especially —NH— group. In this class of compounds p is preferably zero and R$^1$ is preferably an optionally substituted C$_{3-10}$cycloaliphatic, C$_{2-10}$heterocycloaliphatic, C$_{6-12}$aromatic or C$_{1-9}$heteroaromatic group as herein generally and particularly described. Most preferably R$^1$ is an optionally substituted cycloaliphatic, especially C$_{3-7}$cycloalkyl group or an optionally substituted C$_{6-12}$aromatic, especially phenyl group as just described.

Particularly preferred Ar aromatic groups include optionally substituted phenyl groups. Particularly preferred heteroaromatic groups include optionally substituted monocyclic heteroaromatic groups, especially optionally substituted five- or six-membered heteroaromatic groups containing one, two, three or four heteroatoms selected from oxygen, sulphur or nitrogen atoms. Particularly preferred optionally substituted monocyclic heteroaromatic groups include optionally substituted furyl, thienyl, pyrrolyl, oxazolyl, thiazolyl, pyridyl, pyrimidinyl or triazinyl group.

Particularly preferred optional substituents which may be present on Ar aromatic or heteroaromatic groups include those —R$^{18a}$ or -L$^5$Alk$^5$(R$^{18a}$)$_g$ atoms or groups as hereinbefore defined in relation to preferred R$^1$ aromatic groups.

In general in compounds of the invention Ar is preferably an optionally substituted phenyl group as generally and specifically described herein and in particular is a phenyl group.

In another preferred class of compounds of formula (1) and (2) m is zero.

In a further preferred class of compounds of formula (1) or (2) m is the integer 1. In this class of compounds R$^c$ is preferably an oxo (=O) atom or a C$_{1-6}$alkyl, most especially C$_{1-4}$alkyl e.g. methyl, ethyl or i-propyl group, or a haloC$_{1-6}$alkyl, most especially fluoroC$_{1-3}$alkyl e.g. —CHF$_2$ or —CF$_3$ group or a C$_{1-6}$alkoxy, especially C$_{1-3}$alkoxy e.g. methoxy or ethoxy or a haloC$_{1-6}$alkoxy, especially fluoroC$_{1-3}$alkoxy e.g. trifluoromethoxy group or a group -(Alk$^2$)$_r$R$^5$ in which R$^5$ is a cyano, —CO$_2$R$^2$, especially —CO$_2$CH$_3$ or —CO$_2$C(CH$_3$)$_3$, —NHR$^2$ especially —NHCH$_3$, —N(R$^2$)(R$^3$) especially —N(CH$_3$)$_2$, —COR$^2$ especially —COCH$_3$ or —COCH$_2$CH$_3$, —N(R$^3$)COR$^4$, especially —NHCOR$^4$ e.g. —NHCOCH3 or optionally substituted C$_{3-7}$cycloalkyl, C$_{2-7}$heterocycloalkyl, C$_{6-12}$aromatic or C$_{1-9}$heteroaromatic group. In one preferred group of compounds of this class r is zero. In another preferred group of compounds of this class r is the integer 1 and Alk$^2$ is a C$_{1-3}$alkylene chain such as a —CH$_2$—, —CH$_2$CH$_2$—, —CH$_2$CH$_2$CH$_2$—, —CH(CH$_3$)CH$_2$— or —CH$_2$CH(CH$_3$)— chain.

Particularly preferred optionally substituted C$_{3-7}$cycloalkyl, C$_{2-7}$heterocycloalkyl, C$_{6-12}$aromatic or C$_{1-9}$heteroaromatic groups represented by R$^5$ include those preferred groups as described herein in relation to R$^1$.

Particularly useful compounds according to the invention include those described in the Examples hereinafter and the salts, solvates, hydrates and N-oxides thereof.

Compounds according to the invention are potent and selective inhibitors of p38 kinases, including all isoforms and splice variants thereof. More specifically the compounds of the invention are inhibitors of p38α, p38β and p38β2. The ability of the compounds to act in this way may be simply determined by employing tests such as those described in the Examples hereinafter.

The compounds of formula (1) are of use in modulating the activity of p38 kinases and in particular are of use in the prophylaxis and treatment of any p38 kinase mediated diseases or disorders in a human, or other mammal. The invention extends to such a use and to the use of the compounds for the manufacture of a medicament for treating such diseases or disorders. Further the invention extends to the administration to a human an effective amount of a p38 inhibitor for treating any such disease or disorder.

The invention also extends to the prophylaxis or treatment of any disease or disorder in which p38 kinase plays a role including conditions caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further the invention extends to the administration to a human an effective amount of a p38 inhibitor for treating any such disease or disorder.

Diseases or disorders in which p38 kinase plays a role either directly or via pro-inflammatory cytokines including the cytokines TNF, IL-1, IL-6 and IL-8 include without limitation autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation and conditions associated with prostaglandin endoperoxidase synthetase-2 (COX-2).

Autoimmune diseases which may be prevented or treated include but are not limited to rheumatoid arthritis, inflammatory bowel disease, ulcerative colitis, Crohn's disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs, host disease or psoriasis.

The invention further extends to the particular autoimmune disease rheumatoid arthritis.

Inflammatory diseases which may be prevented or treated include but are not limited to asthma, allergies, respiratory distress syndrome or acute or chronic pancreatitis.

Destructive bone disorders which may be prevented or treated include but are not limited to osteoporosis, osteoarthritis and multiple myeloma-related bone disorder.

Proliferative diseases which may be prevented or treated include but are not limited to acute or chronic myelogenous leukemia, Kaposi's sarcoma, metastatic melanoma and multiple myeloma.

Neurodegenerative diseases which may be prevented or treated include but are not limited to Parkinson's disease, Alzheimer's disease, cerebral ischemias or neurodegenerative disease caused by traumatic injury.

Viral diseases which may be prevented or treated include but are not limited to acute hepatitis infection (including hepatitis A, hepatitis B and hepatitis C), HIV infection and CMV retinitis.

Infectious diseases which may be prevented or treated include but are not limited to septic shock, sepsis and Shigellosis.

In addition, p38 inhibitors of this invention also exhibit inhibition of expression of inducible pro-inflammatory proteins such as prostaglandin endoperoxidase synthetase-2, otherwise known as cyclooxygenase-2 (COX-2) and are therefore of use in therapy. Pro-inflammatory mediators of the cyclooxygenase pathway derived from arachidonic acid are produced by inducible COX-2 enzyme. Regulation of COX-2 would regulate these pro-inflammatory mediators such as prostaglandins, which affect a wide variety of cells and are important and critical inflammatory mediators of a wide variety of disease states and conditions. In particular these inflammatory mediators have been implicated in pain, such as in the sensitization of pain receptors, or edema. Accordingly additional p38 mediated conditions which may be prevented or treated include edema, analgesia, fever and pain such as neuromuscular pain, headache, dental pain, arthritis pain and pain caused by cancer.

As a result of their p38 inhibitory activity, compounds of the invention have utility in the prevention and treatment of diseases associated with cytokine production including but not limited to those diseases associated with TNF, IL-1, IL-6 and IL-8 production.

Thus TNF mediated diseases or conditions include for example rheumatoid arthritis, rheumatoid spondylitis, osteoarthritis, gouty arthritis and other arthritic conditions, sepsis, septic shock syndrome, adult respiratory distress syndrome, cerebral malaria, chronic pulmonary inflammatory disease, silicosis, pulmonary sarcoiosis, bone resorption disease, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis, pyresis, viral infections such as HIV, CMV, influenza and herpes; and vetinary viral infections, such as lentivirus infections, including but not limited to equine infectious anemia virus, caprine arthritis virus, visna virus or maedi virus; or retrovirus infections, including feline immunodeficiency virus, bovine immunodeficiency virus or canine immunodeficiency virus.

Compounds of the invention may also be used in the treatment of viral infections, where such viruses elicit TNF production in vivo or are sensitive to upregulation by TNF. Such viruses include those that produce TNF as a result of infection and those that are sensitive to inhibition, for instance as a result of decreased replication, directly or indirectly by the TNF inhibiting compounds of the invention. Such viruses include, but are not limited to, HIV-1, HIV-2 and HIV-3, Cytomegalovirus (CMV), Influenza, adenovirus and the Herpes group of viruses such as Herpes Zoster and Herpes Simplex.

IL-1 mediated diseases or conditions include for example rheumatoid arthritis, osteoarthritis, psoriatic arthritis, traumatic arthritis, rubella arthritis, inflammatory bowel disease, stroke, endotoxemia and/or toxic shock syndrome, inflammatory reaction induced by endotoxin, diabetes, pancreatic β-cell disease, Alzheimer's disease, tuberculosis, atherosclerosis, muscle degeneration and cachexia.

IL-8 mediated diseases and conditions include for example those characterized by massive neutrophil infiltration such as psoriasis, inflammatory bowel disease, asthma, cardiac, brain and renal reperfusion injury, adult respiratory distress syndrome, thrombosis and glomerulonephritis. The increased IL-8 production associated with each of these diseases is responsible for the chemotaxis of neutrophils into inflammatory sites. This is due to the unique property of IL-8 (in comparison to TNF, IL-1 and IL-6) of promoting neutrophil chemotaxis and activation. Therefore, inhibition of IL-8 production would lead to a direct reduction in neutrophil infiltration.

It is also known that both IL-6 and IL-8 are produced during rhinovirus (HRV) infections and contribute to the pathogenesis of the common cold and exacerbation of asthma associated with HRV infection [Turner et al, Clin. Infec. Dis., 1997, 26, 840; Grunberg et al, Am. J. Crit. Care Med. 1997, 155, 1362; Zhu et al, J. Clin. Invest. 1996, 97, 421]. It has also been demonstrated in vitro that infection of pulmonary epithelial cells (which represent the primary site of infection by HRV) with HRV results in production of IL-6 and IL-8 [Sabauste et al, J. Clin. Invest. 1995, 96, 549]. Therefore, p38 inhibitors of the invention may be used for the treatment or prophylaxis of the common cold or respiratory viral infection caused by human rhinovirus infection (HRV), other enteroviruses, coronavirus, influenza virus, parainfluenza virus, respiratory syncytial virus or adenovirus infection.

For the prophylaxis or treatment of a p38 or pro-inflammatory cytokine mediated disease the compounds according to the invention may be administered to a human or mammal as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds for use according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively the compounds for use according to the present invention may be formulated in a suitable lotion containing the active component suspended or dissolved in one or more pharmaceutically acceptable carriers. Particular carriers include, for example mineral oil, sorbitan monostearate, polysorbate 60, cetyl esters wax, cetearyl alcohol, benzyl alcohol, 2-octyldodecanol and water.

For ophthalmic administration the compounds for use according to the present invention may be conveniently formulated as microionized suspensions in isotonic, pH adjusted sterile saline, either with or without a preservative such as bactericidal or fungicidal agent, for example phenylmercuric nitrate, benzylalkonium chloride or chlorhexidine acetate. Alternatively for ophthalmic administration compounds may be formulated in an ointment such as petrolatum.

For rectal administration the compounds for use according to the present invention may be conveniently formulated as suppositories. These can be prepared by mixing the active component with a suitable non-irritating excipient which is solid at room temperature but liquid at rectal temperature and so will melt in the rectum to release the active component. Such materials include for example cocoa butter, beeswax and polyethylene glycols.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols Ar, $R^1$, $Alk^1$, p, $L^1$, $R^a$, $R^b$, $R^c$, $R^d$, m, q, X and Y when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1999]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention a compound of formula (1) in which $R^a$ and $R^b$ are joined to form an oxo (═O) group, X is a nitrogen atom and Y is an optionally substituted —NH— group [formula (1a)] may be prepared according to the reactions set out in Scheme 1.

Thus a compound of formula (1a) may be prepared by reaction of a compound of formula (3) [where $Hal^1$ is a halogen atom e.g. a chlorine atom] with a nucleophilic agent of formula $R^1(Alk^1)_pL^1H$, where -$L^1$H is for example an —OH, —SH or —N($R^{10}$)H group.

The reaction may be performed in the presence of a solvent, for example an ether such as an alcohol, e.g. 2-ethoxyethanol cyclic ether, e.g. tetrahydrofuran or dioxane, an aromatic hydrocarbon such as toluene or a substituted amide such as dimethylformamide, optionally in the presence of a base, for example an inorganic base such as sodium hydride, or an organic base such as an organic amine, e.g. a cyclic amine such as 1,5-diazabicyclo[4.3.0]non-5-ene or a resin bound organic amine such as resin bound 2-tert-butylimino-2-diethylamino-1,3-dimethyl-perhydro-1,3,2-diazaphosphorine (PS-BEMP), at an elevated temperature, for example about 80° C. to the reflux temperature.

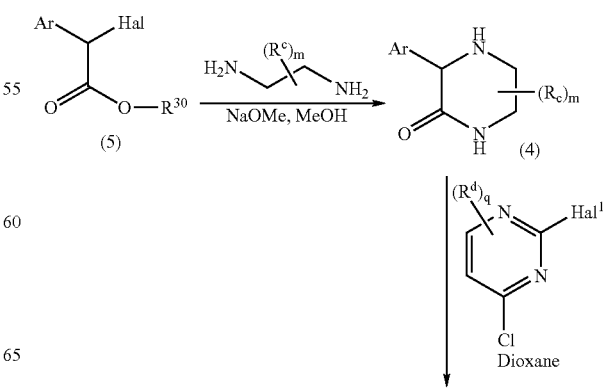

Scheme 1

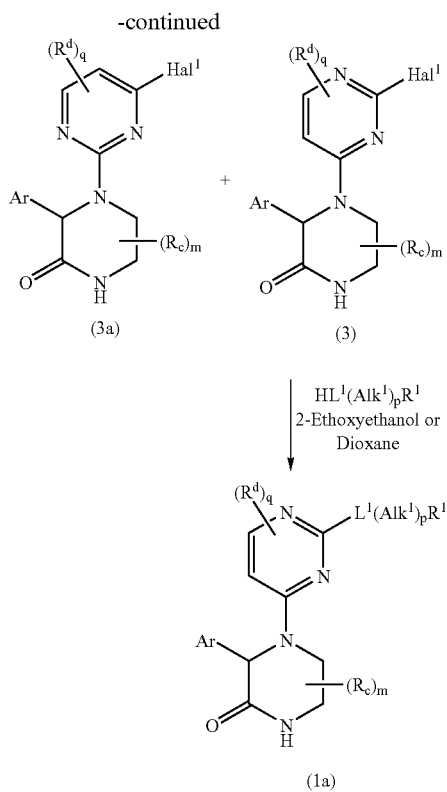

In a further aspect of the invention a compound of formula (1a) in which, for example, $L^1$ is a covalent bond and n is zero may be prepared by the Suzuki reaction of an intermediate of formula (3) [in which $Hal^1$ is a halogen atom such as a chlorine, bromine or iodine atom] with a boronic acid of formula $R^1B(OH)_2$. The reaction may be performed in an organic solvent, for example an aromatic hydrocarbon such as toluene or an ether such as an acyclic ether e.g. 1,2-dimethoxyethane or a cyclic ether e.g. tetrahydrofuran optionally in the presence of a base such as an aqueous carbonate e.g. sodium or potassium carbonate in the presence of a metal catalyst such as a palladium complex e.g. tetrakis(triphenylphosphine)palladium (0), at an elevated temperature e.g. around 80° C.

Intermediate halo e.g. chlorpyrimidines of formula (3) may be prepared from intermediate piperazinones of formula (4) by reaction with an optionally substituted di-halopyrimidine e.g. dichloropyrimidine. The reaction may be performed using similar conditions to those just described for the preparation of compounds of formula (1a) by nucleophilic displacement.

Piperazinones of formula (4) may be prepared from α-haloacetates of formula (5) [where Hal is a halogen atom such as a chlorine, bromine or iodine atom and $R^{30}$ is a $C_{1-6}$alkyl group such as a methyl] by reaction with an optionally substituted diethylamine of formula:

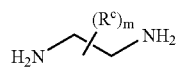

The reaction may be performed in the presence of a solvent such as a substituted amide for example dimethylformamide or an ether e.g. a cyclic ether such as tetrahydrofuran or an alcohol such as methanol or ethanol in the presence of a base, for example an inorganic base such as a hydride e.g. sodium hydride or an organic base such as 1,5-diazabicyclo[4.3.0]non-5-ene or a trialkylamine such as triethylamine or a sodium alkoxide such as sodium methoxide or sodium ethoxide at a temperature between about ambient and the reflux temperature.

According to another aspect of the invention further compounds of formula (1) may be prepared according to the methods set out in Scheme 2. Thus a compound of formula (1b) in which $R^a$ and $R^b$ is each a hydrogen atom may be prepared from an intermediate of formula (6) by the methods previously described to form compounds of formula (1a).

Intermediates of formula (6) may be prepared from intermediates of formula (7) by the methods described to prepare intermediates of formula (3), optionally with the addition of a prior N-protection (e.g. BOC protection) step and a subsequent N-deprotection step [in the case where Y is —NH—] under such standard conditions as described in Green (ibid).

Intermediates of formula (7) may be prepared from optionally substituted intermediates of formula (8) [in which $Hal^2$ is a halogen atom such as a bromine or iodine atom] by a two-step process involving reaction of an intermediate of formula (8) with a boronic acid of formula $ArB(OH)_2$ under the Suzuki reaction conditions previously described and subsequent reduction of the pyrazine ring by catalytic hydrogenation. The reduction reaction may be performed in a solvent such as an alcohol, e.g. methanol or ethanol in the presence of a catalyst such as a palladium catalyst e.g. palladium on charcoal in the presence of a source of hydrogen, preferably at an elevated pressure and optionally in the presence of an acid e.g. 6M hydrochloric acid and/or at an elevated temperature.

Scheme 2

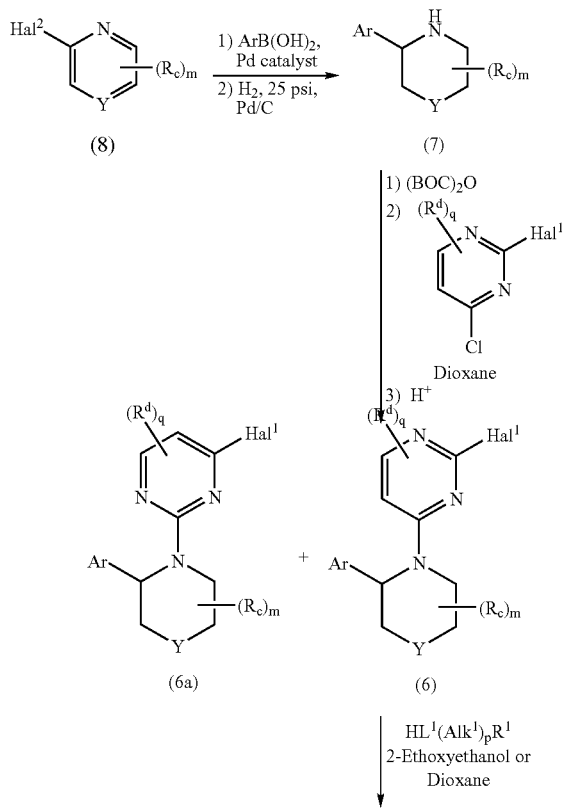

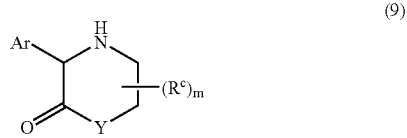

(1b)

Further compounds of the invention in which $R^a$ and $R^b$ is each a hydrogen atom may be prepared from compounds of formula (1a) or from intermediates of formula (9):

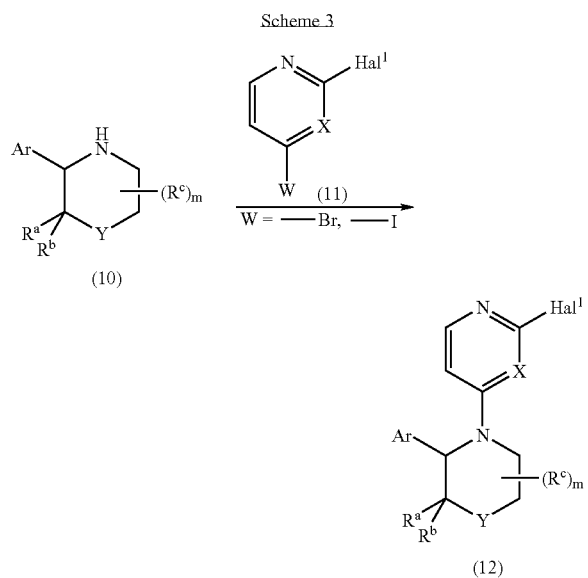

by reduction of the carbonyl group with an inorganic reducing agent such as a hydride e.g. lithium aluminium hydride or a borane such as borane-methyl sulfide complex in a solvent such as an ether e.g. a cyclic ether such as tetrahydrofuran or a halogenated hydrocarbon such as dichloromethane at a temperature between about 0° C. and the reflux temperature.

Further intermediates to compounds of the invention may be prepared by the methods depicted in Scheme 3.

Intermediates of formula (12) may be prepared from intermediates of formula (10) by reaction with an intermediate of formula (11) in which W is a halogen atom such as a chlorine, bromine or iodine atom by such well known metal catalysed coupling reactions as those of Buchwald (J. Am. Chem. Soc. 1996, 118, 7215-6; Tetrahedron Lett. 1997, 6359-62; J. Am. Chem. Soc. 1997, 199, 6054-58; J. Org. Chem. 1997, 62, 6066-8) or Hartwig (J. Am. Chem. Soc. 1996, 118, 7217-8; J. Org. Chem. 1997, 62, 1268-73).

Further intermediates (14) to compounds of the invention may be prepared from amino-alcohols [Y=O] or amino-thiols [Y=S] of formula (13) by the method of Scheme 4.

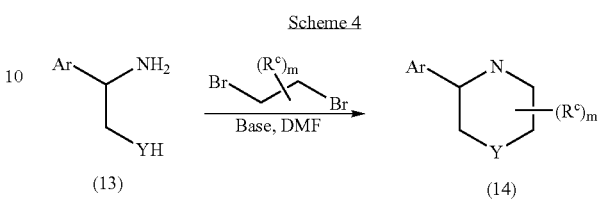

The reaction may be performed in a solvent such as an amide e.g. dimethylformamide or an ether such as a cyclic ether e.g. tetrahydrofuran in the presence of a base, for example an inorganic base such as a carbonate e.g. potassium or caesium carbonate or a hydride e.g. sodium hydride or an organic base such as 1,5-diazabicyclo[4.3.0]non-5-ene or a trialkylamine e.g. triethylamine or a sodium alkoxide such as sodium methoxide or sodium ethoxide at a temperature between about ambient and the reflux temperature.

Where in the general processes described above intermediates such as intermediates of formula (5), (8) and $HL^1(Alk^1)_pR^1$ and any other intermediates required in the synthesis of compounds of the invention are not available commercially or known in the literature, they may be readily obtained from simpler known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other intermediates and in particular compounds of formula (1) where appropriate functional groups exist in these compounds. Particular examples of such methods are given in the Examples hereinafter.

Thus for example aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile, a thiomethyl group may be introduced by using dimethyidisulphide as the electrophile, an alcohol group may be introduced by using an aldehyde as electrophile and an acid may be introduced by using carbon dioxide as electrophile. Aromatic acids of formula $ArCO_2H$ may also be generated by quenching Grignard reagents of formula ArMgHal with carbon dioxide.

Aromatic acids of formula $ArCO_2H$ generated by this method and acid containing compounds in general may be converted to activated derivatives, e.g. acid halides by reaction with a halogenating agent such as a thionyl halide e.g. thionyl chloride, a phosphorous trihalide such as phosphorous trichloride or a phosphorous pentahalide such as phosphorous pentachloride optionally in an inert solvent such as an aromatic hydrocarbon e.g. toluene or a chlorinated hydrocarbon e.g. dichloromethane at a temperature from about 0° C. to the reflux temperature, or may be converted into Weinreb amides of formula ArC(O)N(OMe)

Me by conversion to the acid halide as just described and subsequent reaction with an amine of formula HN(OMe)Me or a salt thereof, optionally in the presence of a base such as an organic amine, e.g. triethylamine in an inert solvent such as an aromatic hydrocarbon e.g. toluene or a chlorinated hydrocarbon e.g. dichloromethane at a temperature from about 0° C. to ambient temperature.

Compounds of the invention and intermediates thereto such as compounds of formulae (1a), (1b), (3), (6), (7), (13) and (14) may be prepared by alkylation, arylation or heteroarylation. For example, compounds containing a -$L^1$H or -$L^5$H group (where $L^1$ or $L^5$ is a linker atom or group) may be treated with an alkylating agent $R^1(Alk^1)_pZ^2$ or $(R^{18a})_gAlk^5Z^2$ respectively in which $Z^2$ is a leaving atom or group such as a halogen atom, e.g. a fluorine, chlorine, bromine or iodine atom or a sulphonyloxy group such as an alkylsulphonyloxy, e.g. trifluoromethylsulphonyloxy or arylsulphonyloxy, e.g. p-toluenesulphonyloxy group.

The reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran.

In another example, compounds containing a -$L^1$H or -$L^5$H group as defined above may be functionalised by acylation or thioacylation, for example by reaction with the alkylating agents just described but in which $Z^2$ is replaced by a —$C(O)Z^3$, $C(S)Z^3$, —$N(R^2)COZ^3$ or —$N(R^2)C(S)Z^3$ group in which $Z^3$ is a leaving atom or group as described for $Z^2$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $Z^2$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, or a benzotriazole such as [O-(7-azabenzo-triazol-1-yl)-1,1,3,3-tetramethyluronium] hexafluorophosphate advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction In a further example compounds may be obtained by sulphonylation of a compound containing an —OH group by reaction with one of the above alkylating agents but in which $Z^2$ is replaced by a —S(O)Hal or —$SO_2$Hal group [in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a -$L^1$H or -$L^5$H group as defined above may be coupled with one of the alkylation agents just described but in which $Z^2$ is replaced by an —OH group in a solvent such as tetrahydrofuran in the presence of a phosphine, e.g. triphenylphosphine and an activator such as diethyl, diisopropyl- or dimethylazodicarboxylate.

Ester groups such as —$CO_2Alk^6$ and —$CO_2R^2$ in the compound of formula (1) and intermediates thereto may be converted to the corresponding acid [—$CO_2H$] by acid- or base-catalysed hydrolysis depending on the nature of the group $Alk^6$ or $R^2$. Acid- or base-catalysed hydrolysis may be achieved for example by treatment with an organic or inorganic acid, e.g. trifluoroacetic acid in an organic solvent e.g. dichloromethane or a mineral acid such as hydrochloric acid in a solvent such as dioxan or an alkali metal hydroxide, e.g. lithium hydroxide in an aqueous alcohol, e.g. aqueous methanol.

In a further example, —$OR^{14}$ [where $R^{14}$ represents a $C_{1-6}$alkyl group such as methyl group] in compounds of formula (1) and intermediates thereto may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{31}$ group (where $R^{31}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [e.g. —$CO_2Alk^6$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^{14}$ group by coupling with a reagent $R^{14}$OH in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NH_2$] groups in the compounds may be obtained, in another example, by reaction of a corresponding amine [—$NH_2$] with sulphamide in the presence of an organic base such as pyridine at an elevated temperature, e.g. the reflux temperature.

In another example compounds containing a —$NHCSR^6$ or —$CSNHR^6$ group or compounds where $R^a$ and $R^b$ together form a thio (=S) group may be prepared by treating a corresponding compound containing a —$NHCOR^6$ or —$CONHR^6$ or $R^a$-$R^b$ oxo (=O) group with a thiation reagent, such as Lawesson's Reagent or $P_2S_5$, in an anhydrous solvent, for example a cyclic ether such as tetrahydrofuran, at an elevated temperature such as the reflux temperature.

In a further example amine (—$NH_2$) groups may be alkylated using a reductive alkylation process employing an aldehyde and a reducing agent. Suitable reducing agents include borohydrides for example sodium triacetoxyborohyride or sodium cyanoborohydride. The reduction may be carried out in a solvent such as a halogenated hydrocarbon, e.g. dichloromethane, a ketone such as acetone, or an alcohol, e.g. ethanol, where necessary in the presence of an acid such as acetic acid at around ambient temperature. Alternatively, the amine and aldehyde may be initially reacted in a solvent such as an aromatic hydrocarbon e.g. toluene and then subjected to hydrogenation in the presence of a metal catalyst, for example palladium on a support such as carbon, in a solvent such as an alcohol, e.g. ethanol.

In a further example, amine [—$NH_2$] groups in compounds of formula (1) and intermediates thereto may be obtained by hydrolysis from a corresponding imide by reaction with hydrazine in a solvent such as an alcohol, e.g. ethanol at ambient temperature.

In another example, a nitro [—$NO_2$] group may be reduced to an amine [—$NH_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example amine (—$CH_2NH_2$) groups in compounds of formula (1) and intermediates thereto may be obtained by reduction of nitriles (—CN), for example by catalytic hydrogenation using for example hydrogen in the presence of a metal catalyst, for example palladium on a support such as carbon, or Raney® nickel, in a solvent such as an ether e.g. a cyclic ether such as tetrahydrofuran or an alcohol e.g. methanol or ethanol, optionally in the presence of ammonia solution at a temperature from ambient to the reflux temperature, or by chemical reduction using for example a metal hydride e.g. lithium aluminium hydride, in a solvent such as an ether e.g. a cyclic ether such as tetrahydrofuran, at a temperature from 0° C. to the reflux temperature.

In another example, sulphur atoms in the compounds, for example when present as a Y atom or in a group $L^1$ or $L^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In a further example N-oxides of compounds of formula (1) may in general be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid or m-chloroperoxybenzoic acid in a solvent,such as a halogenated hydrocarbon e.g. dichloromethane or an alcohol e.g. tert-butanol at a temperature from the ambient temperature to the reflux temperature.

In another example further compounds of the invention using such well know and commonly used reactions as are to be found in the general reference texts *Rodd's Chemistry of Carbon Compounds,* Volumes 1-15 and Supplementals (Elsevier Science Publishers, 1989), *Fieser and Fieser's Reagents for Organic Synthesis,* Volumes 1-19 (John Wiley and Sons, 1999), *Comprehensive Heterocyclic Chemistry,* Ed. Katritzky et al, Volumes 1-8, 1984 and Volumes 1-11, 1994 (Pergamon), *Comprehensive Organic Functional Group Transformations,* Ed. Katritzky et al, Volumes 1-7, 1995 (Pergamon), *Comprehensive Organic Synthesis,* Ed. Trost and Flemming, Volumes 1-9, (Pergamon, 1991), *Encyclopedia of Reagents for Organic Synthesis,* Ed. Paquette, Volumes 1-8 (John Wiley and Sons, 1995), *Larock's Comprehensive Organic Transformations* (VCH Publishers Inc., 1989) and *March's Advanced Organic Chemistry* (John Wiley and Sons, $5^{th}$ Ed., 2001).

Salts of compounds of formula (1) may be prepared by reaction of compounds of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) or may be separated using chiral High Performance Liquid Chromatography. Alternatively, if desired a particular enantiomer may be obtained by using an appropriate chiral intermediate in one of the processes described above. Alternatively, a particular enantiomer may be obtained by performing an enantiomer specific enzymatic biotransformation e.g. an ester hydrolysis using an esterase and then purifying only the enantiomerically pure hydrolysed acid from the unreacted ester antipode.

Chromatography, recrystallisation and other conventional separation procedures may also be used with intermediates or final products where it is desired to obtain a particular geometric isomer of the invention.

The following Examples illustrate the invention. All temperatures are in ° C.

The following abbreviations are used:
NMM—N-methylmorpholine; EtOAc—ethyl acetate; MeOH—methanol; BOC—butoxycarbonyl; DCM—dichloromethane; AcOH—acetic acid; DIPEA—diisopropylethylamine; EtOH—ethanol; Pyr—pyridine; Ar—aryl;
DMSO—dimethylsulphoxide; iPr—isopropyl; $Et_2O$—diethylether; Me—methyl;
THF—tetrahydrofuran, DMF—N,N-dimethylformamide; FMOC—9-fluorenylmethoxycarbonyl; NBS—N-bromosuccinimide
DBU—1,8-Diazabicyclo[5,4-0]undec-7-ene
MCPBA—3-chloroperoxybenzoic acid
PS-BEMP—resin bound 2-tert-butylimino-2-diethylamino-1,3-dimethyl-perhydro-1,3,2-diazaphosphorine All NMR's were obtained either at 300 MHz or 400 MHz.

Compounds were named with the aid of Beilstein Autonom supplied by MDL Information Systems GmbH, Theodor-Heuss-Allee 108, D60486 Frankfurt, Germany, or were given names that appear consistent with this.

Experimental

LCMS retention times (RT) quoted were generated on a Hewlett Packard 1100 LC/MS using the following method: Phenomenex Luna 3 $\mu C_{18}(2)$ 50×4.6 mm column; mobile phase A=0.1% formic acid in water; mobile phase B=0.1% formic acid in MeCN; flow rate of 0.9 $mLmin^{-1}$, column temperature 40° C.

| Gradient:- | Time | % B |
| --- | --- | --- |
|  | Initial | 5 |
|  | 2.00 | 95 |
|  | 3.00 | 95 |
|  | 5.0 | 5 |
|  | 5.5 | end |

Intermediate 1

3-Phenyl-piperazin-2-one

Methyl bromophenyl acetate (25 g, 109 mmol) and ethylene diamine (13.1 g, 218 mmol) were mixed in dry MeOH (180 mL) and stirred at room temperature for 15 minutes under nitrogen. Sodium methoxide (6.5 g, 120 mmol) was added in one portion and the mixture heated to reflux for 3.5 hr. The mixture was left stirring overnight at room temperature. The solvent was evaporated in vacuo to give a pale yellow gum, which was partitioned between water (100 mL) and chloroform (100 mL), the pH of the aqueous phase was adjusted with 2M HCl to pH 7.5 and extracted with more chloroform (100 mL). The combined organic phases were dried (MgSO$_4$) and evaporated to give the title compound as a pale yellow solid (17 g, 89%).

δH NMR (CDCl$_3$): 7.42-7.15 (5H, m), 6.85 (1H, br-s), 4.5 (1H, s), 3.52-3.20 (2H, m), 3.00 (2H, m), 2.50 (1H, br-s).

LCMS (ES$^+$) Retention time 0.65 minutes, 177 (MH)$^+$.

Intermediate 2

4-(2-Chloro-pyrimidin-4-yl)-3-phenyl-piperazln-2-one

Intermediate 1, (0.5 g, 2.84 mmol), 2,4-dichloropyrimidine (0.47 g, 3.13 mmol) and sodium bicarbonate (0.26 g, 3.13 mmol) in dry EtOH (5 mL) were refluxed for 30 minutes under an atmosphere of nitrogen. The mixture was filtered, and the filtrate evaporated in vacuo to give a yellow solid as a 4:1 mixture of regioisomers in favour of the required isomer. The solid was purified by flash chromatography (1% MeOH in DCM followed by 10% MeOH in DCM/silica) to give the required isomer as a pure white solid.

δH NMR (d$_6$ DMSO): 8.45 (1H, br-s), 8.25 (1H, d, J=6.0 Hz), 7.5-7.2 (5H, m), 6.76 (1H, br-s), 5.82 (1H, br-s), 4.0-3.2 (4H, m). LCMS (ES$^+$) Retention time 2.72 minutes, 289 (MH)$^+$.

Intermediate 3

4-(2-Chloro-pyrimidin-4-yl)-1-methyl-3-phenyl-piperazin-2-one

To a solution of Intermediate 2, (0.20 g, 0.69 mmol) in dry toluene (10 mL) was added PS-BEMP (0.5 g) and methyl iodide (0.29 g, 2.08 mmol) in one portion, under an atmosphere of nitrogen. The mixture was heated under reflux for 18 hrs. The brown suspension was filtered and the filtrate evaporated in vacuo to give a yellow oil. The oil was purified by chromatography (0-5% MeOH in EtOAc/silica) to give the title compound as a white solid (0.15 g, 72%).

LCMS (ES$^+$) Retention time 3.05 minutes, 303 (MH)$^+$.

Intermediate 4

4-(2-Chloro-pyrimidin-4-yl)-1-cyclopropylmethyl-3-phenyl-piperazin-2-one

To a solution of Intermediate 2, (0.20 g, 0.69 mmol) in dry toluene (10 mL) was added PS-BEMP (0.5 g) and cyclopropylmethyl bromide (0.28 g, 2.07 mmol) in one portion, under an atmosphere of nitrogen. The mixture was heated under reflux for 48 hrs. The brown suspension was filtered and the filtrate evaporated in vacuo to give a yellow oil. The oil was purified by chromatography (0-5% MeOH in EtOAc/silica) to give the title compound as a white solid (0.16 g, 67%).

LCMS (ES$^+$) Retention time 3.36 minutes, 343 (MH)$^+$.

Intermediate 5

1-Benzyl-4-(2-chloro-pyrimidin-4-yl)-1-methyl-3-phenyl-piperazin-2-one

Intermediate 2, (0.30 g, 1.04 mmol) and benzyl bromide (0.54 g, 3.11 mmol) were reacted together following the procedure detailed for Intermediate 3, which gave the title compound as a pale yellow solid (0.39 g, 99%). Taken to the next step without purification (>90%).

LCMS (ES$^+$) Retention time 3.61 minutes, 379 (MH)$^+$.

Intermediate 6

1-Allyl-4(2-chloro-pyrimidinyl-4-yl)-3-phenyl-piperazin-2-one

Intermediate 2, (0.30 g, 1.04 mmol) and allyl bromide (0.38 g, 3.11 mmol) were reacted together following the procedure detailed for Intermediate 3, which gave the title compound as a yellow solid (0.27 g, 78%). This was taken to the next step without any purification (crude>90%).

δH NMR (d$_3$ MeOD): 7.95 (1H, d, J=6.15 Hz), 7.47-7.21 (5H, m), 6.55 (1H, d, J=6.2 Hz), 5.95 (1H, br-s), 5.66 (1H, m), 5.07 (2H, m), 4.00-3.86 (4H, m), 3.42 (2H, m). LCMS (ES$^+$) Retention time 3.31 minutes, 329 (MH)$^+$.

Intermediate 7

Bromo-(4-fluoro-phenyl)-acetic acid methyl ester

4-Fluorophenylacetic acid methyl ester (3.0 g, 17.6 mmol) in THF (20 mL) under nitrogen at −78° was treated with 1M lithium hexamethyldisilazide (19.4 mL, 19.4 mmol) and stirred at −78° for fifteen minutes. Trimethyl silyl chloride was added (2.23 mL, 17.6 mmol) and the reaction stirred for a further fifteen minutes. Bromine (0.9 mL, 17.6 mmol) was added and the reaction stirred again for a further fifteen minutes then quenched with water and partitioned between DCM and sodium hydrogen carbonate solution. The organic phase was separated, dried (sodium sulphate) and concentrated in vacuo. Flash chromatography (diethyl-ether-silica) yielded the title compound.

δH NMR (CDCl$_3$): 7.42-7.35 (2H, m), 6.94-6.85 (2H, m), 5.18 (1H, s), 3.64 (3H, s).

Intermediate 8

3-(4-Fluoro-phenyl)-piperazin-2-one

Intermediate 7, (4.0 g, 16.2 mmol) and ethylene diamine (2.2 mL, 33 mmol) were mixed and stirred at room temperature for ten minutes in methanol. Sodium methoxide (0.97 g, 18.0 mmol) was added as a solid and the reactions heated under reflux for three hours. Concentrated hydrochloric acid was added to neutralise the excess sodium methoxide and the reaction mixture concentrated in vacuo. Chromatography (ethyl acetate-tetrahydrofuran 0-100%—silica) yielded the title compound.

δH NMR (CDCl$_3$): 7.45-7.34 (2H, m), 7.08-7.01 (2H, m), 6.62 (1H, br-s), 4.56 (1H, s), 3.59-3.48 (1H, m), 3.41-3.31 (1H, m), 3.21-3.05 (2H, m).

Intermediate 9

4-(2-Chloro-pyrimidin-4-yl)-3-(4-fluoro-phenyl)-piperazin-2-one

Intermediate 8, (4.8 g, 24.7 mmol) and 2,4-dichloropyrimidine (3.6 g, 24.2 mmol) in ethoxyethanol (40 mL) were heated at 100° for four hours. The reaction mixture was concentrated in vacuo and the residue chromatographed (DCM-50% THF/DCM-silica) to yield the title compound.

δH NMR (CDCl$_3$): 8.11 (1H, d, J=6.07 Hz), 7.45-7.41 (2H, m), 7.11-7.05 (2H, m), 6.55 (1H, br-s), 6.30 (1H, d J=6.07 Hz), 5.76 (1H, br-s), 4.28-4.23 (1H, m), 3.85-3.77 (1H, m), 3.62-3.43 (2H, m). LCMS (ES$^+$) Retention time 2.865 minutes, 307 (MH)$^+$ Intermediate 10

2-Phenyl-piperazine

Intermediate 1 (7.7 g, 43.8 mmol), was added as a solid to lithium aluminium hydride (7.5 g, 198 mmol) in THF (250 mL) under nitrogen and stirred at room temperature for three hours. After quenching with 2M sodium hydroxide the precipitate was filtered off and the solid residue washed with THF. The combined organic filtrates were concentrated in vacuo to yield the title compound 7 g).

δH NMR (d$_6$ DMSO): 7.37-7.34 (2H, m), 7.31-7.27 (2H, m), 7.24-7.19 (2H, m), 3.61-3.57 (1H, m), 2.92-2.84 (1H, m), 2.82-2.66 (3H, m), 2.63-2.55 (1H, m), 2.41-2.33 (1H, m).

Intermediate 11

3-Phenyl-piperazine-1-carboxylic acid tert-butyl ester

Intermediate 10, (7 g, 43.2 mmol) in DCM (20 mL) and toluene (150 mL) was treated with carbonic acid di-tert-butyl ester (8.5 g, 38.9 mmol) and stirred for thirty minutes at room temperature then heated to 80° for two hours. The reaction mixture was concentrated in vacuo and the residue chromatographed (DCM/5% MeOH/0.5% triethylamine-silica), to yield the title compound (4.1 g).

δH NMR (CDCl$_3$): 7.36-7.31 (2H, m), 7.30-7.20 (3H, m), 4.08-3.88 (2H, br-m), 3.68-3.60 (1H, m), 3.03-2.97 (1H, m), 2.92-2.78 (2H, m), 2.76-2.61 (1H, br-m), m), 1.74-1.56 (1H, br-m), 1.40 (9H, s).

Intermediate 12

4-(2-Chloro-pyrimidin-4-yl)-3-phenyl-piperazine-1-carboxylic acid tert-butyl ester Intermediate 11, (0.5 g, 1.9 mmol) and 2,4-dichloropyrimidine (0.28 g, 1.9 mmol) were dissolved in EtOH (5 mL) and treated with sodium hydrogen carbonate (0.18 g, 2.1 mmol), the reaction was heated under reflux for four hours then left to stand at room temperature over night. The reaction mixture was concentrated in vacuo and chromatographed (EtOAc/hexane-silica) to yield the title compound (437 mg).

δH NMR (d$_3$ MeOD): 7.88 (1H, d, J, 6.24 Hz), 7.28-7.24 (2H, m), 7.20-7.17 (3H, m), 6.46 (1H, br-d, J=5.47), 5.38 (1H, br-s), 4.36-4.21 (2H, m), 3.79-3.58 (1H, m), 3.56 (2H, m), 3.22-3.20 (1H, m), 1.29-1.23 (9H, br-s), amide conformers present. LCMS (ES$^+$) Retention time 3.857 minutes, 375(MH)$^+$ Intermediate 13

4-[2-(3-Chloro-phenylamino)-pyrimidin-4-yl]-3-phenyl-piperazine-1-carboxylic acid tert-butyl ester Intermediate 12, (500 mg, 1.34 mmol) and 3-chloroaniline (879 mg, 6.89 mmol) were dissolved in ethoxyethanol (3 mL) and treated with trifluoroacetic acid (314 mg, 2.75 mmol) and stirred at 90° for four hours. The reaction mixture was cooled, diluted with EtOAc, washed with saturated sodium hydrogen bicarbonate solution dried over sodium sulphate and concentrated in vacuo. Chromatography (0-50% EtOAc-DCM-silica) yielded the title compound as mixtures of conformers.

δH NMR (d$_6$ DMSO): 8.95 (1H, s), 8.00 (1H, d, J=6.04 Hz), 7.86 (1H, t, J=2.02 Hz), 7.55-7.52 (1H, m), 7.36-7.16 (6H, m), 6.90-6.87 (1H, m), 6.18 (1H, d, J=6.07 Hz), 5.54 (1H, t, J=3.81 Hz), 4.31-4.18 (2H, m), 3.79-3.73 (1H, m), 3.64-3.57 (1H, m), 3.55-3.48 (1H, m), 3.29-3.22 (1H, m), 1.33 (9H, s). LCMS (ES$^+$) Retention time 2.953 minutes, 466(MH)$^+$.

Intermediate 14

2-Phenylpyridine

2-Chloropyridine (10 g, 88.0 mmol), phenylboronic acid (12.9 g, 105.7 mmol), tetrakis(triphenylphosphine)palladium (0) (5.0 g, 5 mol %) and 2M Na$_2$CO$_3$ (50 mL) were all dissolved in ethylene glycol dimethylether (200 mL) at room temperature, under an atmosphere of nitrogen. The mixture was refluxed for 48 hours. Ethylene glycol dimethylether was evaporated in vacuo to give a red oil, which was partitioned between water (10 mL) and EtOAc (10 mL). The EtOAc layer was separated and the aqueous layer was further extracted with EtOAc (10 mL×2). The combined EtOAc layers were dried (MgSO$_4$) and concentrated in vacuo to a red oil. Purification by flash column chromatography (iso-hexaneethyl acetate 1:5-silica) gave the title product as a colourless oil (9.6 g, 70%).

δH (CDCl$_3$): 8.70 (1H, m) 7.95 (2H, m), 7.70 (2H, m), 7.5-7.1 (4H, m). LCMS (ES$^+$) Retention time 2.50 minutes, 156 (MH)$^+$.

Intermediate 15

2-Phenylpiperidine

2-Phenylpyridine, Intermediate 14, (4.0 g, 25.81 mmol), and concentrated HCl (3 mL) in EtOH (15 mL) were treated with platinum oxide and subjected to catalytic hydrogenation (~1 atm, balloon), at room temperature for 72 hours. After removal of the catalyst by filtration, the solution was evaporated in vacuo to a pale yellow HCl salt of the product. The free base is obtained by treating the residue with 10% aqueous sodium hydroxide. The aqueous is then extracted with Et$_2$O several times and the extracts dried (MgSO$_4$) and evaporated to an oil to give the title compound.

δH NMR (d$_6$ DMSO): 9.41 (1H, d), 7.40 (5H, m), 4.12 (2H, d), 3.0 (3H, m), 1.83 (3H, m). LCMS (ES$^+$) Retention time 0.82 minutes, 162 (MH)$^+$.

Intermediate 16

2-Chloro-4-(2-phenyl-piperidin-1-yl)-pyrimidine

2-Phenylpiperidine, Intermediate 15, (0.5 g, 2.52 mmol), 2,4-dichloropyrimidine (0.41 g, 2.77 mmol) and sodium bicarbonate (0.59 g, 5.55 mmol) in dry EtOH (10 mL) were refluxed for 2 hours, under an atmosphere of nitrogen. The mixture was filtered and the filtrate evaporated in vacuo to give a yellow oil. The oil was purified by flash chromatography (EtOAc and isohexane (1:3)/silica) to give the title compound as a colourless oil (46 g, 66%).

δH NMR (CDCl$_3$): 7.95 (1H, d, J=6.0 Hz), 7.30-7.00 (5H, m), 6.25 (1H, d, J=6.0 Hz), 5.50 (1H, br-s), 4.35 (1H, m), 3.00 (1H, m), 2.30 (1H, m), 1.95 (1H, m), 1.60 (4H, m). LCMS (ES$^+$) Retention time 3.87 minutes, 275 (MH)$^+$.

Intermediate 17

(R)-5-Phenyl-morpholin-3-one (R)-Phenylglycinol (0.20 g, 1.46 mmol) in dry THF (10 mL) was treated with triethylamine (0.18 g, 1.75 mmol) in one portion at 0°, under an atmosphere of nitrogen. Chloroacetylchloride (0.20 g, 1.75 mmol) was added dropwise over 15 minutes at 0°. The mixture was allowed to reach room temperature over 1 hour then quenched with water (5 mL) and EtOAc (5 mL). The organic layer was washed with brine (10 mL), dried (MgSO$_4$) and evaporated in vacuo to a white solid. NMR shows the precursor to the product (non ring closed). The solid was dissolved in dry THF (5 mL) and 10M NaOH was added slowly at 0°. The suspension was allowed to reach room temperature over 1.5 hours. The suspension was diluted with water (10 mL) and EtOAc (10 mL) and the organic layer was further washed with water (10 mL), then dried (MgSO$_4$) and evaporated in vacuo to a crude yellow solid, which was taken to the next step without any purification.

δH NMR (CDCl$_3$): 7.39-7.04 (5H, m), 4.60 (1H, m), 4.14 (2H, d, J=16.7 Hz), 4.05 (2H, d, J=16.7 Hz), 4.00 (1H, dd, J=4.3 and 13.2 Hz), 3.46 (1H, dd, J=8.0 and 11.8 Hz). LCMS (ES$^+$) Retention time 2.47 minutes, 177 (MH)$^+$. (Data and experimental are the same for the S-enantiomer).

Intermediate 18

(R)3-Phenyl-morpholine

Intermediate 17, (0.17 g, 0.96 mmol) in dry THF (10 mL) was treated with lithium aluminum hydride (0.17 g, wt/wt) in one portion at 0°, under an atmosphere of nitrogen. The mixture was allowed to reach room temperature and stirred at room temperature for 2 hours. The suspension was slowly quenched with saturated sodium bicarbonate (10 mL) at 0°, and then filtered through Celite® and the filtrate evaporated in vacuo to a yellow oil. The oil was purified by flash column chromatography (EtOAc/silica) to give the title compound as a pale yellow oil (0.09 g, 57%).

δH NMR (CDCl$_3$): 7.45-7.10 (5H, m), 3.80 (3H, m), 3.55 (1H, m), 3.37 (1H, m), 3.05 (1H, m), 2.90 (1H, m). LCMS (ES$^+$) Retention time 0.62 minutes, 164 (MH)$^+$. (Data and experimental are the same for the S-enantiomer).

Intermediate 19

(R)-4-(2-Chloro-pyrimidin-4-yl)-3-phenyl-morpholine

Intermediate 18, (1.0 g, 6.13 mmol) and 2,4-dichloropyrimidine (1.0 g, 6.71 mmol) were reacted together following the procedure detailed for Intermediate 2, which gave the title compound as a white solid (0.72 g, 43%).

δH NMR (CDCl$_3$): 7.97 (1H, d, J=6.1 Hz), 7.33-7.15 (5H, m), 6.27 (1H, d, J=6.1 Hz), 5.30 (1H, br-s), 4.35 (1H, d, J=12.0 Hz), 4.18-3.90 (3H, m), 3.64 (1H, m), 3.35 (1H, m). LCMS (ES$^+$) Retention time 3.36 minutes, 276 (MH)$^+$. (Data and experimental are the same for the S-enantiomer).

Intermediate 20

4-(5-Bromo-2-chloro-pyrimidin-4-yl)-3-phenyl-piperazin-2-one

To a solution of Intermediate 1, (4.38 g, 24.9 mmol) in MeOH (200 mL) were added 5-bromo-2,4-dichloropyrimidine (5.15 g, 22.6 mmol) and sodium bicarbonate (3.8 g, 45.2 mmol). The mixture was stirred at room temperature for 2 days. The reaction mixture was concentrated in vacuo. The residue was dissolved in 1% MeOH:DCM and washed with water and brine, dried over magnesium sulphate and concentrated in vacuo. The residue was recrystallised from MeOH to give the title compound as a white crystalline solid (4.95 g).

δH NMR (CDCl$_3$): 8.14 (1H, s), 7.38 (2H, m), 7.18 (3H, m), 6.47 (1H, br-s), 6.25 (1H, s), 4.38 (1H, m), 3.60 (1H, m), 3.37 (1H, m), 3.19 (1H, m).

Intermediate 21

3-Phenyl-4-[5-bromo-2-(1(R)-phenyl-ethylamino)-pyrimidin-4-yl]-piperazin-2-one

To a solution of Intermediate 20, (400 mg, 1.09 mmol) in ethoxyethanol (5 mL) was added (R)-(−)-α-methylbenzylamine (330 mg, 2.72 mmol). The mixture was stirred at 100° for 16 hr. The mixture was cooled and concentrated in vacuo. The residue was dissolved in 1% MeOH:DCM and washed with water and brine, dried over magnesium sulphate and concentrated in vacuo. The residue was recrystallised from MeOH/acetone to give the title compound as a white crystalline solid (261 mg).

LCMS (ES$^+$) Retention time 3.116 minutes, 453 (MH)$^+$.

EXAMPLE 1

3-Phenyl-4-[2-(3-trifluoromethyl-benzylamino)-pyrimidin-4-yl]-piperazin-2-one

Intermediate 2, (0.20 g, 0.69 mmol) in dry EtOH (10 mL) was added to sodium bicarbonate (0.38 g, 4.56 mmol) and 3-trifluoromethyl benzylamine (0.79 g, 4.56 mmol) in one portion at room temperature under an atmosphere of nitrogen. The suspension was refluxed for 48 hours, cooled then filtered and the filtrate evaporated in vacuo to a yellow gum. The gum was purified by chromatography (1-10% MeOH in EtOAc/silica) to give the title compound as a white solid.

δH NMR (CDCl$_3$): 7.89 (1H, d, J=5.95 Hz), 7.67-7.21 (9H, m), 5.96 (1H, br-s), 5.85 (1H, d, J=6.0 Hz), 4.64 (2H, m), 3.95 (1H, br-s), 3.70 (1H, m), 3.42 (2H, m). LCMS (ES$^+$) Retention time 2.42 minutes, 428 (MH)$^+$.

EXAMPLE 2

3-[4-(4-Methyl-3-oxo-2-phenyl-piperazin-1-yl)-pyrimidin-2-ylamino]-benzonitrile

Intermediate 3, (0.15 g, 0.50 mmol) in dry ethoxyethanol (5 mL) was added to 3-cyanoamine (0.06 g, 0.54 mmol), under an atmosphere of nitrogen. The mixture was heated to 100° and stirred for 18 hrs, then cooled and evaporated in vacuo to give a brown oil. The oil was purified by flash column chromatography (5-10% MeOH in EtOAc/silica) to give the title compound as a white solid (0.11 g, 58%).

δH NMR (d$_3$ MeOD): 7.90 (2H, m), 7.60 (1H, d, J=6.0 Hz), 7.45-7.09 (8H, m), 6.18 (1H, d, J=6.2 Hz), 6.09 (1H, br-s), 3.95 (1H, m), 3.72 (1H, m), 3.54 (2H, m), 2.95 (3H, s).

LCMS (ES$^+$) Retention time 4.05 minutes, 332 (MH)$^+$.

EXAMPLE 3

3-[4-(4-Cyclopropylmethyl-3-oxo-2-phenyl-piperazin-1-yl)-pyrimidin-2-ylamino]-benzonitrile Intermediate 4, (0.20 g, 0.58 mmol) and 3-cyanoaniline (0.14 g, 1.17 mmol) were reacted together following the procedure detailed for the compound of Example 2 which gave the title compound as a pale yellow solid (0.18 g, 72%).

δH NMR (d$_3$ MeOD): 8.03 (1H, d, J=6.0 Hz), 7.99 (1H, s), 7.71 (1H, m), 7.46-7.20 (7H, m), 6.25 (1H, d, J=6.0 Hz), 6.16 (1H, br-s), 3.87 (2H, m), 3.65 (2H, m), 3.33 (2H, m), 1.29 (2H, m), 0.51 (2H, m), 0.20 (2H, m).

LCMS (ES$^+$) Retention time 2.61 minutes, 425 (MH)$^+$.

EXAMPLE 4

3-[4-(4Benzyl-3-oxo-2-phenyl-piperazin-1-yl)-pyrimidin-2-ylamino]-benzonitrile Intermediate 5, (0.39 g, 1.03 mmol) and 3-cyanoaniline (0.14 g, 1.17 mmol) were reacted together following the procedure detailed for the compound of Example 2, which gave the title compound as a pale yellow solid (0.28 g, 58%).

δH NMR (d$_3$ MeOD): 7.90 (1H, d, J=5.9 Hz), 7.75 (1H, s), 7.56 (1H, m), 7.55-7.06 (11H, m), 6.82 (1H, m), 6.31 (1H, d, J=6.3 Hz), 6.09 (1H, br-s), 4.67 (1d, J=14.7 Hz), 4.43 (1H, d, J=14.7 Hz), 3.81 (1H, br-s), 3.53-3.24 (4H, m), LCMS (ES$^+$) Retention time 2.79 minutes, 461 (MH)$^+$.

EXAMPLE 5

3-[4-(4Allyl-3-oxo-2-phenyl-piperazin-1-yl)-pyrimidin-2-ylamino]-benzonitrile Intermediate 6, (0.10 g, 0.30 mmol) and 3-cyanoaniline (0.05 g, 0.45 mmol) were reacted together following the procedure detailed for the compound of Example 2, with the addition of an equivalent of tosic acid which eventually gave the title compound as a white solid (0.07 g, 57%).

δH NMR (d$_3$ MeOD): 7.93 (1H, d, J=6.1 Hz), 7.87 (1H, s), 7.61 (4H, m), 7.35-7.10 (4H, m) 6.16 (1H, d, J=6.1 Hz), 6.08 (1H, br-s), 5.68 (1H, m), 5.05 (2H, m), 4.09-3.72 (4H, m), 3.41 (2H, m). LCMS (ES$^+$) Retention time 2.56 minutes, 411 (MH)$^+$.

EXAMPLE 6

3-[4-(2-Phenyl-piperidin-1-yl)-pyrimidin-2-ylamino]-benzonitrile

Intermediate 16, (0.20 g, 0.73 mmol) in dry ethoxyethanol (5 mL) and 3-cyanoaniline (0.07 g, 0.80 mmol), were heated to 100° under an atmosphere of nitrogen and stirred for 18 hours. The mixture was cooled and evaporated in vacuo to give a brown oil. The oil was purified by chromatography (5-20% MeOH in EtOAc/silica) to give the title compound as a white solid (0.23 g, 84%).

δH NMR (d$_3$ MeOD): 7.78 (2H, m), 7.54 (1H, d, J=2.4 Hz), 7.14-7.36 (9H, m), 6.52 (1H, u, J=7.4 Hz), 5.77 (1H, br-s), 4.26 (1H, m), 3.20 (1H, m), 2.39 (1H, m), 1.50-2.04 (5H, m). LCMS (ES$^+$) Retention time 2.68 minutes, 356 (MH)$^+$.

EXAMPLE 7

Phenyl-[4-(2-Phenyl-piperidin-1-yl)-pyrimidin-2-yl]-amine

Intermediate 16, (0.20 g, 0.73 mmol) and aniline (0.08 g, 0.80 mmol) were reacted together following the procedure detailed for the compound of Example 6, which gave the title compound as a white solid (0.22 g, 82%).

δHNMR (d$_3$ MeOD): 7.68 (1H, d, J=7.5 Hz), 7.06-7.35 (10H, m), 6.47 (1H, d, J=7.5 Hz), 5.79 (1H, br-s), 4.30 (1H, m), 3.20 (1H, m), 2.34 (1H, m), 1.92 (1H, m), 1.53 (4H, m). LCMS (ES) Retention time 2.66 minutes, 331 (MH)$^+$.

EXAMPLE 8

Benzyl-[4-(2-phenyl-piperidin-1-yl)-pyrimidin-2-yl]-amine

Intermediate 16, (0.20 g, 0.73 mmol) in dry ethoxyethanol (10 mL) was treated with sodium bicarbonate (0.31 g, 3.65 mmol) and benzylamine (0.47 g, 4.39 mmol) in one portion at room temperature, under an atmosphere of nitrogen. The suspension was heated to 120° for 48 hr. then cooled, the mixture filtered and the filtrate evaporated in vacuo to a yellow gum. The gum was purified by chromatography (1-20% MeOH in EtOAc-silica) to give the title compound as a beige solid (0.12 g, 49%).

δH NMR (d$_3$ MeOD): 7.60 (1H, d, J=6.3 Hz), 7.24-7.04 (10H, m), 5.90 (1H, d, J=6.3 Hz), 5.68 (1H, br-s), 4.36(2H, dd, J=15.9 and 37.7 Hz), 4.14 (1H, m), 2.85 (1H, m), 2.23 (1H, dd, J=2.0 and 13.48 Hz), 1.37-1.80 (6H, m). LCMS (ES$^+$) Retention time 2.69 minutes, 345 (MH)$^+$.

EXAMPLE 9

(3R)-(3Chloro-phenyl)-[4-(3-phenyl-morpholin-4-yl-pyrimidin-2-yl]-amine

Intermediate 19, (0.18 g, 0.65 mmol) and 3-chloroaniline (0.10 g, 0.72 mmol) were reacted together following the procedure detailed for the compound of Example 6, which gave the title compound as a white solid (0.17 g, 99%).

δH NMR (d$_3$ MeOD): 7.87 (1H, d, J=7.4 Hz), 7.58 (1H, s), 7.15-7.41 (8H, m), 6.61 (1H, d, J=7.5 Hz), 5.65 (1H, s), 4.48 (1H, d, J=12.3 Hz), 4.23 (1H, br-d, J=13.3 Hz), 4.00 (2H, m), 3.74 (1H, m), 3.51 (1H, m). LCMS (ES$^+$) Retention time 2.65 minutes, 367 (MH)$^+$. (Data and experimental are the same for the S-enantiomer)

EXAMPLE 10

(3R)-(2,6-Difluoro-benzyl)-[4-(3-phenyl-morpholin-4-yl)-pyrimidin-2-yl]-amine Intermediate 19, (0.18 g, 0.65 mmol) and 2,6-difluorobenzylamine (0.56 g, 3.93 mmol) were reacted together following the procedure detailed for the compound of Example 8, which gave the title compound as an off-white solid (0.19 g, 76%).

δH NMR (d$_3$ MeOD): 7.64 (1H, d, J=6.5 Hz), 7.24-7.11 (6H, m), 6.77 (2H, m), 6.00 (1H, d, J=6.5 Hz), 5.55 (1H, s), 4.51 (2H, s), 4.35 (1H, d, J=12.0 Hz), 4.06 (1H, m), 3.78 (2H, m), 3.52 (1H, m), 3.19 (1H, m), LCMS (ES$^+$) Retention time 2.54 minutes, 383 (MH)$^+$. (Data and experimental are the same for the S-enantiomer)

EXAMPLE 11

(1R,3R)-(1-Phenyl-ethyl)-[4-(3-phenyl-morpholin-4-yl)-pyrimidin-2-yl]-amine

Intermediate 19, (0.18 g, 0.65 mmol) and (R)-methylbenzylamine (0.47 g, 3.93 mmol) were reacted together following the procedure detailed for the compound of Example 8, which gave the title compound as an off-white solid (0.10 g, 43%).

δH NMR (d$_3$ MeOD): 7.63 (1H, br-s), 7.22-7.11 (10H, m), 5.88 (1H, d, J=6.3 Hz), 5.42 (1H, br-s), 4.91 (1H, dd, J=7.0 and 14.0 Hz), 4.30 (1H, d, J=12.0 Hz), 3.85 (3H, m), 3.40 (1H, m), 3.10 (1H, m), 1.37 (3H, d, J=7.0 Hz). LCMS (ES$^+$) Retention time 2.58 minutes, 361 (MH)$^+$. (Data and experimental are the same for the (S),(S)-enantiomer)

EXAMPLE 12

(3R,1S)(1-Phenyl-ethyl)-[4-(3-phenyl-morpholin-4-yl)-pyrimidin-2-yl]-amine

Intermediate 19, (0.18 g, 0.65 mmol) and (S)-methylbenzylamine (0.47 g, 3.93 mmol) were reacted together following the procedure detailed for the compound of Example 8, which gave the title compound as an off-white solid (0.11 g, 45%).

δH NMR (d$_3$ MeOD): 7.63 (1H, d, J=6.1 Hz), 7.22-7.06 (10H, m), 5.94 (1H, d, J=6.2 Hz), 5.30 (1H, br-s), 4.79 (1H, m), 4.23 (1H, d, J=12.0 Hz), 3.80 (1H, m), 3.77 (1H, m), 3.58 (1H, m), 3.46 (1H, m), 3.11 (1H, m), 1.34 (3H, d, J=6.9 Hz). LCMS (ES$^+$) Retention time 2.59 minutes, 361 (MH)$^+$. (Data and experimental are the same for the (S),(R)-enantiomer)

EXAMPLE 13

3-(4-Fluoro-phenyl)-4-[2-(4-nitro-phenylamino)pyrimidin-4-yl]-piperazin-2-one

Prepared as for the compound of Example 2 from 4-nitroaniline and Intermediate 9.

δH NMR (d$_6$ DMSO): 9.99(1H, br-s), 8.39(1H, br-s), 8.13-8.06(3H, m), 7.86-7.83(2H, d, J=8.81 Hz), 7.51-7.46 (2H, m), 7.25-7.19(2H, m), 6.39(1H, br-s), 5.90(1H, br-s), 3.97(1H, br-s), 3.75-3.70(1H, m), 3.42-3.28(2H, m).

LCMS (ES$^+$) retention time 2.581 minutes 409(MH)$^+$.

EXAMPLE 14

3-(4-Fluoro-phenyl)-4-[2-(4-fluoro-3-trifluoromethyl-phenylamino)-pyrimidin-4-yl]-piperazin-2-one Prepared as for the compound of Example 2 from 4-fluoro-3-trifluoromethylaniline and Intermediate 9.

δH NMR (d$_5$ DMSO): 9.50(1H, s), 8.36(1H, br-s), 8.21 (1H, vbr-s), 8.05(1H, d, J=6.01 Hz), 7.86(1H, vbr-s), 7.47-7.42(2H, m), 7.33(1H, t, J=9.61 Hz), 7.19(2H, t, J=8.99 Hz), 6.29(1H, m), 5.92(1H, br-s), 3.99-3.97(1H, m), 3.68-3.57 (1H, m), 3.50-3.13(2H,-m).

LCMS (ES$^+$) Retention time 2.618 minutes, 450(MH)$^+$.

EXAMPLE 15

(3-Chloro-phenyl)-[4-(2-phenyl-piperazin-1-yl)-pyrimidin-2-yl]-amine

Intermediate 13, (100 mg, 0.21 mmol) in DCM (5 mL) was treated with trifluoroacetic acid (1 mL) and stirred at room temperature for two hours. The reaction mixture was concentrated and partitioned between DCM and saturated sodium hydrogen carbonate solution. The organic phase was separated, dried over sodium sulphate and concentrated in vacuo, to yield the title compound.

δH NMR (d$_6$ DMSO): 9.30(1H, s), 8.04(1H, d, J=6.1 Hz), 7.97(1H, d, J=1.6 Hz), 7.56(1H, d, J=8.26 Hz), 7.40-7.34 (4H, m), 7.29-7.22(2H, m), 6.94-6.91(1H,m), 6.32(1H, d, J=6.18 Hz), 5.58(1H, br-s), 4.23(1H, br-d, J=12.3 Hz), 3.52(1H, d, J=12.6 Hz), 3.23-3.09(2H, m), 3.03(1H, br-d, J=10.3 Hz).

LCMS (ES$^+$) Retention time 1.186 minutes, 366(MH)$^+$.

EXAMPLE 16

4-(2-Benzylaminopyrimidin-4-yl)-3-phenyl-piperazin-2-one

Intermediate 2, (0.2 g, 0.69 mmol) in dioxane (4 mL) was treated with benzylamine (0.090 g, 0.84 mmol) and heated at 100° for 24 hours. The reaction mixture was cooled and concentrated in vacuo and the residue purified by chromatography (3-20% MeOH in DCM-silica) to give the title compound as a white solid (170 mg).

δH NMR (CDCl$_3$): 8.23(1H, s), 7.83(1H, d, J=5.88 Hz), 7.37-7.15(10H, m), 5.98(1H, d, J=5.2 Hz), 5.93(1H, br-s), 4.44-4.32(2H, m), 3.85(1H, br-s), 3.54-3.51(1H, m), 3.31 (2H, s), 3.21-3.15 (1H, m). MS (ES$^+$) 360(MH)$^+$.

EXAMPLE 17

3-Phenyl-4-(2-phenylaminopyrimidin-4-yl)-piperazin-2-one

Intermediate 2, (0.2 g, 0.69 mmol) in dioxane (4 mL) was treated with aniline (0.080 g, 0.86 mmol) and heated at 100° for 24 hours. The reaction mixture was cooled and concentrated in vacuo and the residue purified by chromatography (3-20% MeOH in DCM-silica) to give the title compound as a white solid (185 mg).

δH NMR (CDCl$_3$): 8.48(1H, s), 8.09(1H, br-s), 7.59-7.11 (11H, m), 6.59(1H, br-s), 5.89(1H, br-s), 4.03(1H, br-s), 3.89-3.70(1H, m), 3.56-3.26 (2H, m). MS (ES$^+$) 346(MH)$^+$.

EXAMPLES 18-31

The following general procedure was used to prepare the compounds of Examples 18-31 below. A solution of the appropriate substituted aniline (0.77 mmol) and Intermediate 2 (0.7 mmol) in 2-ethoxyethanol (5 mL) was heated to 120° under nitrogen in a Radleys Carousel reaction station for 16 h. Solvent was removed in vacuo and the crude product purified by chromatography (5-10% MeOH in DCM-silica) to give the appropriate title compound.

EXAMPLE 18

4-[2-(2-Methylphenylamino)pyrimidin-4-yl]-3-phenyl-piperazin-2-one

From o-toluidine to give the title compound as a solid.

δH NMR (d$_6$ DMSO): 8.27(1H, s), 8.17(1H, s), 7.94(1H, d, J=5.7 Hz), 7.42 (1H, m), 7.28-7.32(5H, m), 7.15 (1H, m), 6.95-7.09 (2H, m), 6.16 (1H, d, J=5.7 Hz), 5.89(1H, m), 3.92 (1H, m), 3.65 (1H, m), 3.40 (1H, m), 3.25 (1H, m), 2.18 (3H, s)

LCMS (ES$^+$) Retention time 2.432 minutes, 360 (MH)$^+$.

EXAMPLE 19

4-[2(3-Methylphenylamino)pyrimidin-4-yl]-3-phenyl-piperazin-2-one

From m-toluidine to give the title compound as a solid.

δH NMR (d$_6$ DMSO): 9.10(1H, s), 8.30(1H, s), 8.02(1H, d, J=6 Hz), 7.3-7.5(6H, m), 7.03-7.00(1H, m), 6.98(1H, m), 6.68(1H, d, J=7.5 Hz), 6.13(1H, d, J=6 Hz), 5.80-5.95(1H, m), 3.90 (1H, m), 3.60 (1H, m), 3.30 (1H, m), 3.11 (1H, m), 2.17 (3H, s)

LCMS (ES$^+$) Retention time 2.562 minutes, 360 (MH)$^+$.

EXAMPLE 20

4-[2-(3-Cyanophenylamino)pyrimidin-4-yl]-3-phenyl-piperazin-2-one

From 3-aminobenzonitrile to give the title compound as a solid.

δH NMR (d$_6$ DMSO): 8.60(1H, s), 8.25-8.27(1H, d, J=6.6 Hz), 8.10(1H, s), 7.90(1H, m), 7.30-7.60(6H, m), 6.98(1H, m), 6.67-6.74(1H, m), 6.10-6.15(1H, m), 4.27 (1H, m), 4.0 (1H, m), 3.50 (2H, br-m), 3.10 (1H, m)

LCMS (ES$^+$) Retention time 2.309 minutes, 371 (MH)$^+$.

EXAMPLE 21

4-[2-(3-Nitrophenylamino)pyrimidin-4-yl]-3-phenyl-piperazin-2-one

From 3-nitroaniline to give the title compound as a solid.

δH NMR (d$_6$ DMSO): 9.50(1H, s), 8.10(1H, s), 8.15 (1H, br-s), 7.90(1H, d, J=5.5 Hz), 7.76(1H, dd, J=8.2, 1.0 Hz), 7.52(1H, m), 7.28-7.09(6H, m), 6.12(1H, d, J=5.5 Hz), 5.75(1H, br-m), 3.90 (1H, m), 3.70 (1H, m), 3.30 (1H, m), 3.10 (1H, m)

LCMS (ES$^+$) Retention time 2.514 minutes, 393 (MH)$^+$.

EXAMPLE 22

4-[2-(4-Cyano-phenylamino)pyrimidin-4-yl]-3-phenyl-piperazin-2-one

From p-aminobenzonitrile to give the title compound as a solid.

δH NMR (d$_6$ DMSO): 9.8(1H, s), 8.34(1H, s), 8.1-8.14 (1H, m), 7.30-7.40(5H, m), 7.0 (3H, m), 6.83-6.98(1H, m), 6.50(1H, m), 5.88(1H, m), 3.90(1H, m), 3.60(1H, m), 3.50 (2H, br-m)

LCMS (ES$^+$) Retention time 2.511 minutes, 371 (MH)$^+$.

EXAMPLE 23

4-[2-(4-Methoxyphenylamino)pyrimidin-4yl]-3-phenyl-piperazin-2-one

From p-anisidine to give the title compound as a solid.

δH NMR (d6 DMSO): 9.7(1H, s), 8.26(1H, s), 7.84(1H, d, J=6 Hz), 7.0-7.30(3H, br-m), 6.93(2H, m), 6.80(2H, d, J=9 Hz), 6.56(2H, d, J=5 Hz), 6.26(1H, d, J=6 Hz) 5.73(1H, m), 3.80 (1H, m), 3.60 (1H, m), 3.57 (3H, s), 3.30 (2H, br-m).

LCMS (ES$^+$) Retention time 2.254 minutes, 376 (MH)$^+$.

EXAMPLE 24

4-[2-(2-Methoxyphenylamino)pyrimidin-4-yl]-3-phenyl-piperazin-2-one

From o-anisidine to give the title compound as a solid.

δH NMR (CDCl$_3$): 8.15(1H, d, J=7 Hz), 7.95(1H, d, J=6 Hz), 7.19-7.46(6H, m), 6.90(3H, m), 6.85(1H, m), 5.87-5.89 (2H, m), 4.10 (1H, br-m), 3.95 (3H, s), 3.90 (1H, br-m), 3.40 (2H, br-m)

LCMS (ES$^+$) Retention time 2.286 minutes, 376 (MH)$^+$.

EXAMPLE 25

4-[2-(3-Methoxy-phenylamino)pyrimidin-4-yl]-3-phenyl-piperazin-2-one

From m-anisidine to give the title compound as a solid.

δH NMR (d$_6$ DMSO): 8.40 (1H, s), 8.10(1H, s), 7.40(6H, br-m), 7.15(2H, m), 7.10(1H, m), 6.80(1H, m), 6.40(1H, m), 4.0(1H, m) 3.90(1H, m), 3.68 (3H, s), 3.4 (2H, m)

LCMS (ES$^+$) Retention time 2.295 minutes, 376 (MH)$^+$.

EXAMPLE 26

4-[2-(3,4,5-trimethoxyphenylamino)pyrimidin-4-yl]-3-phenyl-piperazin-2-one

From 3,4,5-trimethoxyaniline to give the title compound as a solid.

δH NMR (d$_6$ DMSO): 9.4(1H, s), 8.30(1H, d, J=6 Hz), 7.75 (5H, m), 7.50(2H, s), 6.50(1H, s), 4.30 (1H, m), 4.05(6H, s), 3.95 (3H, s), 3.75 (2H, m), 3.50(1H, m)

LCMS (ES$^+$) Retention time 2.257 minutes, 436 (MH)$^+$.

EXAMPLE 27

4-[2-(4Chlorophenylamino)pyrimidin-4-yl]-3-phenyl-piperazln-2-one

From p-chloroaniline to give the title compound as a solid.

δH NMR (d$_6$ DMSO): 9.1(1H, s), 8.15(1H, s), 7.80 (1H, d, J=6 Hz), 7.30 (2H, m), 7.30-7.10(5H, m), 6.90(2H, m), 5.90(1H, d, J=6 Hz), 5.60(1H, d, J=6 Hz), 5.60(1H, m), 3.70(1H, br-m), 3.5 (1H, br-m), 3.25(1H, m).

LCMS (ES$^+$) Retention time 2.385 minutes, 380 (MH)$^+$.

EXAMPLE 28

4-[2(3-Chlorophenylamino)pyrimidin-4-yl]-3-phenyl-piperazin-2-one

From m-chloroaniline to give the title compound as a solid.

δH NMR (d$_6$ DMSO): 9.3(1H, s), 8.25(1H, s), 8.15(1H, d, J=6 Hz), 7.80(1H, s), 7.25-7.5(6H, m), 6.95(1H, m), 6.80 (1H, s), 6.25(1H, d, J=6 Hz), 6.05(1H, m), 3.90 (1H, m), 3.70 (1H, m), 3.25(1H, m)

LCMS (ES$^+$) Retention time 2.404 minutes, 380 (MH)$^+$.

EXAMPLE 29

4-[2-(3-Fluorophenylamino)pyrimidin-4-yl]-3-phenyl-piperazin-2-one

From m-fluoroaniline to give the title compound as a solid.

δH NMR (d$_6$ DMSO): 9.1(1H, s), 8.10(1H, s), 7.90(1H, d, J=6 Hz), 7.50(1H, m), 7.0-7.25(6H, br-m), 6.95(1H, m), 6.50(1H, m), 6.15(1H, d, J=6 Hz), 5.90(1H, m), 3.75(1H, m), 3.55(1H, m) 3.25(2H, m)

LCMS (ES$^+$) Retention time 2.518 minutes, 364 (MH)$^+$.

EXAMPLE 30

4-[2-(2-Fluorophenylamino)pyrimidin-4-yl]-3-phenyl-piperazin-2-one

From o-fluoroaniline to give the-title compound as a solid.

δH NMR (d$_6$ DMSO): 8.47(1H, s), 8.30(1H, s), 8.00 (1H, d, J=6 Hz), 7.70(1H, m), 7.37-7.30(4H, m), 7.05(2H, m), 6.25(1H, d, J=6 Hz), 5.95(1H, m), 3.90(1H, m), 3.66(1H, m), 3.20 (2H, br-m)

LCMS (ES$^+$) Retention time 2.415 minutes, 364 (MH)$^+$.

EXAMPLE 31

4-[2-(4-Fluorophenylamino)pyrimidin-4-yl]-3-phenyl-piperazin2-one

From p-fluoroaniline to give the title compound as a solid.

δH NMR (d$_6$ DMSO): 9.97(1H, s), 8.42(1H, s), 8.01 (1H, d, J=6 Hz), 7.36-7.41(5H, m), 7.35(1H, m), 6.90-6.98(2H, m), 6.77(1H, d, J=6 Hz), 5.80-5.95(1H, m), 3.90 (1H, m), 3.80(1H, m), 3.30 (2H, br-m)

LCMS (ES$^+$) Retention time 2.296 minutes, 364 (MH)$^+$

EXAMPLES 32-86

The compounds of Examples 32-86 were prepared according to the following procedure.

The appropriate chloropyrimidine and the appropriate amine with sodium hydrogen carbonate (5 equivalents) were dissolved in ethoxyethanol (0.5 mL) and heated at 120° for two days in a Zinser block. After cooling the reaction was diluted with DMSO and filtered, the filtrate was purified by HPLC to yield the appropriate title compound.

EXAMPLE 32

4-[2-(1,3-Dimethyl-butylamino)-pyrimidin-4-yl]-3-phenyl-piperazin-2-one

Prepared as above using Intermediate 2 and 1,3-dimethyl-butylamine.

LCMS (ES$^+$) Retention time 2.41 minutes, 354 (MH)$^+$

EXAMPLE 33

3-Phenyl-4-[2-(3,3,3-trifluoro-propylamlno)-pyrimidin-4-yl]-piperazin-2-one

Prepared as above using Intermediate 2 and 3,3,3-trifluoro-propylamine.

LCMS (ES$^+$) Retention time 2.26 minutes, 366 (MH)$^+$.

EXAMPLE 34

4-[2-(3-Methoxy-propylamino)-pyrimidin-4-yl]-3-phenyl-piperazin-2-one

Prepared as above using Intermediate 2 and 3-methoxy-propylamine.

LCMS (ES$^+$) Retention time 2.08 minutes, 342 (MH)$^+$.

EXAMPLE 35

4-[2-(3-Isopropoxy-propylamino)-pyrimidin-4-yl]-3-phenyl-piperazin-2-one

Prepared as above using Intermediate 2 and 3-isopropoxy-propylamine.

LCMS (ES$^+$) Retention time 2.28 minutes, 370(MH)$^+$.

EXAMPLE 36

4-(2-Allylamino-pyrimidin-4-yl)-3-phenyl-piperazin-2-one

Prepared as above using Intermediate 2 and allylamine.

LCMS (ES$^+$) Retention time 2.11 minutes, 310(MH)$^+$.

EXAMPLE 37

4-[2-(Cyclopropylmethyl-amino)-pyrimidin-4-yl]-3-phenyl-piperazin-2-one

Prepared as above using Intermediate 2 and cyclopropylmethylamine.

LCMS (ES$^+$) Retention time 2.22 minutes, 324 (MH)$^+$.

EXAMPLE 38

(3R)-[4-(3-Phenyl-morpholin-4-yl)-pyrimidin-2-yl]-thiophen-2-ylmethyl-amine

Prepared as above using Intermediate 19 and 2-aminomethyl-thiophene.

LCMS (ES$^+$) Retention time 2.48 minutes, 353 (MH)$^+$.

EXAMPLE 39

4-[2-(2-Methoxy-ethylamino)-pyrimidin-4-yl]-3-phenyl-piperazin-2-one

Prepared as above using Intermediate 2 and 2-methoxy-ethylamine.

LCMS (ES$^+$) Retention time 1.77 minutes, 328 (MH)$^+$.

EXAMPLE 40

4-(2-Isobutylamino-pyrimidin-4-yl)-3-phenyl-piperazin-2-one

Prepared as above using Intermediate 2 and isobutylamine.

LCMS (ES$^+$) Retention time 2.28 minutes, 326 (MH)$^+$.

EXAMPLE 41

{4-[4-(3-Oxo-2-phenyl-piperazin-1-yl)-pyrimidin-2-ylamino]-butyl}-carbamic acid tert-butyl ester Prepared as above using Intermediate 2 and tert-butyloxycarbonyl-1,4-diaminobutane
LCMS (ES$^+$) Retention time 2.37 minutes, 441 (MH)$^+$.

EXAMPLE 42

4-(2-Pentylamino-pyrimidinyl)-3-phenyl-piperazin-2-one

Prepared as above using Intermediate 2 and pentylamine.
LCMS (ES$^+$) Retention time 2.36 minutes, 340 (MH)$^+$.

EXAMPLE 43

4-(2-Cyclopentylamino-pyrimidin-4-yl)-3-phenyl-piperazin-2-one

Prepared as above using Intermediate 2 and cyclopentylamine.
LCMS (ES$^+$) Retention time 2.28 minutes, 338 (MH)$^+$.

EXAMPLE 44

4-[2-(3-Methyl-butylamino)-pyrimidin-4-yl]-3-phenyl-piperazin-2-one

Prepared as above using Intermediate 2 and 3-methyl-butylamine.
LCMS (ES$^+$) Retention time 2.35 minutes, 340 ((MH)$^+$.

EXAMPLE 45

(3R)-(2,3-Difluoro-benzyl)-[4-(3-phenyl-morpholin-4-yl)-pyrimidin-2-yl]-amine

Prepared as above using Intermediate 19 and 2,3-difluorobenzylamine.
LCMS (ES$^+$) Retention time 2.52 minutes, 383 (MH)$^+$.

EXAMPLE 46

3-Phenyl-4-[2-(3-phenyl-propylamino)-pyrimidin-4-yl]-piperazin-2-one

Prepared as above using Intermediate 2 and 3-phenyl-1-propylamine.
LCMS (ES$^+$) Retention time 2.42 minutes, 388 (MH)$^+$.

EXAMPLE 47

3-Phenyl-4-[2-(4-phenyl-butylamino)-pyrimidin-4-yl]-piperazin-2-one

Prepared as above using Intermediate 2 and 4-phenyl-butylamine.
LCMS (ES$^+$) Retention time 2.48 minutes, 402 (MH)$^+$.

EXAMPLE 48

4-[2-(1-Methyl-butylamino)-pyrimidin-4-yl]-3-phenyl-piperazin-2-one

Prepared as above using Intermediate 2 and 1-methyl-butylamine.
LCMS (ES$^+$) Retention time 2.34 minutes,340 (MH)$^+$.

EXAMPLE 49

4-(2-Phenethylamino-pyrimidin-4-yl)-3-phenyl-piperazin-2-one

Prepared as above using Intermediate 2 and 2-phenethylamine.
LCMS (ES$^+$) Retention time 2.35 minutes, 374 (MH)$^+$.

EXAMPLE 50

(3R)Indan-1-yl-[4-(3-phenyl-morpholin-4-yl)-pyrimidin-2-yl]-amine

Prepared as above using Intermediate 19 and indan-1-ylamine.
LCMS (ES$^+$) Retention time 2.57 minutes, 373 (MH)$^+$.

EXAMPLE 51

4-{2-[2-(4-Hydroxy-phenyl)-ethylamino]-pyrimidin-4-yl}-3-phenyl-piperazin-2-one

Prepared as above using Intermediate 2 and 2-(4-Hydroxy-phenyl)-ethylamine.
LCMS (ES$^+$) Retention time 2.17 minutes, 390 (MH)$^+$.

EXAMPLE 52

4-(2-Cyclobutylamino-pyrimidin-4-yl)-3-phenyl-piperazin-2-one

Prepared as above using Intermediate 2 and cyclo-butylamine.
LCMS (ES$^+$) Retention time 2.21 minutes, 324 (MH)$^+$.

EXAMPLE 53

4-[2-(2-Methyl-butylamino)-pyrimidin-4-yl]-3-phenyl-piperazin-2-one

Prepared as above using Intermediate 2 and 2-methyl-butylamine.
LCMS (ES$^+$) Retention time 2.34 minutes, 340 (MH)$^+$.

EXAMPLE 54

4-{2-[2(5-Methoxy-1H-indol-3-yl)-ethylamino]-pyrimidin-4-yl}-3-phenyl-piperazin-2-one Prepared as above using Intermediate 2 and 2-(5-methoxy-1H-indol-3-yl)-ethylamine.
LCMS (ES$^+$) Retention time 2.33 minutes, 443 (MH)$^+$.

EXAMPLE 55

4-(2-[2-(1H-Indol-3-yl)-ethylamino]-pyrimidin-4-yl)-3-phenyl-piperazin-2-one

Prepared as above using Intermediate 2 and 2-(1H-indol-3-yl)-ethylamine.
LCMS (ES$^+$) Retention time 2.35 minutes, 413 (MH)$^+$.

EXAMPLE 56

4-[2-(2-Diethylamino-ethylamino)-pyrimidin-4-yl]-3-phenyl-piperazin-2-one

Prepared as above using Intermediate 2 and N,N-diethylethylenediamine.
LCMS (ES$^+$) Retention time 0.87 minutes, 369 (MH)$^+$.

EXAMPLE 57

(3S)-Benzo[b]thiophen-3-ylmethyl-[4-(3-phenyl-morpholin-4-yl)-pyrimidin-2-yl]-amine Prepared as above using Intermediate 19(S) and benzo[b]thiophene-3-yl methylamine.
LCMS (ES$^+$) Retention time 2.64 minutes, 403 (MH)$^+$.

EXAMPLE 58

(3S)-[4-(3-Phenyl-morpholin-4-yl)-pyrimidin-2-yl]-(1,3,5-trimethyl-1H-pyrazol-4-ylmethyl)-amine Prepared as above using Intermediate 19(S) and 1,3,5-trimethyl-1H-pyrazol-4-ylmethylamine.
LCMS (ES$^+$) Retention time 2.36 minutes, 379 (MH)$^+$.

EXAMPLE 59

(3S)-2,4-Dichloro-benzyl)-[4-(3-Phenyl-morpholin-4-yl)pyrimidin-2-yl]-amine

Prepared as above using Intermediate 19(S) and 2,4-dichlorobenzyl amine.
LCMS (ES$^+$) Retention time 2.68 minutes, 415 (MH)$^+$.

EXAMPLE 60

(3S)-(1-Methyl-1H-pyrrol-2-ylmethyl)-[4-(3-phenyl-morpholin-4-yl)-pyrimidin-2-yl]-amine Prepared as above using Intermediate 19(S) and 1-methyl-1H-pyrrol-2-ylmethylamine.
LCMS (EC$^+$) Retention time 2.48 minutes, 350 (MH)$^+$.

EXAMPLE 61

(3S)-[4-(3-Phenyl-morpholin-4-yl)-pyrimidin-2-yl]-(1,2,3,4-tetrahydro-naphthalen-1-yl)-amine Prepared as above using Intermediate 19(S) and (1,2,3,4-tetrahdro-naphthalen-1-yl)amine.
LCMS (ES$^+$) Retention time 2.67 minutes, 387 (MH)$^+$.

EXAMPLE 62

(3S)-Indan-1-yl-[4-(3-phenyl-morpholin-4-yl)pyrimidin-2-yl]-amine

Prepared as above using Intermediate 19(S) and indan-1-ylamine.
LCMS (ES$^+$) Retention time 2.63 minutes, 373 (MH)$^+$.

EXAMPLE 63

(3S)-(2-Chloro-benzyl)-[4-(3-phenyl-morpholin-4-yl)-pyrimidin-2-yl]-amine

Prepared as above using Intermediate 19(S) and 2-chlorobenzylamine.
LCMS (ES$^+$) Retention time 2.59 minutes, 381 (MH)$^+$.

EXAMPLE 64

(3S)-(2,4-Dichloro-benzyl)-[4(3-phenyl-morpholin-4yl)-pyrimidin-2-yl]-amine

Prepared as above using Intermediate 19(S) and 2,4-dichlorobenzylamine.
LCMS (ES$^+$) Retention time 2.68 minutes, 415 (MH)$^+$.

EXAMPLE 65

(3S)-(2-Methoxy-benzyl)-[4-(3-phenyl-morpholin-4-yl)-pyrimidin-2-yl]-amine

Prepared as above using Intermediate 19(S) and 2-methoxybenzylamine.
LCMS (ES$^+$) Retention time 2.57 minutes, 377 (MH)$^+$.

EXAMPLE 66

(3S)-(2-Methyl-benzyl)-[4-(3-phenyl-morpholin-4-yl)-pyrimidin-2-yl]-amine

Prepared as above using Intermediate 19(S) and 2-methylbenzylamine.
LCMS (ES$^+$) Retention time 2.59 minutes, 361 (MH)$^+$.

EXAMPLE 67

(3S)-(2,5-Difluoro-benzyl)-[4(3-phenyl-morpholin-4-yl)-pyrimidin-2-yl]-amine

Prepared as above using Intermediate 19(S) and 2,5-difluorobenzylamine.
LCMS (ES$^+$) Retention time 2.55 minutes, 383 (MH)$^+$.

EXAMPLE 68

(3S)-[4-(3-Phenyl-morpholin-4-yl)-pyrimidin-2-yl]-(2-trifluoromethyl-benzyl)-amine Prepared as above using Intermediate 19(S) and 2-trifluoromethylbenzylamine.
LCMS (ES$^+$) Retention time 2.64 minutes, 415 (MH)$^+$.

EXAMPLE 69

(3S)-(2-Chloro-6-fluoro-benzyl)-[4-(3-phenyl-morpholin-4-yl)-pyrimidin-2-yl]-amine Prepared as above using Intermediate 19(S) and 2-chloro-6-fluorobenzylamine.
LCMS (ES$^+$) Retention time 2.59 minutes, 399 (MH)$^+$.

EXAMPLE 70

(3S)-(2,3-Dichloro-benzyl)-[4-(3-phenyl-morpholin-4-yl)pyrimidin-2-yl]-amine

Prepared as above using Intermediate 19(S) and 2,3-dichlorobenzylamine.
LCMS (ES$^+$) Retention time 2.66 minutes, 415 (MH)$^+$.

EXAMPLE 71

(3S)-(2Chloro-6-methyl-benzyl)-[4-(3-phenyl-morpholin-4-yl)-pyrimidin-2-yl]-amine Prepared as above using Intermediate 19(S) and 2-chloro-6-methylbenzylamine.
LCMS (ES$^+$) Retention time 2.66 minutes, 395 (MH)$^+$.

EXAMPLE 72

(3S)-(4-Fluoro-2-trifluoromethyl-benzyl)-[4-(3-phenyl-morpholin-4-yl)-pyrimidin-2-yl]-amine Prepared as above using Intermediate 19(S) and 4-fluoro-2-trifluoromethylbenzylamine.
LCMS (ES$^+$) Retention time 2.67 minutes, 433 (MH)$^+$.

EXAMPLE 73

(3S)(2,3-Difluoro-benzyl)[4-(3-Phenyl-morpholin-4-yl)-pyrimidin-2-yl]-amine

Prepared as above using Intermediate 19(S) and 2,3-difluorobenzylamine.
LCMS (ES$^+$) Retention time 2.56 minutes, 383 (MH)$^+$.

EXAMPLE 74

(3S)(2,3-Dimethyl-benzyl)-[4-(3-Phenyl-morpholin-4-yl)-pyrimidin-2-yl]-amine

Prepared as above using Intermediate 19(S) and 2,3-dimethylbenzylamine.
LCMS (ES$^+$) Retention time 2.65 minutes, 375 (MH)$^+$.

EXAMPLE 75

(3S)(2-Nitro-benzyl)-[4-(3-phenyl-morpholin-4-yl)-pyrimidin-2-yl]-amine

Prepared as above using Intermediate 19(S) and 2-nitrobenzyl amine.
LCMS (ES$^+$) Retention time 2.51 minutes, 392 (MH)$^+$.

EXAMPLE 76

(3S)-[4-(3-Phenyl-morpholin-4-yl)-pyrimidin-2-yl](2,3,4-trifluoro-benzyl)-amine

Prepared as above using Intermediate 19(S) and 2,3,4-trifluorobenzylamine.
LCMS (ES$^+$) Retention time 2.60 minutes, 401(MH)$^+$.

EXAMPLE 77

(3S)-[4(3-Phenyl-morpholin-4-yl)-pyrimidin-2-yl]-(2,3,6-trifluoro-benzyl)-amine

Prepared as above using Intermediate 19(S) and 2,3,6-trifluorobenzylamine.
LCMS (ES$^+$) Retention time 2.56 minutes, 401 (MH)$^+$.

EXAMPLE 78

(3S)-(2-Methylsulfanyl-benzyl)-[4-(3-Phenyl-morpholin-4-yl)-pyrimidin-2-yl]-amine Prepared as above using Intermediate 19(S) and 2-methylsulphanyl-benzylamine.
LCMS (ES$^+$) Retention time 2.60 minutes, 393 (MH)$^+$.

EXAMPLE 79

(3S)-(6-Chloro-2-fluoro-3-methyl-benzyl)-[4-(3-phenyl-morpholin-4-yl)-pyrimidin-2-yl]-amine Prepared as above using Intermediate 19(S) and 6-chloro-2-fluoro-3-methylbenzylamine.
LCMS (ES$^+$) Retention time 2.66 minutes, 413 (MH)$^+$.

EXAMPLE 80

(3S)-[4-(3-Phenyl-morpholin-4-yl)-pyrimidin-2-yl]-(2-piperidin-1-yl-benzyl)-amine Prepared as above using Intermediate 19(S) and 2-piperidinobenzylamine.
LCMS (ES$^+$) Retention time 2.78 minutes, 430 (MH)$^+$.

EXAMPLE 81

(3S)-(2-Fluoro-benzyl)-[4-(3-Phenyl-morpholin-4-yl)-pyrimidin-2-yl]-amine

Prepared as above using Intermediate 19(S) and 2-fluorobenzylamine.
LCMS (ES$^+$) Retention time 2.54 minutes, 365 (MH)$^+$.

EXAMPLE 82

(3S)-Naphthalen-1-ylmethyl-[4-(3-phenyl-morpholin-4-yl)-pyrimidin-2-yl]-amine

Prepared as above using Intermediate 19(S) and naphthalen-1-ylmethylamine.
LCMS (ES$^+$) Retention time 2.65 minutes, 397 (MH)$^+$.

EXAMPLE 83

(3S)-[4-(3-Phenyl-morpholin-4-yl)-pyrimidin-2-yl]-thiophen-2-ylmethyl-amine

Prepared as above using Intermediate 19(S) and thiophen-2-ylmethylamine.
LCMS (ES$^+$) Retention time 2.50 minutes, 353 (MH)$^+$.

EXAMPLE 34

(3s)-(3-Methoxy-benzyl)-[4-(3-phenyl-morpholin-4-yl)-pyrimidin-2-yl]-amine

Prepared as above using Intermediate 19(S) and 3-methoxybenzylamine.
LCMS (ES$^+$) Retention time 2.54 minutes, 377 (MH)$^+$.

EXAMPLE 85

(3S)-(4-Chloro-benzyl)-[4-(3-phenyl-morpholin-4-yl)-pyrimidin-2-yl]-amine

Prepared as above using Intermediate 19(S) and 4-chlorobenzylamine.
LCMS (ES$^+$) Retention time 2.61 minutes, 381 (MH)$^+$.

EXAMPLE 86

(3S)-[4(3-Phenyl-morpholin-4-yl)-pyrimidin-2-yl]-(3-trifluoromethyl-benzyl)-amine Prepared as above using Intermediate 19 and 3-trifluoromethylbenzylamine.
LCMS (ES$^+$) Retention time 2.65 minutes, 415 (MH)$^+$.

EXAMPLE 87

(3RS,1R)-3-(-Phenyl-4-[2-(1(R)-phenyl-ethylamino)-pyrimidin-4-yl]-piperazin-2-one A solution of Intermediate 2, (200 mg, 0.69 mmol) in 2-ethoxyethanol (1.5 mL) was treated with (R)-α-methylbenzylamine (441 µL, 3.47 mmol) and sodium bicarbonate (291 mg, 3.47 mmol). The reaction mixture was heated at 120° for 30 hours, HPLC analysis showed the reaction to be complete. After cooling the mixture was partitioned between DCM and water (20 mL each), and further extracted with DCM (20 mL). The combined organic fractions were dried (MgSO$_4$) filtered and concentrated in vacuo. The residue was slurried with DCM and the resulting white solid collected by filtration to give the title compound, 126 mg (49%).
δHNMR (d$_3$-MeOD): 7.63-7.60 (1H, m); 7.25-6.92 (10H, m); 5.82-5.80 (2H, m); 4.84-4.68 (1H, m); 3.71-3.65 (1H, m); 3.44-3.16 (3H, m); 1.29 and 1.22 diastereomers (3H total, both d, J=7.0 Hz).
LCMS (ES$^+$) Retention time 2.31 mins 374 (MH)$^+$.

EXAMPLE 88

(3RS,1S)-3-Phenyl-4-[2-(1(S)-Phenyl-ethylamino)-pyrimidin-4-yl]-piperazin-2-one

Prepared using Intermediate 2 and (S)-α-methylbenzylamine according to the method of Example 87. HPLC after 21 hours showed reaction to be complete. The title compound was obtained as a white solid 115 mg (45%)
δH NMR (d$_6$-DMSO): 8.06 (1H, s), 7.63 (1H, d, J6.0 Hz); 7.21-6.98 (11H, m); 5.78 (1H, d, J6.0 Hz); 4.82 (1H, s); 3.75-3.65 (1H, m); 3.36-3.30 (1H, m); 3.11-3.01 (2H, m); 1.23-1.15 (3H, m).
LCMS (ES$^+$) Retention time 2.32 mins 374 (MH)$^+$.

EXAMPLE 89

(3R*,1R)-3-Phenyl-4-[2-(1(R)-phenyl-ethylamino)pyrimidin-4-yl]-piperazin-2-one

The starting mixture of isomers was obtained as described in Example 87. 60 mgs of the mixture was subjected to repeat flash column chromatography to give the title compound as a single diastereomer 18 mg (60% recovery after chromatography).
δH NMR (d$_3$-MeOD): 7.69 (1H, d, J=6.2 Hz); 7.20-7.00 (10H, m); 6.10 (1H, s); 5.89 (1H, d, J6.2 Hz); 4.90 (1H, q, J=7.0 Hz); 3.79-3.72 (1H, m); 3.44-3.36 (1H, m); 3.20-3.13 (2H, m); 1.37 (3H, d, J=7.0 Hz).
LCMS (ES$^+$) Retention time 2.36 mins 374 (MH)$^+$.

EXAMPLE 90

(3R*.1R)-3-Phenyl-4-[2-(1-phenyl-ethylamino)-pyrimidinyl-4-yl]-piperazin-2-one

To a degassed solution of Intermediate 21 (260 mg, 0.575 mmol) in MeOH (20 mL) and DCM (10 mL) was added 10% palladium on charcoal (100 mg). The mixture was stirred under an atmosphere of hydrogen for 2 hr. The mixture was filtered through Celite® and concentrated in vacuo. The residue was dissolved in 1% MeOH:DCM and washed with saturated sodium bicarbonate solution, dried over magnesium sulphate and concentrated in vacuo. Column chromatography (5-40% of (10% MeOHl/THF) into DCM-silica) yielded the title compound (36 mg).
δH NMR (d$_3$ MeOD): 7.73 (1H, d, J=6.2 Hz), 7.38-7.15 (10H, m), 7.10 (1H, m), 5.91 (1H, d, J=6.2 Hz), 4.80 (2H, m), 3.80 (1H, m), 3.50 (1H, m), 3.35 (2H, m), 1.32 (3H, d, J=7.0 Hz).
LCMS (ES$^+$) RT 2.357 minutes, 374 (MH)$^+$.

EXAMPLE 91

4-[2-(1-Methyl-1-phenyl-ethylamino)pyrimidinyl-4yl]-3-phenyl-piperazin-2-one

The title compound (22 mg) was prepared in a similar manner to the compound of Example 90, from cumylamine (550 mg, 4.08 mmol) and Intermediate 2 (300 mg, 0.816 mmol).
δH NMR (D$_6$ DMSO): 7.85 (1H, br-s), 7.53 (1H, d, J=5.9 Hz), 7.10-6.80 (10H, m), 6.69 (1H, br-s), 5.67 (1H, d, J=5.9 Hz), 5.40-5.10 (1H, m), 3.40 (1H, m), 3.00 (1H, m), 2.81 (1H, m), 1.37 (3H, s), 1.20 (3H, s).
LCMS (ES$^+$) RT 2.384 minutes, 388 (MH)$^+$.

EXAMPLE 92

4-[2-(2,6-Dichloro-benzylamino)-pyrimidin4-yl]-3-phenyl-piperazin-2-one

To a solution of Intermediate 2, (250 mg, 0.869 mmol) in ethoxyethanol (1.5 mL) were added 2,6-dichlorobenzylamine (760 mg, 4.34 mmol) and sodium bicarbonate (360 mg, 4.34 mmol). The mixture was stirred at 110° for 16 hr. The mixture was diluted with 1% MeOH:DCM and washed with water and brine dried over magnesium sulphate and concentrated in vacuo. Column chromatography (2-15% MeOH-DCM-silica) yielded the title compound (95 mg).

$\delta$H NMR (d$_6$ DMSO): 8.08 (1H, br-s), 7.70 (1H, d, J=5.5 Hz)), 7.27-7.09 (8H, m), 6.57 (1H, br-s), 5.87 (2H, m), 4.46 (2H, s), 3.75 (1H, m), 3.39 (1H, m), 3.04 (2H, m).

LCMS (ES$^+$) RT 2.419 minutes, 428 and 430 (MH)$^+$.

EXAMPLE 93

4-(2-Benzyloxy-pyrimidin-4yl)-3phenyl-piperazin-2-one

To a solution of Intermediate 2, (100 mg, 0.348 mmol) in DMF (1 mL) were added benzylalcohol (75 mg, 0.695 mmol) and cesium carbonate (340 mg, 1.04 mmol). The mixture was stirred at 1000 for 16 hr. The mixture was concentrated in vacuo. The residue was dissolved in 1% MeOH:DCM and washed with water and brine, dried over magnesium sulphate and concentrated in vacuo. Column chromatography (5-40% THF/DCM-silica) followed by preparative HPLC yielded the title compound (8 mg).

$\delta$H NMR (d$_6$ DMSO): 8.10 (1H, br-s), 7.86 (1H, d, J=6.0 Hz), 7.20-7.05 (10H, m), 6.24 (1H, d, J=6.0), 5.65 (1H, m), 5.08 (1H, d, J=12.5 Hz), 5.01 (1H, d, J=12.5 Hz), 3.77 (1H, m), 3.45 (1H, m), 3.25-3.00 (2H, m).

LCMS (ES$^+$) RT 2.449 minutes, 361 (MH)$^+$.

EXAMPLE 94

4-[2-(2,6-Dimethoxy-benzylamino)-pyrimidin-4-yl]-3-phenyl-piperazin-2-one

The title compound (149 mg) was prepared in a similar manner to the compound of Example 92 from 2,6-dimethoxybenzylamine (726 mg, 4.34 mmol) and Intermediate 2, (250 mg, 0.869 mmol).

$\delta$H NMR (d$_6$ DMSO): 8.25 (1H, br-s), 7.82 (1H, br-s), 7.41-7.19 (8H, m), 6.20 (2H, d, J=8.4 Hz), 6.07-5.75 (2H, m), 4.52 (1H, m), 4.35 (1H, m), 3.90 (1H, m), 3.75 (6H, s), 3.55 (1H, m), 3.20 (1H, m).

LCMS (ES$^+$) RT 2.368 minutes, 420 (MH)$^+$.

EXAMPLE 95

4-(2-sec-Butylamino-pyrimidin-4-yl)-3-phenyl-piperazin-2-one

The title compound (134 mg) was prepared in a similar manner to the compound of Example 92 from sec-butylamine (318 mg, 4.34 mmol) and Intermediate 2, (250 mg, 0.869 mmol).

$\delta$H (d$_6$ DMSO): 8.01 (1H, br-s), 7.58 (1H, d, J=5.8 Hz), 7.15-7.03 (5H, m), 6.11 (1H, d, J=5.8 Hz), 5.71 (2H, m), 3.73-3.28 (3H, m), 3.10 (1H, m), 2.95 (1H, m), 1.12-1.28 (2H, m), 0.82 (3H, d, J=6.6 Hz), 0.61 (3H, t, J=7.4 Hz).
LCMS (ES$^+$) RT 2.216 minutes, 326 (MH)$^+$.

EXAMPLES 96-110

The compounds of Examples 96-110 were made by sequential combination of the procedures described for Intermediate 21 and the compound of Example 90, starting from Intermediate 20 and the appropriate amine.

EXAMPLE 96

4-[2-(3-Amino-benzylamino)-pyrimidin-4-yl]-3-phenyl-piperazin-2-one

From Intermediate 20 and 3-aminobenzylamine.
LCMS (ES$^+$) RT 0.613 minutes, 375 (MH)$^+$.

EXAMPLE 97

4-[2-(4-Methoxy-benzylamino)-pyrimidin-4-yl]-3-phenyl-piperazin-2-one

From Intermediate 20 and 4-methoxybenzylamine.
LCMS (ES$^+$) RT 2.249 minutes, 390 (MH)$^+$.

EXAMPLE 98

3-Phenyl-4-{2-[(Pyridin-2-ylmethyl)amino]-pyrimidin-4-yl}-piperazin-2-one

From Intermediate 20 and pyridin-2-yl-methylamine.
LCMS (ES$^+$) RT 0.619 minutes, 361 (MH)$^+$.

EXAMPLE 99

4-[2-(3-Fluoro-5-trifluoromethyl-benzylamino)-pyrimidin-4-yl]-3-phenyl-piperazin-2-one From Intermediate 20 and 3-fluoro-5-trifluoromethylbenzylamine.
LCMS (ES$^+$) RT 2.453 minutes, 446 (MH)$^+$.

EXAMPLE 100

4-[2-(4-Fluoro-3-trifluoromethyl-benzylamino)-pyrimidin-4-yl]-3-phenyl-piperazin-2-one From Intermediate 20 and 4-fluoro-3-trifluoromethylbenzylamine.
LCMS (ES$^+$) RT 2.455 minutes, 446 (MH)$^+$.

EXAMPLE 101

4-[2-2,6-Difluoro-benzylamino)-pyrimidin-4-yl]-3-phenyl-piperazin-2-one

From Intermediate 20 and 2,6-difluorobenzylamine.
LCMS (ES$^+$) RT 2.258 minutes, 396 (MH)$^+$.

EXAMPLE 102

4-[2-(2-Fluoro-benzylamino)-pyrimidin-4-yl]-3-phenyl-piperazin-2-one

From Intermediate 20 and 2-fluorobenzylamine.
LCMS (ES$^+$) RT 2.269 minutes, 378 (MH)$^+$.

EXAMPLE 103

4-[2-(2,3-Dimethyl-benzylamino)-pyrimidin-4-yl]-3-Phenyl-piperazin-2-one

From Intermediate 20 and 2,3-dimethylbenzylamine.
LCMS (ES$^+$) RT 2.396 minutes, 388 (MH)$^+$.

EXAMPLE 104

4-[2-(2,4-Dimethoxy-benzylamino)-pyrimidin-4-yl]-3-phenyl-piperazin-2-one

From Intermediate 20 and 2,4-dimethoxybenzylamine.
LCMS (ES$^+$) RT 2.319 minutes, 420 (MH)$^+$.

EXAMPLE 105

3-Phenyl-4-{2-[(Pyridin-3-ylmethyl)-amino]-pyrimidin-4-yl}-piperazin-2-one

From Intermediate 20 and pyridin-3-yl-methylamine.
LCMS (ES$^+$) RT 3.910 minutes, 36 1(MH)$^+$.

EXAMPLE 106

4-[2-(3,4-Dihydro-1H-isoquinolin-2-yl)-pyrimidin-4-yl]-3-phenyl-piperazln-2-one

From Intermediate 20 and 1,2,3,4-tetrahydroisoquinoline.
LCMS (ES$^+$) RT 2.336 minutes, 386 (MH)$^+$.

EXAMPLE 107

3-Phenyl-4-[2-(1-phenyl-ethylamino)-pyrimidin-4-yl]-piperazin-2-one

From Intermediate 20 and α-methylbenzylamine (racemic).
LCMS (ES$^+$) RT 2.300 minutes, 374 (MH)$^+$.

EXAMPLE 108

4-[2-(3-Methyl-benzylamino)pyrimidin-4-yl]-3-phenyl-piperazin-2-one

From Intermediate 20 and 3-methylbenzylamine.
LCMS (ES$^+$) RT 2.318 minutes, 374 (MH)$^+$.

EXAMPLE 109

4-{2-[(Furan-2-ylmethyl)-amino]-pyrimidin-4-yl}-3-phenyl-piperazin-2-one

From Intermediate 20 and furan-2-yl-methylamine.
LCMS (ES$^+$) RT 2.034 minutes, 350(MH)$^+$.

EXAMPLE 110

3-Phenyl-4-{2-[(thiophen-2-ylmethyl)amino]-pyrimidin-4yl}-piperazin-2-one

From Intermediate 20 and thiophene-2-yl-methylamine.
LCMS (ES$^+$) RT 2.158 minutes, 366(MH)$^+$.

EXAMPLES 111-116

The compounds of Examples 111-116 were prepared according to the following procedure.

Intermediate 2, (250 mgs, 0.87 mmol) was dissolved in dimethoxyethane (3.5 mL) and an inert atmosphere of nitrogen was introduced. To this was added the appropriate boronic acid (1.5 eq, 1.31 mmol), sodium carbonate (2 eq, 230 mg, 1.74 mmol), and palladium (tetrakis)-triphenylphosphine (10 mol %, 100 mg, 0.09 mmol). The resulting suspensions were heated at reflux overnight. TLC or LCMS showed reactions to be complete. The crude reaction mixture was partitioned between DCM (10 mL) and water (3 mL). This mixture was passed through a phase separating filter-frit and organic phase concentrated in vacuo. Purification to yield the title compound was achieved by using the Isco combi-flash.

EXAMPLE 111

3-Phenyl-4-(2-phenyl-pyrimidin-4-yl)-piperazin-2-one

From Intermediate 2 and phenyl boronic acid
δH NMR (d$_3$-MeOD): 8.21 (1H, d, J=6.2 Hz); 8.15-8.13 (2H, m); 7.40-7.21 (8H, m); 6.58 (1H, d, J=6.2 Hz); 6.18 (1H, s); 4.03-4.00 (1H, m); 3.82-3.79 (1H, m); 3.47-3.35 (2H, m). LCMS (ES$^+$) Retention time 2.13 mins 331 (MH)$^+$.

EXAMPLE 112

3-[4-(3Oxo-2-phenyl-piperazin-1-yl)-pyrimidin-2-yl]-benzonitrile

From Intermediate 2 and 3-cyanophenyl boronic acid
δH NMR (d$_3$-MeOD): 8.45-8.43 (2H, m); 8.26 (1H, d, J=6.2 Hz); 7.71-7.69 (1H, m); 7.54-7.50 (1H, m); 7.41-7.39 (2H, m); 7.30-7.20 (3H, m); 6.64 (1H, d, J=6.2 Hz); 6.09 (1H, S); 4.04-4.02 (1H, m); 3.85-3.79 (1H, m); 3.50-3.37 (2H, m). LCMS (ES$^+$) Retention time 2.79 mins 356 (MH)$^+$ and 378 (MNa)$^+$.

EXAMPLE 113

4-[4-(3-Oxo-2-phenyl-piperazin-1-yl)-pyrimidin-2-yl]-benzonitrile

From Intermediate 2 and 4-cyanophenyl boronic acid
δH NMR (d$_3$-MeOD): 8.32 (1H, d, J=8.5 Hz); 3.48-3.37 (2H, m); 8.27 (1H, d, J=6.2 Hz); 7.70-7.68 (2H, m); 7.40-7.21 (5H, m); 6.64 (1H, d, J=6.2 Hz); 6.12 (1H, s); 4.03-4.00 (1H, m); 3.83-3.79 (2H, m).
LCMS (ES$^+$) Retention time 2.80 mins 356 (MH)$^+$ and 378 (MNa)$^+$.

EXAMPLE 114

4-[2-(4-Chloro-phenyl)-pyrimidin-4-yl]-3-phenyl-piperazin-2-one

From Intermediate 2 and 4-chlorophenyl boronic acid.
δH NMR (d$_3$-MeOD): 8.21 (1H, d, J=6.2 Hz); 8.14-8.12 (2H, m); 7.40-7.21 (7H, m); 6.59 (1H, d, J=6.2 Hz); 6.12 (1H, s); 4.03-4.00 (1H, m); 3.83-3.79 (1H, m); 3.37-3.45 (2H, m). LCMS (ES$^+$) Retention time 2.75 mins 365 ($^{35}$Cl, MH)$^+$ and 367 ($^{37}$Cl, MH)$^+$.

EXAMPLE 115

4-[2-(3-Chloro-phenyl)-pyrimidin-4-yl]-3-phenyl-piperazin-2-one

From Intermediate 2 and 3-chlorophenyl boronic acid.
δH NMR (d$_3$-MeOD): 8.23 (1H, d, J=6.2 Hz); 8.13-8.06 (2H, m); 7.41-7.20 (7H, m); 6.61 (1H, d, J=6.2 Hz); 6.11

(1H, s); 4.00-3.96 (1H, m); 3.83-3.79 (1H, m); 3.48-3.37 (2H, m). LCMS (ES$^+$) Retention time 2.99 mins 365 ($^{35}$Cl, MH)$^+$ and 367 ($^{37}$Cl, MH)$^+$.

EXAMPLE 116

4-[2-(1H-Indol-5-yl)-pyrimidin-4yl]-3-phenyl-piperazin-2-one

From Intermediate 2 and 5-indolyl boronic acid.

δH NMR (d$_3$-MeOD): 8.41 (1H, d, J=1.0 Hz); 8.17 (1H, d J6.2 Hz); 7.96 (1H, dd, J8.6. 1.6 Hz); 7.44-7.41 (2H, m); 7.32-7.16 (5H, m); 6.50 (1H, d, J=6.2 Hz); 6.42 (1H, dd, J=3.2, 0.9 Hz); 6.26 (1H, s); 4.07-4.00 (1H, m); 3.83-3.74 (2H, m); 3.51-3.33 (2H, m).

LCMS (ES$^+$) Retention time 2.21 mins 370 (MH)$^+$.

The following assays and animal models can be used to demonstrate the potency and selectivity of the compounds according to the invention. In each assay an IC50 value was determined for each test compound and represents the concentration of compound necessary to achieve 50% inhibition.

Preparation of Activated Human D380 for Inhibitor Assays.

Purification of Human p38α

Human p38α, incorporating an N-terminal (His)6 tag (SEQ ID NO: 1), was expressed in baculovirus-infected High-Five™ cells (Invitrogen) according to the manufacturers instructions. The cells were harvested 72 h post-infection and lysed in phosphate buffered saline (PBS) containing 1% (w/v) β-octylgiucoside and Complete, EDTA-free™ protease inhibitors (Roche Molecular Biochemicals). The lysate was centrifuged at 35000×g for 30 min at 4° C. and the supernatant applied to a NiNTA™ column (Qiagen). Bound protein was eluted by 150 mM imadazole in PBS (after a wash with 15 mM imadazole in PBS) and directly applied to a HiTrap Q™ column (AP Biotech). Bound protein was eluted using a 20 column volume, 0 to 1M NaCl gradient. Fractions containing (His) 6-p38 were aliquotted and stored at −70° prior to their activation.

Preparation of GST-MKK6EE-Containing Lysates

E. coli (BL21 pLysS) expressing the constituitively activated form of human MKK6 fused with an N-terminal glutathione-S-transferase tag (GST-MKK6EE) were harvested by centrifugation and frozen at −70°. Cells were lysed by resuspension in ¹/₁₀th the culture volume of PBS containing Complete, EDTA-free™ protease inhibitors followed by sonication on ice for 4×15 sec. Cell debris was removed by centrifugation at 35,000×g and the resultant supernatant stored in aliquots at −70°.

Activation of (His)6-D38

0.45 mL of purified (His)6-p38 was incubated with 50 μL of the GST-MKK6EE-containing lysate for 30 min at 23° in the presence of 1 mM β-glycerophosphate, 10 mM MgCl$_2$ and 9 mM ATP. The extent of activation was monitored by mass spectrometric detection of the doubly-phosphorylated form of (His)6-p38, which routinely comprised greater than 90% of the final (His)6p38 preparation. The activated (His) 6-p38 was then diluted ×10 in PBS and repurified using the method described above. The concentration of purified, activated (His)6-p38 was measured by UV absorbance at 280 nm using A280,0.1%=1.2 and the preparation stored in aliquots at −70° prior to its use in inhibitor assays.

p38 Inhibition Assays

Inhibition of Phosphorylation of Biotinylated Myelin Basic Protein (MBP)

The inhibition of p38 catalysed phosphorylation of biotinylated MBP is measured using a DELFIA based format. The assay was performed in a buffer comprising, 20 mM HEPES (pH 7.4), 5 mM MgCl$_2$ and 3 mM DTT. For a typical IC50 determination, biotinylated MBP (2.5 μM) was incubated at room temperature in a streptavidin-coated microtitre plate together with activated gst-p38 (10 nM) and ATP (1 μM) in the presence of a range of inhibitor concentrations (final concentration of DMSO is 2 percent). After fifteen minutes the reaction was terminated by the addition of EDTA (75 mM). The microtitre plate was then washed with Tris buffered saline (TBS), prior to the addition of 100 μl of anti-phospho MBP antibody (mouse) together with europium-labeled anti-mouse IgG antibody. After one hour at room temperature the plate was again washed in TBS followed by the addition of Enhancement solution (PerkinElmer Wallac). Fluorescence measurements were performed after a further fifteen minutes at room temperature.

IC50 values are determined from the plot of Log$_{10}$ inhibitor concentration (x-axis) versus percentage inhibition of the fluorescence generated by a control sample in the absence of inhibitor (y-axis).

Purification of Human Peripheral Bood Mononuclear Cells

Peripheral blood mononuclear cells (PBMC) were isolated from normal healthy volunteers. Whole blood was taken by venous puncture using heparinised vacutainers (Becton Dickinson), diluted 1 in 4 in RPMI 1640 (Gibco, UK) and centrifuged at 400 g for 35 min over a Ficoll-paque gradient (Amersham-Pharmacia Biotech, UK). Cells at the interface were removed and washed once followed by a low speed spin (250 g) to remove platelets. Cells were then resuspended in DMEM containing 10% FCS, penicillin 100 units ml$^{-1}$, streptomycin 50 μg ml$^{-1}$ and glutamine 2 mM (Gibco, UK).

Inhibitor Dilutions

Inhibitor stocks (20 mM) were kept as a frozen solution (−20° C.) in DMSO. Serial dilutions of inhibitors were performed in DMSO as 250-times concentrated stocks. Inhibitors were diluted 1 in 250 into tissue culture media, prewarmed to 37° C. and transferred to plates containing PBMC. PBMC and inhibitors were incubated together for 30 mins prior to addition of LPS. Inhibitors used in whole blood assays were prepared according to a different regime. Using the same stock solution serial dilutions of inhibitors were performed in DMSO. Inhibitors were then diluted 1 in 500 straight into whole blood in a volume of 1 μL. Inhibitor was incubated with whole blood for 30 mins prior to the addition of LPS.

LPS Stimulation of PBMC

PBMC were resuspended at a density of 2×10$^5$ cells/well in flat bottomed 96 well tissue culture treated plates. After the addition of inhibitor cells were stimulated with an optimal dose of LPS (E coli strain B5:055, Sigma, at a final concentration of 1 μg ml$^{-1}$) and incubated at 37° C. in 5% CO$_2$/95% air for 18 hours. TNF-α levels were measured from cell free supernatants by sandwich ELISA (BioSource #CHC1751).

LPS Stimulation of Whole Blood

Whole blood was taken by venous puncture using heparinised vacutainers (Becton Dickinson), and 500 μl of blood aliquoted into each well of a 24 well tissue culture treated plate. After the addition of inhibitor cells were stimulated with an optimal dose of LPS (*E coli* strain B5:055, Sigma, at a final concentration of 1 µg ml$^{-1}$) and incubated at 37° C. without $CO_2$ for 18 hours. TNF-α levels were measured from cell free supernatants by sandwich ELISA (BioSource #CHC1751).

Rat LPS Induced TNF Release

Male Lewis rats (180-200 g) are anaesthetised with Isofluor and injected i.v. with LPS* in a volume of 0.5 ml sterile saline. After 90 minutes blood is collected into EDTA tubes for preparation of plasma samples. Plasma is stored at −70° C. prior to assay for TNFα by commercial ELISA.

Rat CIA

Female Lewis rats (180-200 g) are anaesthetised with Isofluor and immunised i.d. at the base of the tail with 2×100 µl of emulsion containing 4 mg/ml bovine collagen II in 0.01M acetic acid and Freund's Incomplete Adjuvant at a ratio of 1:1.

A polyarthetis develops with onset from about 13 days post sensitisation.

The disease is mainly confined to the ankles and is quantified by plethysmometry. Results are expressed as change in paw volume over time.

In the p38 inhibitor assay compounds of the invention have $IC_{50}$ values of around 30 µM and below. In particular compounds of the Examples have $IC_{50}$ values of 5 µM and below with the most active compounds having $IC_{50}$ values of 500 nM and below. The compounds of the invention are clearly potent inhibitors of p38 kinase, especially p38α kinase.

The invention claimed is:

1. A compound of formula (1):

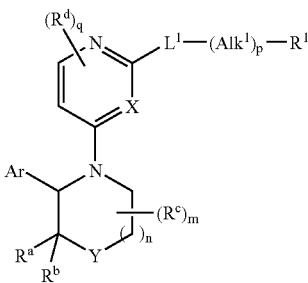

(1)

wherein:
$R^a$ and $R^b$ are each independently a hydrogen atom or a group $R^c$, or $R^a$ and $R^b$ together form an oxo (=O) or thio (=S) group;
X is a N atom;
Y is a —O— or —S— atom or —SO— or —$SO_2$— group or an optionally substituted —$CH_2$— or —NH— group with the proviso that when $R^a$ and $R^b$ together form an oxo (=O) or thio (=S) group, Y is an optionally substituted —$CH_2$— or —NH— group;
$L^1$ is a —NH— group;
p is zero or the integer 1;
$Alk^1$ is an optionally substituted $C_{1-10}$aliphatic or $C_{1-10}$heteroaliphatic chain;
$R^1$ is a hydrogen or halogen atom or a —CN, —$NO_2$ or optionally substituted $C_{3-10}$cycloaliphatic, $C_{7-10}$polycycloaliphatic, $C_{2-10}$heterocycloaliphatic, $C_{6-10}$heteropolycycloaliphatic, $C_{6-12}$aromatic or $C_{1-9}$heteroaromatic group;
n is zero or the integer 1, 2 or 3 with the proviso that when n is zero, Y is an optionally substituted —$CH_2$— group;
Ar is an optionally substituted $C_{6-12}$aromatic or $C_{1-9}$heteroaromatic group;
m is zero or the integer 1, 2 or 3;
$R^c$, which may be present on any carbon or, where available, nitrogen atom in the Y-containing ring, is an oxo (=O) or thio (=S) atom or an atom or group —$(Alk^2)_r(R^5)_s$;
$Alk^2$ is an optionally substituted $C_{1-10}$aliphatic or $C_{1-10}$heteroaliphatic chain;
r is zero or the integer 1;
s is the integer 1, 2 or 3;
$R^5$ is a hydrogen or halogen atom or a hydroxyl (—OH), thiol (—SH), cyano (—CN), —$CO_2R^2$, —$OCO_2R^2$, —$CONR^2R^3$, —$OCONR^2R^3$, —$CSNR^2R^3$, nitro (—$NO_2$), amino (—$NH_2$), —$NHR^2$, —$N(R^2)(R^3)$, —$COR^2$, —$OCOR^2$, —$N(R^3)COR^2$, —$N(R^3)CSR^2$, —$SO_2N(R^2)(R^3)$, —$N(R^2)SO_2R^3$, —$N(R^4)CON(R^2)(R^3)$, —$N(R^4)CSN(R^2)(R^3)$, —$N(R^4)SO_2N(R^2)(R^3)$, $C_{3-11}$cycloaliphatic, $C_{2-10}$heterocycloaliphatic, $C_{6-12}$aromatic or $C_{1-9}$heteroaromatic group;
$R^2$ is a hydrogen atom or an optionally substituted $C_{1-6}$alkyl, $C_{6-12}$aromatic or $C_{1-9}$heteroaromatic group;
$R^3$ is a hydrogen atom or an optionally substituted $C_{1-6}$alkyl group or together with the N atom to which they are attached $R^2$ and $R^3$ alkyl groups are joined to form a heterocyclic ring which may be optionally interrupted by a further —O— or —S— atom or —N($R^2$)— group;

$R^4$ is a hydrogen atom or an optionally substituted $C_{1-6}$alkyl group;

q is zero or the integer 1 or 2;

$R^d$ is a hydrogen or halogen atom or a $C_{1-6}$alkyl, halo$C_{1-6}$alkyl, hydroxyl (—OH), $C_{1-6}$alkoxy, halo$C_{1-6}$alkoxy, thiol (—SH), $C_{1-6}$alkylthio, cyano (—CN), —$CO_2R^6$, —$OCO_2R^6$, —$CONR^6R^7$, —$OCONR^6R^7$, —$CSNR^6R^7$, nitro (—$NO_2$), amino (—$NH_2$), —$NHR^6$, —$N(R^6)(R^7)$, —$COR^6$, —$OCOR^6$, —$N(R^7)COR^6$, —$N(R^7)CSR^6$, —$SO_2N(R^6)(R^7)$, —$N(R^6)SO_2R^7$, —$N(R^8)CON(R^6)(R^7)$, —$N(R^8)CSN(R^6)(R^7)$ or —$N(R^8)SO_2N(R^6)(R^7)$ group;

$R^6$ is a hydrogen atom or an optionally substituted $C_{1-6}$alkyl group;

$R^7$ is a hydrogen atom or an optionally substituted $C_{1-6}$alkyl group or together with the N atom to which they are attached $R^6$ and $R^7$ alkyl groups are joined to form a heterocyclic ring which may be optionally interrupted by a further —O— or —S— atom or —N($R^6$)— group;

$R^8$ is a hydrogen atom or an optionally substituted $C_{1-6}$alkyl group;

or a salt or N-oxide thereof.

2. A compound according to claim 1 in which $R^a$ and $R^b$ are each independently a hydrogen atom or together form an oxo (=O) or thio (=S) group.

3. A compound according to claim 2 in which $R^a$ and $R^b$ together form an oxo (=O) group.

4. A compound according to claim 1 in which Y is a —NH— or —N($CH_3$)— group.

5. A compound according to claim 1 in which n is the interger 1.

6. A compound according to claim 1 in which $R^1$ is a hydrogen atom or an optionally substituted $C_{3-10}$cycloaliphatic, $C_{2-10}$heterocycloaliphatic, $C_{6-12}$aromatic or $C_{1-9}$heteroaromatic group.

7. A compound according to claim 6 in which $R^1$ is an optionally substituted $C_{3-7}$cycloalkyl, $C_{2-7}$heterocycloalkyl or $C_{6-12}$aromatic group.

8. A compound according to claim 7 wherein $R^1$ is an optionally substituted phenyl group.

9. A compound according to claim 1 in which p is the integer 1 and $Alk^1$ is an optionally substituted $C_{1-3}$alkylene chain.

10. A compound according to claim 1 in which m is zero.

11. A compound according to claim 1 in which Ar is an optionally substituted phenyl group.

12. A compound according to claim 11 in which Ar is a phenyl group.

13. A compound which is:
3-Phenyl-4-[2-(3-trifluoromethyl-benzylamino)-pyrimidin-4-yl]-piperazin-2-one;
3-[4-(4-Methyl-3-oxo-2-phenyl-piperazin-1-yl)-pyrimidin-2-ylamino]-benzonitrile;
3-[4-(4-Cyclopropylmethyl-3-oxo-2-phenyl-piperazin-1-yl)-pyrimidin-2-ylamino]-benzonitrile;
3-[4-(4-Benzyl-3-oxo-2-phenyl-piperazin-1-yl)-pyrimidin-2-ylamino]-benzonitrile;
3-[4-(4-Allyl-3-oxo-2-phenyl-piperazin-1-yl)-pyrimidin-2-ylamino]-benzonitrile;
3-[4-(2-Phenyl-piperidin-1-yl)-pyrimidin-2-ylamino]-benzonitrile;
Phenyl-[4-(2-phenyl-piperidin-1-yl)-pyrimidin-2-yl]-amine;
Benzyl-[4-(2-phenyl-piperidin-1-yl)-pyrimidin-2-yl]-amine;
(3R)-(3-Chloro-phenyl)-[4-(3-phenyl-morpholin-4-yl)-pyrimidin-2-yl]-amine;
(3R)-(2,6-Difluoro-benzyl)-[4-(3-phenyl-morpholin-4-yl)-pyrimidin-2-yl]-amine;
(1R,3R)-(1-Phenyl-ethyl)-[4-(3-phenyl-morpholin-4-yl)-pyrimidin-2-yl]-amine;
(3R,1S)-(1-Phenyl-ethyl)-[4-(3-phenyl-morpholin-4-yl)-pyrimidin-2-yl]-amine;
3-(4-Fluoro-phenyl)-4-[2-(4-nitro-phenylamino)-pyrimidin-4-yl]-piperazin-2-one;
3-(4-Fluoro-phenyl)-4-[2-(4-fluoro-3-trifluoromethyl-phenylamino)-pyrimidin-4-yl]-piperazin-2-one;
(3-Chloro-phenyl)-[4-(2-phenyl-piperazin-1-yl)-pyrimidin-2-yl]-amine;
4-(2-Benzylaminopyrimidin-4-yl)-3-phenyl-piperazin-2-one;
3-Phenyl-4-(2-phenylaminopyrimidin-4-yl)-piperazin-2-one;
4-[2-(2-Methylphenylamino)pyrimidin-4-yl]-3-phenyl-piperazin-2-one;
4-[2-(3-Methylphenylamino)pyrimidin-4-yl]-3-phenyl-piperazin-2-one;
4-[2-(3-Cyanophenylamino)pyrimidin-4-yl]-3-phenyl-piperazin-2-one;
4-[2-(3-Nitrophenylamino)pyrimidin-4-yl]-3-phenyl-piperazin-2-one;
4-[2-(4-Cyano-phenylamino)pyrimidin-4-yl]-3-phenyl-piperazin-2-one;
4-[2-(4-Methoxyphenylamino)pyrimidin-4-yl]-3-phenyl-piperazin-2-one;
4-[2-(2-Methoxyphenylamino)pyrimidin-4-yl]-3-phenyl-piperazin-2-one;
4-[2-(3-Methoxy-phenylamino)pyrimidin-4-yl]-3-phenyl-piperazin-2-one;
4-[2-(3,4,5-trimethoxyphenylamino)pyrimidin-4-yl]-3-phenyl-piperazin-2-one;
4-[2-(4-Chlorophenylamino)pyrimidin-4-yl]-3-phenyl-piperazin-2-one;
4-[2-(3-Chlorophenylamino)pyrimidin-4-yl]-3-phenyl-piperazin-2-one;
4-[2-(3-Fluorophenylamino)pyrimidin-4-yl]-3-phenyl-piperazin-2-one;
4-[2-(2-Fluorophenylamino)pyrimidin-4-yl]-3-phenyl-piperazin-2-one;
4-[2-(4-Fluorophenylamino)pyrimidin-4-yl]-3-phenyl-piperazin-2-one;
4-[2-(1,3-Dimethyl-butylamino)-pyrimidin-4-yl]-3-phenyl-piperazin-2-one;
3-Phenyl-4-[2-(3,3,3-trifluoro-propylamino)-pyrimidin-4-yl]-piperazin-2-one;
4-[2-(3-Methoxy-propylamino)-pyrimidin-4-yl]-3-phenyl-piperazin-2-one;
4-[2-(3-Isopropoxy-propylamino)-pyrimidin-4-yl]-3-phenyl-piperazin-2-one;
4-(2-Allylamino-pyrimidin-4-yl)-3-phenyl-piperazin-2-one;
4-[2-(Cyclopropylmethyl-amino)-pyrimidin-4-yl]-3-phenyl-piperazin-2-one;
(3R)-[4-(3-Phenyl-morpholin-4-yl)-pyrimidin-2-yl]-thiophen-2-ylmethyl-amine;
4-(2-Methoxy-ethylamino)-pyrimidin-4-yl]-3-phenyl-piperazin-2-one;
4-(2-Isobutylamino-pyrimidin-4-yl)-3-phenyl-piperazin-2-one;

{4-[4-(3-Oxo-2-phenyl-piperazin-1-yl)-pyrimidin-2-ylamino]-butyl}-carbamic acid tert-butyl ester;
4-(2-Pentylamino-pyrimidin-4-yl)-3-phenyl-piperazin-2-one;
4-(2-Cyclopentylamino-pyrimidin-4-yl)-3-phenyl-piperazin-2-one;
4-[2-(3-Methyl-butylamino)-pyrimidin-4-yl]-3-phenyl-piperazin-2-one;
(3R)-(2,3-Difluoro-benzyl)-[4-(3-phenyl-morpholin-4-yl)-pyrimidin-2-yl]-amine;
3-Phenyl-4-[2-(3-phenyl-propylamino)-pyrimidin-4-yl]-piperazin-2-one;
3-Phenyl-4-[2-(4-phenyl-butylamino)-pyrimidin-4-yl]-piperazin-2-one;
4-[2-(1-Methyl-butylamino)-pyrimidin-4-yl]-3-phenyl-piperazin-2-one;
4-(2-Phenethylamino-pyrimidin-4-yl)-3-phenyl-piperazin-2-one;
(3R)Indan-1-yl-[4-(3-phenyl-morpholin-4-yl)-pyrimidin-2-yl]-amine;
4-{2-[2-(4-Hydroxy-phenyl)-ethylamino]-pyrimidin-4-yl}-3-phenyl-piperazin-2-one;
4-(2-Cyclobutylamino-pyrimidin-4-yl)-3-phenyl-piperazin-2-one;
4-[2-(2-Methyl-butylamino)-pyrimidin-4-yl]-3-phenyl-piperazin-2-one;
4-{2-[2-(5-Methoxy-1H-indol-3-yl)-ethylamino]-pyrimidin-4-yl}-3-phenyl-piperazin-2-one;
4-{2-[2-(1H-Indol-3-yl)-ethylamino]-pyrimidin-4-yl}-3-phenyl-piperazin-2-one;
4-[2-(2-Diethylamino-ethylamino)-pyrimidin-4-yl]-3-phenyl-piperazin-2-one;
(3S)-Benzo[b]thiophen-3-ylmethyl-[4-(3-phenyl-morpholin-4-yl)-pyrimidin-2-yl]-amine;
(3S)-[4-(3-Phenyl-morpholin-4-yl)-pyrimidin-2-yl]-(1,3,5-trimethyl-1H-pyrazol-4-ylmethyl)-amine;
(3S)-(2,4-Dichloro-benzyl)-[4-(3-phenyl-morpholin-4-yl)-pyrimidin-2-yl]-amine;
(3S)-(1-Methyl-1H-pyrrol-2-ylmethyl)-[4-(3-phenyl-morpholin-4-yl)-pyrimidin-2-yl]-amine;
(3S)-[4-(3-Phenyl-morpholin-4-yl)-pyrimidin-2-yl]-(1,2,3,4-tetrahydro-naphthalen-1-yl)-amine;
(3S)-Indan-1-yl-[4-(3-phenyl-morpholin-4-yl)-pyrimidin-2-yl]-amine;
(3S)-(2-Chloro-benzyl)-[4-(3-phenyl-morpholin-4-yl)-pyrimidin-2-yl]-amine;
(3S)-(2,4-Dichloro-benzyl)-[4-(3-phenyl-morpholin-4-yl)-pyrimidin-2-yl]-amine;
(3S)-(2-Methoxy-benzyl)-[4-(3-phenyl-morpholin-4-yl)-pyrimidin-2-yl]-amine;
(3S)-(2-Methyl-benzyl)-[4-(3-phenyl-morpholin-4-yl)-pyrimidin-2-yl]-amine;
(3S)-(2,5-Difluoro-benzyl)-[4-(3-phenyl-morpholin-4-yl)-pyrimidin-2-yl]-amine;
(3S)-[4-(3-Phenyl-morpholin-4-yl)-pyrimidin-2-yl]-(2-trifluoromethyl-benzyl)-amine;
(3S)-(2-Chloro-6-fluoro-benzyl)-[4-(3-phenyl-morpholin-4-yl)-pyrimidin-2-yl]-amine;
(3S)-(2,3-Dichloro-benzyl)-[4-(3-phenyl-morpholin-4-yl)-pyrimidin-2-yl]-amine;
(3S)-(2-Chloro-6-methyl-benzyl)-[4-(3-phenyl-morpholin-4-yl)-pyrimidin-2-yl]-amine;
(3S)-(4-Fluoro-2-trifluoromethyl-benzyl)-[4-(3-phenyl-morpholin-4-yl)-pyrimidin-2-yl]-amine;
(3S)-(2,3-Difluoro-benzyl)-[4-(3-phenyl-morpholin-4-yl)-pyrimidin-2-yl]-amine;
(3S)-(2,3-Dimethyl-benzyl)-[4-(3-phenyl-morpholin-4-yl)-pyrimidin-2-yl]-amine;
(3S)-(2-Nitro-benzyl)-[4-(3-phenyl-morpholin-4-yl)-pyrimidin-2yl]-amine;
(3S)-[4-(3-Phenyl-morpholin-4-yl)-pyrimidin-2-yl]-(2,3,4-trifluoro-benzyl)-amine;
(3S)-[4-(3-Phenyl-morpholin-4-yl)-pyrimidin-2-yl]-(2,3,6-trifluoro-benzyl)-amine;
(3S)-(2-Methylsulfanyl-benzyl)-[4-(3-phenyl-morpholin-4-yl)-pyrimidin-2-yl]-amine;
(3S)-(6-Chloro-2-fluoro-3-methyl-benzyl)-[4-(3-phenyl-morpholin-4-yl)-pyrimidin-2-yl]-amine;
(3S)-[4-(3-Phenyl-morpholin-4-yl)-pyrimidin-2-yl]-(2-piperidin-1-yl-benzyl)-amine;
(3S)-(2-Fluoro-benzyl)-[4-(3-phenyl-morpholin-4-yl)-pyrimidin-2-yl]-amine;
(3S)-Naphthalen-1-ylmethyl-[4-(3-phenyl-morpholin-4-yl)-pyrimidin-2-yl]-amine;
(3S)-[4-(3-Phenyl-morpholin-4-yl)-pyrimidin-2-yl]-thiophen-2-ylmethyl-amine;
(3S)-(3-Methoxy-benzyl)-[4-(3-phenyl-morpholin-4-yl)-pyrimidin-2-yl]-amine;
(3S)-(4-Chloro-benzyl)-[4-(3-phenyl-morpholin-4-yl)-pyrimidin-2-yl]-amine;
(3S)-[4-(3-Phenyl-morpholin-4-yl)-pyrimidin-2-yl]-(3-trifluoromethyl-benzyl)-amine;
(3RS,1R)-3-(-Phenyl-4-[2-(1(R)-phenyl-ethylamino)-pyrimidin-4-yl]-piperazin-2-one;
(3RS,1S)-3-Phenyl-4-[2-(1(S)-phenyl-ethylamino)-pyrimidin-4-yl]-piperazin-2-one;
(3R*,1R)-3-Phenyl-4-[2-(1(R)-phenyl-ethylamino)-pyrimidin-4-yl]-piperazin-2-one;
(3R*,1R)-3-Phenyl-4-[2-(1-phenyl-ethylamino)-pyrimidin-4-yl]-piperazin-2-one;
4-[2-(1-Methyl-1-phenyl-ethylamino)-pyrimidin-4-yl]-3-phenyl-piperazin-2-one;
4-[2-(2,6-Dichloro-benzylamino)-pyrimidin-4-yl]-3-phenyl-piperazin-2-one;
4-(2-Benzyloxy-pyrimidin-4-yl)-3-phenyl-piperazin-2-one;
4-[2-(2,6-Dimethoxy-benzylamino)-pyrimidin-4-yl]-3-phenyl-piperazin-2-one;
4-(2-sec-Butylamino-pyrimidin-4-yl)-3-phenyl-piperazin-2-one;
4-[2-(3-Amino-benzylamino)-pyrimidin-4-yl]-3-phenyl-piperazin-2-one;
4-[2-(4-Methoxy-benzylamino)-pyrimidin-4-yl]-3-phenyl-piperazin-2-one;
3-Phenyl-4-{2-[(pyrimidin-2-ylmethyl)-amino]-pyrimidin-4-yl}-piperazin-2-one;
4-[2-(3-Fluoro-5-trifluoromethyl-benzylamino)-pyrimidin-4-yl]-3-phenyl-piperazin-2-one;
4-[2-(4-Fluoro-3-trifluoromethyl-benzylamino)-pyrimidin-4-yl]-3-phenyl-piperazin-2-one;
4-[2-(2,6-Difluoro-benzylamino)-pyrimidin-4-yl]-3-phenyl-piperazin-2-one;
4-[2-(2-Fluoro-benzylamino)-pyrimidin-4-yl]-3-phenyl-piperazin-2-one;
4-[2-(2,3-Dimethyl-benzylamino)-pyrimidin-4-yl]-3-phenyl-piperazin-2-one;
4-[2-(2,4-Dimethoxy-benzylamino)-pyrimidin-4-yl]-3-phenyl-piperazin-2-one;
3-Phenyl-4-{2-[(pyridin-3-ylmethyl)-amino]-pyrimidin-4-yl}-piperazin-2-one;
4-[2-(3,4-Dihydro-1H-isoquinolin-2-yl)-pyrimidin-4-yl]-3-phenyl-piperazin-2-one;

3-Phenyl-4-[2-(1-phenyl-ethylamino)-pyrimidin-4-yl]-piperazin-2-one;
4-[2-(3-Methyl-benzylamino)-pyrimidin-4-yl]-3-phenyl-piperazin-2-one;
4-{2-[(Furan-2-ylmethyl)-amino]-pyrimidin-4-yl}-3-phenyl-piperazin-2-one;
3-Phenyl-4-{2-[(thiophen-2-ylmethyl)-amino]-pyrimidin-4-yl}-piperazin-2-one;
3-Phenyl-4-(2-phenyl-pyrimidin-4-yl)-piperazin-2-one;
3-[4-(3-Oxo-2-phenyl-piperazin-1-yl)-pyrimidin-2-yl]-benzonitrile;
4-[4-(3-Oxo-2-phenyl-piperazin-1-yl)-pyrimidin-2-yl]-benzonitrile;
4-[2-(4-Chloro-phenyl)-pyrimidin-4-yl]-3-phenyl-piperazin-2-one;
4-[2-(3-Chloro-phenyl)-pyrimidin-4-yl]-3-phenyl-piperazin-2-one; or
4-[2-(1H-Indol-5-yl)-pyrimidin-4-yl]-3-phenyl-piperazin-2-one;

or a salt or N-oxides thereof.

14. A pharmaceutical composition comprising a compound according to claim 1 together with one or more pharmaceutically acceptable carriers, excipients or diluents.

\* \* \* \* \*

UNITED STATES PATENT AND TRADEMARK OFFICE
CERTIFICATE OF CORRECTION

| | | |
|---|---|---|
| PATENT NO. | : 7,323,464 B2 | Page 1 of 1 |
| APPLICATION NO. | : 10/495885 | |
| DATED | : January 29, 2008 | |
| INVENTOR(S) | : Jeremy Martin Davis et al. | |

It is certified that error appears in the above-identified patent and that said Letters Patent is hereby corrected as shown below:

Column 58, Line 60, Claim 1, please delete "$C_{3-11}$" and add --$C_{3-10}$--

Column 62, Line 4, Claim 13, please delete "2yl" and add --2-yl--

Column 62, Line 50, Claim 13, please delete "pyrimidin" and add --pyridin--

Column 64, Line 7, Claim 17, please delete "oxides" and add --oxide--

Signed and Sealed this

First Day of July, 2008

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial
<220> FEATURE:
<223> OTHER INFORMATION: Synthetic Construct

<400> SEQUENCE: 1

His His His His His His
1               5
```